United States Patent
Cheng et al.

(10) Patent No.: US 10,117,886 B2
(45) Date of Patent: Nov. 6, 2018

(54) HYALURONIDASE AND A LOW DENSITY SECOND PEG LAYER ON THE SURFACE OF THERAPEUTIC-ENCAPSULATED NANOPARTICLES TO ENHANCE NANOPARTICLE DIFFUSION AND CIRCULATION

(71) Applicants: Hao Cheng, Merion Station, PA (US); Hao Zhou, Philadelphia, PA (US)

(72) Inventors: Hao Cheng, Merion Station, PA (US); Hao Zhou, Philadelphia, PA (US)

( * ) Notice: Subject to any disclaimer, the term of this patent is extended or adjusted under 35 U.S.C. 154(b) by 0 days.

(21) Appl. No.: 14/726,770

(22) Filed: Jun. 1, 2015

(65) Prior Publication Data

US 2015/0342883 A1     Dec. 3, 2015

Related U.S. Application Data

(60) Provisional application No. 62/005,809, filed on May 30, 2014.

(51) Int. Cl.
| | | |
|---|---|---|
| *A61K 9/51* | (2006.01) | |
| *A61K 31/704* | (2006.01) | |
| *A61K 47/48* | (2006.01) | |

(52) U.S. Cl.
CPC .......... *A61K 31/704* (2013.01); *A61K 9/5153* (2013.01); *A61K 47/48815* (2013.01); *Y10T 428/2982* (2015.01)

(58) Field of Classification Search
CPC ........ A61K 9/51; A61K 9/5123; A61K 9/513; A61K 9/5161
See application file for complete search history.

(56) References Cited

U.S. PATENT DOCUMENTS

| | | | |
|---|---|---|---|
| 7,767,429 B2 | 8/2010 | Bookbinder et al. | |
| 8,303,990 B2 | 11/2012 | Dyer, Jr. et al. | |
| 2004/0133099 A1* | 7/2004 | Dyer, Jr. ............... | A61K 9/0046 600/420 |
| 2005/0227911 A1 | 10/2005 | Goldshtein et al. | |
| 2008/0267876 A1 | 10/2008 | Benita et al. | |
| 2010/0003238 A1* | 1/2010 | Frost .................... | A61K 31/337 424/94.62 |
| 2011/0038900 A1* | 2/2011 | Chakrapani .......... | A61K 39/095 424/400 |
| 2011/0144030 A1* | 6/2011 | Ramis Castelltort ... | A61K 8/02 514/18.8 |
| 2013/0337066 A1 | 12/2013 | Zhang et al. | |

FOREIGN PATENT DOCUMENTS

| | | |
|---|---|---|
| WO | WO2013149141 A1 | 10/2013 |
| WO | WO2013151774 A1 | 10/2013 |

OTHER PUBLICATIONS

Gref, R., et al., "Biodegradable long-circulating polymeric nanospheres." Science 263, 1600-1603 (1994).
Cao, Z.Q., et al., "Superhydrophilic Zwitterionic Polymers Stabilize Liposomes." Langmuir 28, 11625-11632 (2012).
O'Brien, M.E.R., et al., "Reduced cardiotoxicity and comparable efficacy in a phase III trial of pegylated liposomal doxorubicin HCl (CAELYX (TM)/Doxil (R)) versus conventional doxorubicin for first-line treatment of metastatic breast cancer." Annals of Oncology 15, 440-449 (2004).
Cheng, H., et al., "Stem cell membrane engineering for cell rolling using peptide conjugation and tuning of cell-selectin interaction kinetics." Biomaterials 33, 5004-5012 (2012).
Thompson, C.B., et al., "Enzymatic Depletion of Tumor Hyaluronan Induces Antitumor Responses in Preclinical Animal Models." Molecular Cancer Therapeutics 9, 3052-3064 (2010).
Guo, X., et al., "Development of theranostic nanoparticles with the ability to break extracellular cellular matrix for enhanced nanoparticle delivery." ABSTRACT, TechConnect World Summit & Innovation Showcase, 2012, 1 page.
Kansu, Pelin. Biomimetic Nanocarriers for Enhanced Drug Diffusion in Prostate Tumors with a High Level Hyaluronan. Diss. Drexel University, 2014, 82 pages.

* cited by examiner

*Primary Examiner* — Micah Paul Young

(57) ABSTRACT

A delivery system comprising an organic nanoparticle, a hyaluronidase anchored or conjugated to the organic nanoparticle. The organic nanoparticle may be selected from a polymer-based nanoparticle, a lipid-based nanoparticle and nanoparticle formed by lipid-like molecules. In some embodiments, the hyaluronidase is covalently bound to a linker or spacer which, in turn, is anchored or covalently bound to the organic nanoparticle. The delivery system may also comprise an active pharmaceutical agent, a diagnostic agent, and/or a cellular membrane. The organic nanoparticle may further have a low density poly(ethylene glycol) layer on the surface. Methods for using the delivery system including for treating or diagnosing a disease are also provided. The organic nanoparticle provides enhanced diffusion/penetration through the extracellular matrix found in tumors, as well as increased circulation time in a human or animal body.

25 Claims, 35 Drawing Sheets
(35 of 35 Drawing Sheet(s) Filed in Color)

HYALURONIDASE AND A LOW DENSITY SECOND PEG LAYER ON THE SURFACE OF THERAPEUTIC-ENCAPSULATED NANOPARTICLES TO ENHANCE NANOPARTICLE DIFFUSION AND CIRCULATION

RELATED APPLICATION DATA

This application claims the benefit of U.S. Provisional Application No. 62/005,809, filed on May 30, 2014, the contents of which are herein incorporated by reference.

BACKGROUND OF THE INVENTION

1. Field of the Invention

The present invention is directed to the field of delivery systems for delivering pharmaceutical agents to a target tissue. In particular, the present invention is directed to a delivery system where hyaluronidase is located on the surface of nanoparticles to enhance the nanoparticle diffusion in the tissue and/or a relatively low density of second polyethylene glycol layer is located on the surface of nanoparticles to prolong nanoparticle circulation time in an animal or human body.

2. Description of the Related Technology

Nanoparticles alter the pharmacokinetics and toxicity of encapsulated drugs, leading to improved efficacy and reduced side effects of the drugs. Particularly in the therapeutic area of tumors, leaky vasculature and impaired lymphatic drainage of tumors allow the nanoparticles to enter and stay in the tumors. A few nanomedicines have been approved by the U.S. Food and Drug Administration (FDA) for cancer therapy, including albumin-bound paclitaxel for metastatic breast cancer. Some others are in clinical trials, for example Methoxy-PEG-poly(D,L-lactide) taxol (Genexol®-PM) has been approved in South Korea to treat metastatic breast cancer, though is still in phase III trials in U.S. (NCT00876486).

In spite of these limited successes, there are two major challenges in applying nanomedicines in cancer therapy. One is the quick clearance of synthetic nanoparticles by host immune systems before the nanoparticles can reach the tumor sites. The other challenge is the low interstitial diffusion of nanoparticles after entering perivascular areas in solid tumors. Released drugs only penetrate a few layers of tumor cells and are thus inaccessible to hypoxic tumor cells which are usually resistant to chemo- and radiotherapies.

Some progress has been made to address these two challenges. It is known that, through adsorption of opsonin proteins on synthetic nanoparticles, the synthetic nanoparticles become visible to phagocytic cells, resulting in quick clearance of the nanoparticles from blood circulation. Polyethylene glycol (PEG) and some zwitterionic polymers are known to prevent protein adsorption. Nanoparticles (NPs) coated with these polymers have extended circulation times and improved bioavailability of one or more encapsulated pharmaceutical agent. One example is the FDA-approved Doxil which are PEG-coated liposomes with encapsulated doxorubicin.

The low interstitial diffusion of nanoparticles in tumors is mostly due to the elevated density of cells and extracellular matrix (ECM), the high interstitial pressure and heterogeneous vasculature in the tumors. Some small-sized nanoparticles displayed improved diffusion within tumors. However, this strategy is often not practical as small-sized drug nanoparticles are difficult to fabricate. Further, even small nanoparticles still face a low diffusion in tumors as antibodies a few nanometers in size still exhibit the diffusion problem.

Some electronic device-assisted methods have also been developed to enhance nanoparticle diffusion in tumors, such as by reducing interstitial fluid pressure, magnetic field-assisted penetration, and generation of acoustic cavitation by ultrasound. These strategies may be effective for some specific types of tumors, but are not effective in treating metastatic tumors.

A potentially promising approach is the use of a tumor penetrating peptide to enhance diffusion of nanoparticles in the tumor. The peptide has a short motif targeting $\alpha_v$ integrins that are highly expressed in tumor vasculature, and can be proteolytically cleaved in tumors to bind neuropilin-1. This binding increases the penetration of antibodies and nanoparticles in tumors though the actual mechanism is not clear.

Gou et al. "Development of theranostic nanoparticles with the ability to break extracellular cellular matrix for enhanced nanoparticle delivery," NanoTech Conference and Expo 2012, Jun. 18-21, 2012, (Abstract) discloses nanoparticles conjugated with two extracellular matrix proteases, collagenase and/or hyaluronidase. These proteases can temporarily break down the extracellular matrix and open microscopic channels, allowing nanoparticles to spread in the tumor. The proteases were conjugated on polymer-coated quantum dots. After incubation with the 4T1 mammary breast cancer cell line, such nanoparticles were found capable of binding to the cells with intensive binding in the invasive edge of tumor cell clones. It was further found that collagenase displays even better improvement on nanoparticle diffusion in tumors, in comparison with hyaluronidase.

US 2008/0267876 provides a delivery system comprising a polymer-based nanoparticle (NP), and a linker comprising a first portion non-covalently anchored to the nanoparticle, where at least part of the first portion comprises a hydrophobic/lipophilic segment embedded in the nanoparticle, and a second portion comprising a maleimide compound exposed at the outer surface of the nanoparticle. In accordance with one embodiment, the delivery system comprises one or more targeting agents (e.g., antibody or ligand), each covalently bound to the maleimide compound. In accordance with yet another embodiment, the delivery system comprises a drug.

US 2005/0227911 provides hydrophilic dispersions comprising complexes consisting essentially of nanosized particles of a macromolecule wrapped in an amphiphilic polymer such that non-valent bonds are formed between the macromolecule and the amphiphilic polymer. The macromolecules may be a naturally-occurring, synthetic or recombinant polypeptide, protein, polysaccharide or polynucleotide, and the amphiphilic polymer is a polysaccharide or a modified polysaccharide such as starch, chitosan or an alginate. The protein may be hyaluronidase, among a long list of options.

US 2013/0337066 provides a nanoparticle comprising an inner core including a non-cellular material, and an outer surface comprising a membrane derived from a cell or a virus. The nanoparticle may be used in medicament delivery systems where pharmaceutical compositions comprise the nanoparticles. Immunogenic compositions comprising the nanoparticle can be used for eliciting an immune response, and for treating or preventing diseases or conditions, such as neoplasm or cancer, or diseases or conditions associated with cell membrane inserting toxin.

U.S. Pat. No. 7,767,429 discloses soluble neutral active Hyaluronidase Glycoproteins (sHASEGP's) and their use to facilitate administration of other molecules or alleviate glycosaminoglycan associated pathologies. The soluble, neutral active sHASEGP's include asparagine-linked sugar moieties required for a functional neutral active hyaluronidase domain and/or modified amino-terminal leader peptides that enhance secretion of sHASEGP's.

US 2011/0097277 discloses a nanoparticle comprising a core and a surface having a plurality of zwitterionic polymers grafted thereto or grafted therefrom. The core comprises a metal, a metal oxide, a ceramic, a synthetic polymer, a natural polymer, silicon dioxide, a crystal, a semiconductor material, a hydrogel, a liposome, a micelle, or a carbon-based material. The zwitterionic polymer has the formula: $PB-(L_1-N^+(R_a)(R_b)-L_2-A(=O)OM)_n(X^-)_n$, wherein PB is a polymer backbone having n pendant groups $L_1-N^+(R_a)(R_b)-L_2-A(=O)OM)$; $N^+$ is a cationic center; $R_a$ and $R_b$ are independently optional as necessary to provide a cationic center and independently selected from alkyl and aryl; $A(=O)OM$ is the anionic center, wherein A is C, S, SO, P, or PO, and wherein M is a counterion; $L_1$ is a linker that covalently couples the cationic center to the polymer backbone; $L_2$ is a linker that covalently couples the cationic center to the anionic center; $X^-$ is the counter ion associated with the cationic center; and n is an integer from 1 to about 10,000.

U.S. Pat. No. 6,007,845 discloses nanoparticles that are not rapidly cleared from the blood stream by the macrophages of the reticuloendothelial system. The nanoparticles have a core of a multiblock copolymer formed by covalently linking a multifunctional compound with one or more hydrophobic polymers and one or more hydrophilic polymers, and contain a biologically active material. The terminal hydroxyl group of the poly(alkylene glycol) can be used to covalently attach onto the surface of the particles biologically active molecules, including antibodies targeted to specific cells or organs, or molecules affecting the charge, lipophilicity or hydrophilicity of the nanoparticle. The nanoparticles have a prolonged half-life in the blood compared to nanoparticles not containing poly(alkylene glycol) moieties on the surface.

U.S. Pat. No. 5,543,158 discloses nanoparticles that are not rapidly cleared from the blood stream by the macrophages of the reticuloendothelial system, and that can be modified to achieve variable release rates or to target specific cells or organs. The nanoparticles have a biodegradable solid core containing a biologically active material and poly(alkylene glycol) moieties on the surface. The terminal hydroxyl group of the poly(alkylene glycol) can be used to covalently attach onto the surface of the nanoparticles biologically active molecules, including antibodies targeted to specific cells or organs, or molecules affecting the charge, lipophilicity or hydrophilicity of the particle. The surface of the nanoparticle can also be modified by attaching biodegradable polymers of the same structure as those forming the core of the particles.

The present invention provides a therapeutic delivery system that transports hyaluronidase to a tissue, where the hyaluronidase digests the hyaluronan (or hyaluronic acid) in the extracellular matrix of the tissue to improve diffusion of nanoparticles or nanomedicine into the tissue. The delivery system differs from the prior system of Gou et al. because the present invention uses, for example, therapeutic-encapsulating organic nanoparticles that are biocompatible and degradable, while the system of Gou et al. uses inorganic nanoparticles, which have no potential to encapsulate therapeutics. Gou et al. does not disclose detailed procedures about the fabrication of the inorganic nanoparticles. However, it is well known that the methods of fabricating inorganic and organic nanoparticles are dramatically different, and are not interchangeable. In addition, the present invention achieved different and even unexpected results, by using hyaluronidase to significantly enhance organic nanoparticle diffusion and penetration through a matrix including hyaluronan, a core value of the present invention. The present invention also demonstrated i) that hyaluronidase on nanoparticle surfaces is dramatically more efficient than free/or called unconjugated hyaluronidase in assisting nanoparticle diffusion/penetration. ii) the surface modification of hyaluronidase has minor or negligible effect to increase nanoparticle binding to cells. These results were not disclosed in Gou et al.

SUMMARY OF THE INVENTION

In one aspect, the present invention provides a delivery system comprising an organic nanoparticle, and a hyaluronidase anchored or conjugated to the organic nanoparticle. The organic nanoparticle may be selected from a polymer-based nanoparticle, a lipid-based nanoparticle and nanoparticle formed by lipid-like molecules.

In another aspect, the delivery system further comprises an active pharmaceutical agent wherein the active pharmaceutical agent is encapsulated in the organic nanoparticle, or conjugated or anchored on the outer surface of the organic nanoparticle.

In yet another aspect, the delivery system further comprises a diagnostic agent wherein the diagnostic agent is encapsulated in the organic nanoparticle, or conjugated or anchored on the outer surface of the organic nanoparticle.

In yet another aspect, the nanoparticle in the delivery system comprises a cellular membrane on the outer surface of the nanoparticle, and wherein the linker or spacer is conjugated on the cellular membrane or physically inserted in the membrane.

In yet another aspect, the delivery system further comprises an antibody conjugated on surface of the organic nanoparticle, wherein the antibody specifically binds to a surface antigen on a target tissue for the delivery system.

In yet another aspect, the delivery system further comprises a polyethylene glycol polymer or zwitterionic polymer anchored or conjugated on the surface of the organic nanoparticle.

In yet another aspect, the present invention provides a method for treating a disease using the delivery system disclosed herein.

In yet another aspect, the present invention provides a method for diagnosing a disease using the delivery system disclosed herein.

In yet another aspect, the organic nanoparticle of the delivery system comprises poly(ethylene glycol)-b-poly(lactic-co-glycolic acid) and poly(lactic-co-glycolic)-b-poly(ethylene glycol)-maleimide.

In yet another aspect, the organic nanoparticle of the delivery system comprises poly(ethylene glycol)-b-poly(lactic-co-glycolic acid) and poly(lactic-co-glycolic)-b-poly(ethylene glycol)-maleimide at a weight ratio between poly(ethylene glycol)-b-poly(lactic-co-glycolic acid) and poly(lactic-co-glycolic)-b-poly(ethylene glycol)-maleimide in a range of from about 10:1 to about 1:1, or from about 8:1 to about 2:1, or from about 6:1 to about 3:1, or from about 5:1 to about 4:1 for the conjugation of the second poly(ethylene glycol) layer.

In yet another aspect, the organic nanoparticle of the delivery system further comprises a second layer of poly(ethylene glycol) on a surface already covered by a relatively dense poly(ethylene glycol) layer thereof.

In yet another aspect, the second layer of poly(ethylene glycol) on the surface of the organic nanoparticle comprises poly(ethylene glycol) that are covalently linked to less than about 50%, or less than about 45%, or less than about 40%, or less than about 35%, or less than about 30%, or less than about 25%, or less than about 20%, or less than about 15%, or less than about 10% of the poly(ethylene glycol) molecules in the first poly(ethylene glycol) layer.

In yet another aspect, the organic nanoparticle of the delivery system has increased circulation time in an animal or human body, in comparison with nanoparticle without the second layer of poly(ethylene glycol).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE PREFERRED EMBODIMENT(S)

Figure 1:
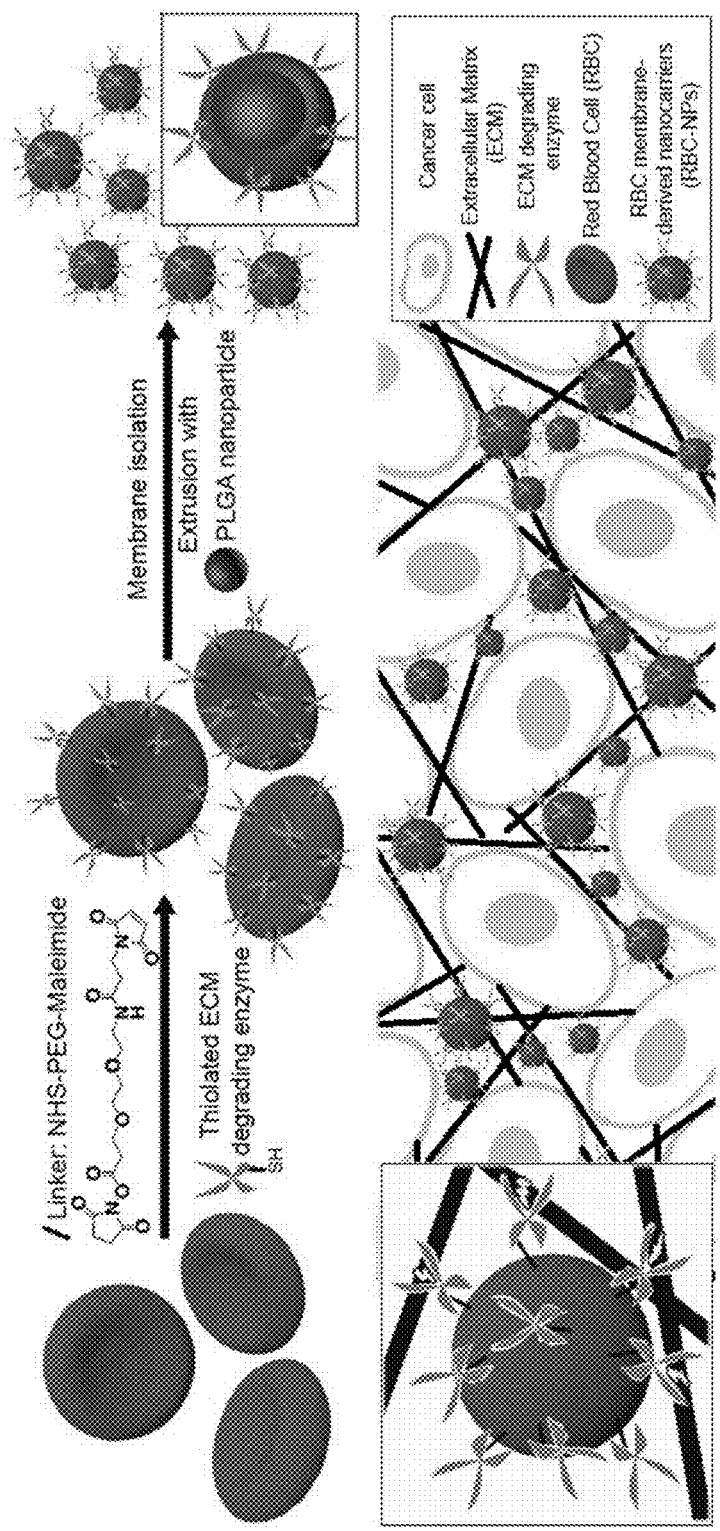
FIG. 1 is a schematic illustration of the fabrication of red blood cell (RBC) membrane-coated nanoparticles (RBC-NPs) and the diffusion of RBC-NPs in a tumor. The efficient interstitial diffusion can be realized through extracellular matrix (ECM) degradation by the hyaluronidase on the RBC-NP surfaces.

For illustrative purposes, the principles of the present disclosure are described by referencing various exemplary embodiments. Although certain embodiments are specifically described herein, one of ordinary skill in the art will readily recognize that the same principles are equally applicable to, and can be employed in, other systems and methods. Before explaining the disclosed embodiments of the present disclosure in detail, it is to be understood that the disclosure is not limited in its application to the details of any particular embodiment shown. Additionally, the terminology used herein is for the purpose of description and not of limitation. Furthermore, although certain methods are described with references to steps that are presented herein in a certain order, in many instances, these steps may be performed in any order as may be appreciated by one skilled in the art; the novel method is therefore not limited to the particular arrangement of steps disclosed herein.

It must be noted that as used herein and in the appended claims, the singular forms "a", "an", and "the" include plural references unless the context clearly dictates otherwise. Furthermore, the terms "a" (or "an"), "one or more" and "at least one" can be used interchangeably herein. The terms "comprising", "including", "having" and "constructed from" can also be used interchangeably.

The present invention provides a delivery system, comprising an organic nanoparticle, and a hyaluronidase anchored or conjugated to the organic nanoparticle. The organic nanoparticle may be selected from a polymer-based nanoparticle, a lipid-based nanoparticle and nanoparticle formed by lipid-like molecules. The delivery system can carry the hyaluronidase to a tissue, where the hyaluronidase exhibits the hyaluronidase activity of degrading hyaluronan in the extracellular matrix of the tissue. The degradation of hyaluronan can improve diffusion of the delivery system and drugs into the tissue. The delivery system of the present invention is not intended to improve binding of the nanoparticles on the cells in the tissue.

Any suitable hyaluronidase or modified hyaluronidase may be employed. A suitable hyaluronidase will exhibit the enzymatic activity of the hyaluronidase. Modified hyaluronidases will also exhibit the enzymatic activity of the hyaluronidase and include those having chemical modifications to, for example, change, replace or add one or more functional groups to the hyaluronidase. For example, the amine, carboxyl and/or thiol groups of the hyaluronidase can be modified or replaced or used to react with a bifunctional compound to provide a different functional group on the hyaluronidase. In this manner, the hyaluronidase can be customized to bind with specific linkers or spacers, as desired. This provides additional flexibility in customizing the properties of the delivery system of the present invention.

Some suitable hyaluronidases useful in the present invention are described in U.S. Pat. No. 7,767,429, which is hereby incorporated herein by reference in its entirety. Other suitable hyaluronidases may also be employed as long as they include at least one functional group for binding to the linker or spacer molecule, for example binding to polyethylene glycol as illustrated in this application, and exhibit hyaluronidase activity when bound to the delivery system of the present invention.

Hereinafter, the combination of hyaluronidase and modified hyaluronidase are collectively referred to as "hyaluronidase."

The term "organic nanoparticle" as used herein refers to a nanoparticle typically having a diameter from about 10 to about 500 nm, or from about 30 to about 300 nm, or from about 40 to about 200 nm, or from about 50 to about 170 nm, and formed from lipid and polymeric organic materials, such as polymers (e.g., polyesters), etc., as opposed to nanoparticles which are mainly inorganic, e.g. gold. The organic nanoparticle may be selected from a polymer-based nanoparticle, a lipid-based nanoparticle and a nanoparticle formed by lipid-like molecules. The term "polymer-based nanoparticles" as used herein refers to nanoparticles formed from any biodegradable, and preferably biocompatible polymer under suitable conditions. Polymer-based nanoparticles include, but not limited to, nanospheres and nanocapsules. Nanospheres (defined as polymeric spherical matrices and may also be called nanogels) and nanocapsules (defined as tiny oil cores surrounded by a distinct wall polymer) are just a few of the shapes that may be used with the delivery system disclosed herein. A variety of biodegradable polymers are available and such polymers are applicable in the present invention. Approved biodegradable, biocompatible and safe polymers that may be used in nanoparticle preparations are described, for example, by Gilding et al. (*Polymer*, vol. 20, pages 1459-1464 (1979)).

Non-limiting examples of nanoparticle-forming biodegradable polymers, such as polyesters, polyhydroxybutyric acids, polyhydroxyvaleric acids; polycaprolactones; polyesteramides; polycyanoacrylates; poly(amino acids); polycarbonates; polyanhydrides; and mixtures of thereof.

Preferably, the polymer is selected from polylactic acid (polylactide), polylactide-polyglycolide, polyglycolide, poly(lactide-co-glycolide), polyethylene glycol-co-lactide (PEG-PLA) and mixtures of thereof.

Another exemplary organic nanoparticle is a lipid-based nanoparticle, which is a nanoparticle including a lipid as one of its major components. Examples of lipid-based nanoparticle include nanoparticle derived from biological membranes and liposomes. The term "liposome" as used herein refers to artificially prepared vesicles composed of at least one lipid bilayer surrounding an inner core. The inner phase, internal phase or inner core (used interchangeably herein) contains substances, such an active pharmaceutical agent. The vesicle may be used to deliver the substances to targeted locations topically within the body. There are three types of liposomes: MLV (multilamellar vesicles), SUV (small unilamellar vesicles about 15-300 nm in diameter) and LUV (large unilamellar vesicles>300 nm in diameter). The volume of material exterior to the vesicles may be referred to as the external phase, outer phase or continuous phase (used interchangeably herein). A liposomal composition can comprise a plurality of individual, separate liposomes and the inner and outer phases usually comprise water.

Liposomes may carry inorganic components, such as metal elements and chelates. Formation of such vesicles requires the presence of "vesicle-forming lipids" which are amphipathic lipids, such as phosphatidylcholine, capable of either forming or being incorporated into a bilayer structure. The latter term includes lipids that are capable of forming a bilayer by themselves or when in combination with another lipid or lipids. An amphipathic lipid is incorporated into a lipid bilayer by having its hydrophobic moiety in contact with the interior, hydrophobic region of the membrane bilayer and its polar head moiety oriented toward an outer, polar surface of the membrane. Hydrophilicity arises from the presence of hydrophilic head groups as well as functional groups such as hydroxyl, phospho, carboxyl, amino or sulfhydryl groups on the lipid molecules.

Hydrophobicity results from the presence of a long chain of aliphatic hydrocarbon groups. Cholesterol is often included in the lipid composition even though it does not possess the traditional lipid structure described above. Depending on the composition, liposomes can exhibit a range of physical and chemical properties that can be tuned to suit intended applications. Examples of derivatized liposomes or liposomes with particular compositions include flexible liposomes, transferosomes, solid lipid nanoparticles, niosomes, cerasomes, nanoemulsions, exosome and so on.

The organic nanoparticle may also be a nanoparticle formed by lipid-like molecules. Exemplary nanoparticles formed by lipid-like molecules are described in Akinc et al., "A combinatorial library of lipid-like materials for delivery of RNAi therapeutics," Nature Biotechnology, vol., 26, pages 561-569 (2008), the disclosure of which incorporated herein by reference in its entirety.

In the delivery system of the present invention, the hyaluronidase is anchored or covalently bonded to the organic nanoparticle. For this purpose the delivery system of the present invention may comprise a linker or spacer that is anchored or conjugated to the organic nanoparticle and covalently bound to the hyaluronidase.

The term "anchor" as used herein denotes the penetration of at least part of the linker or spacer through the particle's outer surface so as to obtain a stable association between the linker or spacer and the particle. The anchoring may be achieved by the incorporation of a moiety (herein termed "the anchor moiety") on a first portion of the linker or spacer which has similar physical characteristics as the polymer. A person skilled in the art will know how to select an anchor moiety to be compatible with the substance from which the nanoparticle is essentially made. For example, when using a hydrophobic polymer to form a nanoparticle matrix, a preferred selection of an anchor moiety is a hydrophilic and/or lipophilic moiety. In other words the anchor moiety should preferably be compatible with the polymer and eventually with the incorporated drug.

The term "linker" as used herein refers to a molecule that comprises at least two reactive or functional groups for forming covalent bonds.

The term "spacer" as used herein refers to a molecule with one reactive or functional group for forming a covalent bond. Typically, a spacer will also include a moiety that allows association of the spacer with the organic nanoparticle by, for example, anchoring to the organic nanoparticle or hydrogen bonding with the organic nanoparticle.

The linker or spacer is used to conjugate or anchor the hyaluronidase to the surface of the nanoparticle of the delivery system. Preferably, the linker or spacer creates sufficient space between the hyaluronidase and the nanoparticle surface thus providing some flexibility to the combination of the linker or spacer and the hyaluronidase of the delivery system.

The linker or spacer may have one or more anchor moieties which may be incorporated in the nanoparticle's surface. For example, a double anchor may be achieved by the use of a spacer comprising 1,2-Distearoyl-sn-Glycero-3-Phosphoethanolamine-N-[Maleimide-(Polyethylene Glycol)2000], which contains two lipophilic moieties.

The term "conjugate" as used herein means that a covalent bond is formed between the two conjugated components (e.g., a linker or spacer and a nanoparticle).

The linker or spacer has also a second portion to which the hyaluronidase is covalently bound. Covalent binding of the enzyme may be achieved by joining the enzyme and a chemically reactive group on the linker of spacer, such as a maleimide group, an N-Hydroxysuccinimide ester group (NHS), a sulfo-NHS ester group and an imidoester group through a covalent bond. The linker or spacer may form a covalent bond with amine, carboxyl or thiol groups on the hyaluronidase. For example, the NHS group may form a stable amide linkage with amine groups in hyaluronidase.

The linker or spacer may be represented by the formulae (I, II, III, IV):

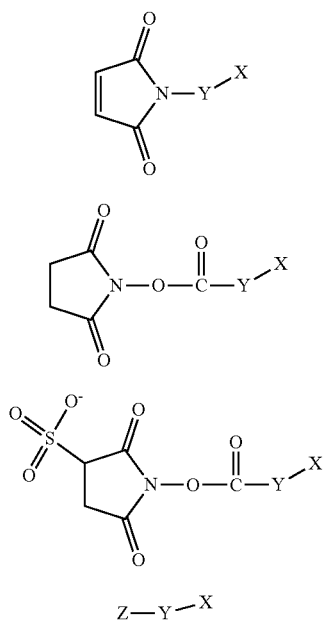

where the linker or spacer has at least one reactive group selected from a maleimide group, an NHS ester group, a Sulfo-NHS ester group and an imidoester group. Z is any other reactive group other than a maleimide group, an NHS ester group, a Sulfo-NHS ester group or an imidoester group, which can form a covalent bond or react with a functional group on a hyaluronidase or modified hyaluronidase. The functional group on the hyaluronidase is typically an amino, carboxyl, or thiol group. If the hyaluronidase is modified, the modification may introduce other functional group(s) to the hyaluronidase, which may also be used to form a covalent bond with a maleimide group, an NHS ester group, a Sulfo-NHS ester group, an imidoester group or Z. In some embodiments, Z may require modification or activation to form a bond with the hyaluronidase or modified hyaluronidase.

Y provides space in between the hyaluronidase and the nanoparticle surface thus providing flexibility to the combination of the linker or space and the hyaluronidase. Y may be long (MW>10,000), or short (MW<10,000). In one embodiment, Y is omitted from the linker or spacer, such that the reactive group and X are directly linked to each other in the linker or spacer. In general, the length of Y has a molecular weight in a range of from about 10 to about 1,000,000. Y can be either a linear or a branched chain. In some embodiments, Y may be polyethylene glycol or a zwitterionic macromolecule or a polysaccharide or modified polysaccharide.

X can be a reactive group for forming a covalent bond to a nanoparticle surface. In this case the whole molecule is a linker. X can also be a hydrophobic group capable of a hydrophobic interaction with the nanoparticle, or X can be a group capable of hydrogen bonding with the nanoparticle, or X can insert itself wholly or partially into a nanoparticle or self-assemble with a nanoparticle. In this case the whole molecule is a spacer since it contains only one reactive group capable of forming a covalent bond.

A linker or spacer can be introduced before, during or after nanoparticle fabrication. In one embodiment, the spacer is poly(D,L-lactic-co-glycolic acid)-block-poly(ethylene glycol) (PLGA-b-PEG) with a carboxyl group at the end of the PEG, in which the carboxyl group is the reactive group for forming a covalent bond directly or indirectly with hyaluronidase. Forming a covalent bond indirectly with hyaluronidase refers to activation, for example with carbodiimide, or reacting the linker or spacer with one or more other chemicals prior to forming a covalent bond with the hyaluronidase.

In an exemplary embodiment, the linker is selected from Succinimidyl-[(N-maleimidopropionamido)-polyethyleneglycol]ester (NHS-PEG-Maleimide, Mw=3400) and Succinimidyl-[(N-maleimidopropionamido)-diethyleneglycol]ester (NHS-PEG$_2$-Maleimide, Mw=425). These type of linkers have the formula:

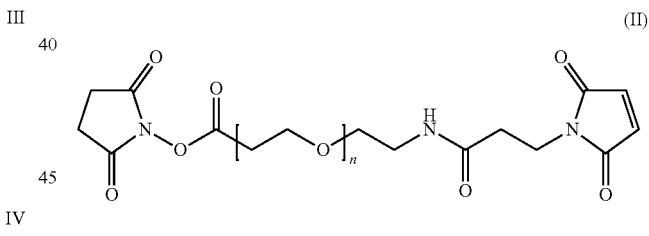

(II)

wherein n is an integer from about 2 to about 30,000, or from about 10 to about 10,000, or from about 15 to about 1,000, or from about 20 to about 500. This linker has an NHS group for forming a covalent bond with the organic nanoparticle and a maleimide group for forming a covalent bond with the thiolated hyaluronidase.

In some embodiments, the organic nanoparticles comprise the polymer poly(D,L-lactic-co-glycolic acid)-poly(ethylene glycol) (PLGA-PEG). In some other embodiments, the organic nanoparticles comprise the polymer poly(D,L-lactic-co-glycolic acid)-poly(ethylene glycol-maleimide) (PLGA-PEG-MAL). In yet other embodiments, the organic nanoparticles comprise both of the polymers PLGA-PEG and PLGA-PEG-MAL. The weight ratio between PLGA-PEG and PLGA-PEG-MAL in the organic nanoparticles may be from about 10:1 to about 1:1, or from about 8:1 to about 2:1, or from about 6:1 to about 3:1, or from about 5:1 to about 4:1. The HAase may be thiolated, such as thiolated PH20, for conjugating to the surface of the organic nanoparticles.

In some embodiments, a second layer of PEG may be added on the surface of the organic nanoparticles. In these embodiments, the organic nanoparticles with PLGA-PEG and/or PLGA-PEG-MAL are linked to a low density second layer of PEG on at least a portion of the first layer of PEG on the surface of the organic nanoparticles. For example, the PEG in the second layer may be conjugated to the PLGA-PEG-MAL through its maleimide group. The second PEG layer then becomes the outmost layer of the nanoparticles.

The second PEG layer has a low density, meaning that the number of PEG chains of the second PEG layer is lower than the number of PEG chains in the first PEG layer. In some embodiments, the PEG chains conjugated on only less than about 50%, or less than about 45%, or less than about 40%, or less than about 35%, or less than about 30%, or less than about 25%, or less than about 20%, or less than about 15%, or less than about 10% of the first layer of PEG chains on the nanoparticle surface. Low density referrers to the number of PEG chains in the second PEG layer is less than 50% of the number of PEG chains in the first PEG layer. That is to say at least 50% of the PEG chains in the first layer were not conjugated with another PEG chain.

In some embodiments, the linker or spacer may be a flexible amino acid chain. In one embodiment, the spacer is the polypeptide CGSGSGSGS, where amino acid C provides a thiol group while the GSGS repeats create space between the nanoparticle and hyaluronidase. In another embodiment, the nanoparticle is a liposome and DSPE-PEG-maleimide can be used as spacer to conjugate hyaluronidase on the liposome.

In some embodiments, the linker or spacer may be a polysaccharide.

In one embodiment, the nanoparticles comprise PLGA-PEG and PLGA-PEG-MAL, with a low density second layer of PEG on their surface. These nanoparticles with conjugated HAase have an enhanced rate of diffusion/penetration through an extracellular matrix such as may exist in typical solid tumor. In addition, these nanoparticles can nearly triple the circulation half-life in a human or animal body in comparison with previously used nanoparticles (without the second layer of PEG). In one example, the circulation half-life was extended from 3.3±0.27 h to 9.3±0.65 h. This dramatic improvement in circulation half-life may be due to the kinetic interference of protein binding on fluctuating PEG chains of the second low density PEG layer. Further conjugating a HAase to the nanoparticles does not noticeably alter the circulation half-life of the nanoparticles.

In some embodiments, the nanoparticles with PLGA-PEG and PLGA-PEG-MAL have two different PEG chains with different lengths and thus can form nanoparticles with extra PEG tails on its surface since the tails of the longer chains form an effective second PEG layer by extending beyond the ends of the shorter PEG chains. Under some circumstances, the nanoparticles with two PEG chains having different lengths may produce a longer circulation time. However, it is challenging to precisely control the ratio of long and short PEGs on the nanoparticle surfaces. The long PEG chains also affect the nanoparticle size, while the strategy of using a PEG chain to conjugate on the nanoparticle for forming the second PEG layer does not change nanoparticle size or the number density of PEG chains on the nanoparticle surfaces.

The organic nanoparticles of the present invention have an enhanced rate of diffusion/penetration through an extracellular matrix which contains HA, which often exist in typical solid tumors, through the function of the conjugated HAase. In addition, surprisingly, the present invention also discovered that the organic nanoparticles of the present invention have increased circulation time in an animal or human body, especially when the organic nanoparticles have the second PEG layer. The increased circulation time is significant because a major challenge for nanoparticle-based medicine is the quick clearance of the nanoparticles by the host immune systems before the nanoparticles and carried drug have sufficient time to act upon tumors or other diseased tissue. With increased circulation time, the nanoparticles of the present invention provide a prolonged period of time for delivering the carried drug to a tumor or other diseased tissue.

The increased circulation time for the nanoparticles of the present invention may be due to the PEG chain fluctuation-induced barrier for protein binding. The fluctuating chains may exert a force (F) on temporarily bound proteins, and this force may increase the dissociation rate constant ($k_{off}$) of protein-PEG binding. For dynamic bonds, it is known that $k_{off}=k_{off}^0 \exp(\gamma F/k_B T)$, in which $k_{off}^0$ is the $k_{off}$ at zero force, $\gamma$ is the bond interaction range, and $k_B T$ is the thermal energy[49]. The force dependent $k_{off}$ has been widely used in understanding cell rolling on endothelium.

The nanoparticles of the present invention can provide significant advantages in delivering an active pharmaceutical agent (carried by the nanoparticles) to tumors or other diseased tissues. With the conjugated HAase, the nanoparticles are capable of diffusing and penetrating deep into tumor or other diseased tissue to release the carried active pharmaceutical agent. In addition, the increased circulation time offers an extended period for the nanoparticles to interact with the tumor or other diseased tissue and thus deliver more of the carried active pharmaceutical agent. As a result, the active pharmaceutical agent carried by the nanoparticles is capable of being delivered to the tumor or other diseased tissue in at least twice the amount that was possible using similar prior art nanoparticles. Thus, the nanoparticles of the present invention can be used as nanocarriers to deliver a wide variety of active pharmaceutical agents or diagnostic agents.

In some embodiments, an active pharmaceutical agent is encapsulated in the organic nanoparticles. The term "encapsulated" or "entrapped" as used herein means that the active pharmaceutical agent is located inside, or in the internal phase or core of, the organic nanoparticle. In some other embodiments, the active pharmaceutical agent may be conjugated or anchored to the outer surface of the organic nanoparticle.

The active pharmaceutical agent may be a drug (therapeutic or prophylactic agent), or a diagnostic (contrasting) agent. The following is a non-limiting list of possible classes of drugs and compounds which may be loaded into the nanoparticle of the invention: Small interfering RNA, biologics (including enzymes, cytokines and antibodies) analgesics, anesthetics, anti-inflammatory agents, anthelmintics, anti-arrhythmic agents, antiasthma agents, antibiotics (including penicillins), anticancer agents (including Taxol), anticoagulants, antidepressants, antidiabetic agents, antiepileptics, antihistamines, IS antitussives, antihypertensive agents, antimuscarinic agents, antimycobacterial agents, antineoplastic agents, antioxidant agents, antipyretics, immunosuppressants, immunostimulants, antithyroid agents, antiviral agents, anxiolytic sedatives (hypnotics and neuroleptics), astringents, bacteriostatic agents, beta-adrenoceptor blocking agents, blood products and substitutes, bronchodilators, buffering agents, cardiac inotropic agents, chemotherapeutics, contrast media, corticosteroids, cough suppressants (expectorants and mucolytics), diagnostic agents, diagnostic imaging agents, diuretics, dopaminergics (antiparkinsonian agents), free radical scavenging agents, growth factors, haemostatics, immunological agents, lipid regulating agents, muscle relaxants, proteins, peptides and polypeptides, parasympathomimetics, parathyroid calcitonin and biphosphonates, prostaglandins, radio-pharmaceuticals, hormones, sex hormones (including steroids), time release binders, anti-allergic agents, stimulants and anoretics, steroids, sympathomimetics, thyroid agents, vaccines, vasodilators, and xanthines Active pharmaceutical agents to be administered in an aerosol formulation are preferably selected from the group consisting of proteins, peptide, bronchodilators, corticosteroids, elastase inhibitors, analgesics, anti-fungals, cysticfibrosis therapies, asthma therapies, emphysema therapies, respiratory distress syndrome therapies, chronic bronchitis therapies, chronic obstructive pulmonary disease therapies, organ-transplant rejection therapies, therapies for tuberculosis and other infections of the lung, fungal infection therapies, respiratory illness therapies associated with acquired immune deficiency syndrome, an oncology drug, an anti-emetic, an analgesic, and a cardiovascular agent.

Anti-cancer active pharmaceutical agents are preferably selected from alkylating agents, antimetabolites, natural products, hormones, small interfering RNA and antagonists, and miscellaneous agents, such as radiosensitizers. Examples of alkylating agents include: (1) alkylating agents having the bis-(2 chloroethyl)-amine group such as, for example, chlormethine, chlorambucile, melphalan, uramustine, mannomustine, extramustinephoshate, mechlorethaminoxide, cyclophosphamide, if osfamide, and trifosfamide; (2) alkylating agents having a substituted aziridine group such as, for example, tretamine, thiotepa, triaziquone, and mitomycine; (3) alkylating agents of the alkyl sulfonate type, such as, for example, busulfan, piposulfan, and piposulfam; (4) alkylating N-alkyl-N-nitrosourea derivatives, such as, for example, carmustine, lomustine, semustine, or; streptozotocine; and (5) alkylating agents of the mitobronitole, dacarbazine and procarbazine type.

Examples of anti-metabolites include: (1) folio acid analogs, such as, for example, methotrexate; (2) pyrimidine analogs such as, for example, fluorouracil, floxuridine, tegafur, cytarabine, idoxuridine, and flucytosine; and (3) purine derivatives such as, for example, mercaptopurine, thioguanine, azathioprine, tiamiprine, vidarabine, pentostatin, and puromycine.

Examples of natural products include: (1) vinca alkaloids, such as, for example, vinblastine and vincristine; (2) epipodophylotoxins, such as, for example, etoposide and teniposide; (3) antibiotics, such as, for example, adriamycine, daunomycine, doctinomycin, daunorubicin, doxorubicin, mithramycin, bleomycin, and mitomycin; (4) enzymes, such as, for example, L-asparaginase; (5) biological response modifiers, such as, for example, alpha-interferon; (6) camptothecin; (7) taxol; and (8) retinoids, such as retinoic acid.

Examples of hormones and antagonists include: (1) adrenocorticosteroids, such as, for example, prednisone; (2) progestins, such as, for example, hydroxyprogesterone caproate, medroxyprogesterone acetate, and megestrol acetate; (3) estrogens, such as, for example, diethylstilbestrol and ethinyl estradiol; (4) anti-estrogens, such as, for example, tamoxifen; (5) androgens, such as, for example, testosterone propionate and fluoxymesterone; (6) anti-androgens, such as, for example, flutamide; and (7) gonadotropin-releasing hormone analogs, such as, for example, leuprolide. Examples of miscellaneous agents include: (1) radiosensitizers, such as, for example, 1,2,4-benzotriazin-3-amine 1,4-dioxide (SR 4889) and 1,2,4-benzotriazine 7-amine 1,4-dioxide (WIN 59075); (2) platinum coordination complexes such as cisplatin and carboplatin; (3) anthracenediones, such as, for example, mitoxantrone; (4) substituted ureas, such as, for example, hydroxyrurea; and (5) adrenocortical suppressants, such as, for example, mitotane and aminoglutethimide.

In addition, the anticancer agent can be an immunosuppressive drug, such as, for example, cyclosporine, azathioprine, sulfasalazine, methoxsalen, and thalidomide.

Analgesic active agents, include, for example, an NSAID or a COX-2 inhibitor. Exemplary NSAIDS that can be formulated in particle of the invention include, but are not limited to, suitable nonacidic and acidic compounds. Suitable nonacidic compounds include, for example, nabumetone, tiaramide, proquazone, bufoxamac, flumizole, epirazole, tinoridine, timegadine, and dapsone. Suitable acidic compounds include, for example, carboxylic acids and enolic acids. Suitable carboxylic acid NSAIDs include, for example: (1) salicylic acids and esters thereof, such as aspirin, diflunisal, benorylate, and fosfosal; (2) acetic acids, such as phenylacetic acids, including diclofenac, alclofenac, and fenclofenac; (3) carbo- and heterocyclic acetic acids such as etodolac, indomethacin, sulindac, tolmetin, fentiazac, and tilomisole; (4) propionic acids, such as carprofen, fenbulen, flurbiprofen, ketoprofen, oxaprozin, suprofen, tiaprofenic acid, ibuprofen, naproxen, fenoprofen, indoprofen, and pirprofen; and (5) fenamic acids, such as flutenamic, mefenamic, meclofenamic, and niflumic. Suitable enolic acid NSAIDs include, for example: (1) pyrazolones such as oxyphenbutazone, phenylbutazone, apazone, and feprazone; and (2) oxicams such as piroxicam, sudoxicam, isoxicam, and tenoxicam.

A description of these classes of active pharmaceutical agents and a listing of species within each class can be found, for instance, in Martindale, The Extra Pharmacopoeia, Twenty-ninth Edition (The Pharmaceutical Press, London, 1989), which is incorporated herein by reference in its entirety.

Poorly water soluble drugs which may be suitably used in the core of the nanoparticles of the present invention include but are not limited to alprazolam, amiodarone, amlodipine, astemizole, atenolol, azathioprine, azelatine, beclomethasone, budesonide, buprenorphine, butalbital, carbamazepine, carbidopa, cefotaxime, cephalexin, cholestyramine, ciprofloxacin, cisapride, cisplatin, clarithromycin, clonazepam, clozapine, cyclosporin, diazepam, diclofenac sodium, digoxin, dipyndamole, divalproex, dobutamine, doxazosin, enalapril, estradiol, etodolac, etoposide, famotidine, felodipine, fentanyl citrate, fexofenadine, finasteride, fluconazole, flunisolide, flurbiprofen, fluvoxamine, furosemide, glipizide, gliburide, ibuprofen, isosorbide dinitrate, isotretinoin, isradipine, itraconazole, ketoconazole, ketoprofen, lamotrigine, lansoprazole, loperamide, loratadine, lorazepam, lovastatin, medroxyprogesterone, mefenamic acid, methylprednisolone, midazolam, mometasone, nabumetone, naproxen, nicergoline, nifedipine, norfloxacin, omeprazole, paclitaxel, phenyloin, piroxicam, quinapril, ramipril, risperidone, sertraline, simvastatin, sulindac, terbinafine, terfenadine, triamcinolone, valproic acid, zolpidem, or pharmaceutically acceptable salts of any of the above-mentioned drugs.

Diagnostic agents can also be delivered use of the delivery system of the present invention. Diagnostic agents may be administered alone or combination with one or more active pharmaceutical agents as described above. The diagnostic agent can be labeled by various techniques. The diagnostic agent may be a radiolabelled compound, fluorescently labeled compound, enzymatically labeled compound and/or include magnetic compound or other materials that can be detected using techniques such as X-ray, ultrasound, magnetic resonance imaging (MRI), computed tomography (CT), or fluoroscopy.

According to one preferred embodiment, the active pharmaceutical agent to be delivered by the delivery system of the present invention is a cytotoxic agent (anti-tumor agents). Cytotoxic agents exemplified herein are doxorubicin, docetaxel, paclitaxel and paclitaxel palmitate.

In some embodiments, the delivery system may comprise more than one active pharmaceutical agent. Further, the nanoparticle may have an encapsulated active pharmaceutical agent and a suitable adjuvant therefore, i.e. an ingredient that facilitates or modified the action of the principle active pharmaceutical agent. For example, in immunotherapy, the adjuvant will be a substance included in a vaccine formulation to enhance or modify the immune-stimulating properties of a vaccine.

In some embodiments, a pharmaceutically acceptable salt of the active pharmaceutical agent may be included in the core of the nanoparticles. The term "pharmaceutically acceptable salt" as used herein refers to any salt which retains the activity of the parent compound and does not impart any deleterious or undesirable effect on a subject to whom it is administered and in the context in which it is administered. Pharmaceutically acceptable salts may be derived from amino acids including, but not limited to, cysteine. Methods for producing compounds as salts are known to those of skill in the art (see, for example, Stahl et al., Handbook of Pharmaceutical Salts: Properties, Selection, and Use, Wiley-VCH; Verlag Helvetica Chimica Acta, Zurich, 2002; Berge et al., *J. Pharm. Sci.*, vol. 66, pages 1-19 (1977)). In some embodiments, a "pharmaceutically acceptable salt" is intended to mean a salt of a free acid or base of a compound represented herein that is non-toxic, biologically tolerable, or otherwise biologically suitable for administration to the subject. See, generally, Berge, et al., *J. Pharm. Sci.*, vol. 66, pages 1-19 (1977). Preferred pharmaceutically acceptable salts are those that are pharmacologically effective and suitable for contact with the tissues of subjects without undue toxicity, irritation, or allergic response. An active pharmaceutical agent described herein may possess a sufficiently acidic group, a sufficiently basic group, both types of functional groups, or more than one of each type, and accordingly react with a number of inorganic or organic bases, and inorganic and organic acids, to form a pharmaceutically acceptable salt.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates.

In some embodiments, a pharmaceutically acceptable carrier may be included in the core of the nanoparticles. The term "pharmaceutically acceptable carrier" as used herein refers to an excipient, diluent, preservative, solubilizer, emulsifier, adjuvant, and/or vehicle with which a compound, such as a multi-drug conjugate, is administered. Such carriers may be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose may also be a carrier. Methods for producing compositions in combination with carriers are known to those of skill in the art. In some embodiments, the language "pharmaceutically acceptable carrier" is intended to include any and all solvents, dispersion media, coatings, isotonic and absorption delaying agents, and the like, compatible with pharmaceutical administration. The use of such media and agents for active pharmaceutically agents is well known in the art. See, e.g., Remington, *The Science and Practice of Pharmacy*, 20$^{th}$ ed., (Lippincott, Williams & Wilkins 2003).

In some embodiments, the active pharmaceutical agent as described herein may be anchored or conjugated on the outer surface of the organic nanoparticles. Any techniques known to a skilled person that can conjugate the active pharmaceutical agent on the organic nanoparticles may be used. Depending on the characteristics of the active pharmaceutical agent, the skilled person can selected a suitable technique to conjugate the active pharmaceutical agent with the nanoparticles.

In some embodiments, an antigen is encapsulated in the organic nanoparticle. The antigen can be delivered to dendritic cells for stimulating the host immune system to generate immunity against any cells that carrier the antigen. For example, the antigen may be a cancer specific cell membrane receptor or portion thereof. Upon delivering the receptor or portion of it to the dendritic cells, the host immune system is stimulated to fight the cancer cells that have the receptor.

In certain embodiments, the outer surface of the organic nanoparticle is partially or completely coated with a cellular membrane. In these embodiments, the linker is conjugated to the cellular membrane at one end, instead of the nanoparticle directly, and conjugated to the hyaluronidase at the other end. The term "cellular membrane" as used herein refers to a membrane obtained from a naturally occurring biological membrane of a cell, cellular organelles, viral particle, or one derived therefrom. The cellular membrane is selectively permeable to ions and organic molecules and controls the movement of substances in and out of cells. The cellular membrane comprises a phospholipid uni- or bilayer, and optionally associated proteins and carbohydrates. As used herein, the term "naturally occurring" refers to one existing in nature. The cellular membrane may be derived from plasma membrane or an intracellular membrane from a unicellular (e.g. a bacterium or fungus) or multicellular organism (e.g., a plant, an animal, a non-human mammal, vertebrate, or a human), or from virus. As used herein, the term "derived therefrom" refers to any subsequent modification of the natural membrane, such as isolating the cellular membrane, creating portions or fragments of the membrane, removing and/or adding certain components, such as lipid, protein or carbohydrates, from or into the membrane taken from a cell or a cellular organelle. A membrane can be derived from a naturally occurring membrane by any suitable methods. For example, a membrane can be prepared or isolated from a cell or a virus and the prepared or isolated membrane can be combined with other substances or materials to form a derived membrane. In another example, a cell or virus can be recombinantly engineered to produce "non-natural" substances that are incorporated into its membrane in vivo, and the cellular or viral membrane can be prepared or isolated from the cell or the virus to form a derived membrane.

In some embodiments, the cellular membrane covering the nanoparticles can be further modified to be saturated or unsaturated with other lipid components, such as cholesterol, free fatty acids, and phospholipids, also can include endogenous or added proteins and carbohydrates, such as cellular surface antigen. In such cases, an excess amount of the other lipid components can be added to the membrane wall which will shed until the concentration in the membrane wall reaches equilibrium, which can be dependent upon the nanoparticle environment.

In certain embodiments, the cellular membrane of the present invention is derived from a blood cell (e.g., red blood cell (RBC), white blood cell (WBC), or platelet). In other embodiments, the cellular membrane is derived from an immune cell (e.g., macrophage, monocyte, B-cell, or T-cell), a tumor or cancer cell, and other cells, such as an epithelial cell, an endothelial cell, or a neural cell. In other embodiments, the cellular membrane is derived from a non-terminally differentiated cell, such as a stem cell, including a hematopoietic stem cell, a bone marrow stem cell, a mesenchymal stem cell, a cardiac stem cell, a neural stem cell. The non-terminally differentiated cell can be isolated in a pluripotent state from tissue or induced to become pluripotent. In yet other embodiments, the cellular membrane is derived from a cell component or cell organelle including, but not limited to, an exosome, a secretory vesicle, a synaptic vesicle, an endoplasmic reticulum (ER), a Golgi apparatus, a mitochondrion, a vacuole or a nucleus.

In some embodiments, an antibody may be conjugated to the outer surface of the organic nanoparticles or the cellular membrane that covers the organic nanoparticles. The antibody may bind to a surface protein on the target tissue, to thereby direct the delivery system to the target tissue. For example, to target a breast cancer tissue, which has specific tumor antigens MUC-1 and epithelial tumor antigen (ETA), an antibody that specifically binds to one of the tumor antigens may be conjugated on the surface of the organic nanoparticles or the cellular membrane that covers the organic nanoparticles.

One problem that faced by many prior art delivery systems is that the host immune system can clean them out quickly, thus limiting the amount of active pharmaceutical agent that can be delivered to the target tissues. In some embodiments of the present invention, in order to evade the host immune system, a polyethylene glycol polymer, polysaccharide, polyamino acid (peptide) or zwitterionic polymer may be used to coat a portion of or the entire outer surface of the organic nanoparticles and/or the hyaluronidase. Specifically, these two types of polymers are anchored or conjugated on the surface of the organic nanoparticles or on the conjugated hyaluronidase.

The polyethylene glycol polymer (not the spacer as discussed above) may be polyethylene glycol and derivatives thereof having a weight average molecular weight over a range of from about 100 to about 1,000,000, or from about 500 to 500,000.

Zwitterionic polymers are polymers having a balance of positive and negative charge. Zwitterionic polymers can be highly resistant to protein adsorption, thus making the delivery system of the present invention invisible to the host immune system. Due to their biomimetic nature, zwitterionic polymers, such as phosphobetaine, sulfobetaine, and carboxybetaine polymers, exhibit high biocompatibility.

Zwitterionic polymers are formed by polymerizing zwitterionic monomers. "Zwitterionic monomer" means a polymerizable molecule containing cationic and anionic (charged) functionality in equal proportions, so that the molecule is net neutral overall. Representative zwitterionic monomers include N,-dimethyl-N-acryloyloxyethyl-N-(3-sulfopropyl)-ammonium betaine, N, N-dimethyl-N-acrylamidopropyl-N-(2-carboxymethyl)-ammonium betaine, N,N-dimethyl-N-acrylamidopropyl-N-(3-sulfopropyl)-ammonium betaine, N, N-dimethyl-N-acrylamidopropyl-N-(2-carboxymethyl)-ammonium betaine, 2-(methylthio)ethyl methacryloyl-S-(sulfopropyl)-sulfonium betaine, 2-[(2-acryloylethyl)dimethylammonio]ethyl 2-methyl phosphate, 2-(acryloyloxyethyl)-2-(trimethylammonium)ethyl phosphate, [(2-acryloylethyl)dimethylammonio]methyl phosphonic acid, 2-methacryloyloxyethyl phosphorylcholine (MPC), 2-[(3-acrylamidopropyl)dimethylammonio]ethyl 2'-isopropyl phosphate (AAPI), 1-vinyl-3-(3-sulfopropyl) imidazolium hydroxide, (2-acryloxyethyl) carboxymethyl methylsulfonium chloride, 1-(3-sulfopropyl)-2-vinylpyridinium betaine, V-(4-sulfobutyl)-N-methyl-N,N-diallylamine ammonium betaine (MDABS), N, N-diallyl-.-V-methyl-N-(2-sulfoethyl) ammonium betaine, and the like.

Preferred zwitterionic monomers include N, N-dimethyl-N-(3-methacrylamidopropyl)-N-(3-sulfopropyl) ammonium betaine, N, N-dimethyl-iŸ-acryloyloxyethyl-N-(3-sulfopropyl)-ammonium betaine, N, N-dimethyl-N-acrylamidopropyl-N-(2-carboxymethyl)-ammonium betaine and N, N-dimethyl-N-methacryloyloxyethyl-N-(3-sulfopropyl)-ammonium betaine.

The present invention provides nanoparticles that combine two beneficial functions: long circulation time and efficient penetration into tumors or other diseased tissue. The low density of second PEG layer-modified nanoparticles gain a long in vivo circulation time while these nanoparticles also benefit from the hyaluronidase to penetrate and diffuse into tumors or other diseased tissue. These beneficial functions allow a lower dose of drug and hyaluronidase to be used in cancer treatment compared to prior nanoparticles and combination of free/unconjugated pegylated PH20 and therapeutics.

In current clinical trials and animal studies, a high dose of free hyaluronidase is usually administered a few hours before applying anti-cancer agents to deplete tumor HA thus ensure delivery of active pharmaceutic agent to the tumor cells. It is unavoidable that the administered free hyaluronidase will degrade HA in other tissues since it is not selective. Hyaluronidase conjugated on the nanoparticles of the present invention cannot pass through the wall of a healthy blood capillary via hydrostatic pressure and thus will only degrade HA on the paths of nanoparticle diffusion. These characteristics offer efficient utilization of the hyaluronidase and are likely reduce potential side effects. Further, the nanoparticles of the present invention require only one injection of nanoparticles with conjugated hyaluronidase, instead of two injections of free hyaluronidase and nanoparticles separately, which will improve patient compliance. Finally, unlike collagen, HA does not provide mechanical support to cells and normally undergoes rapid degradation and synthesis in humans. The conjugated HAase only degrades HA along the path of nanoparticle diffusion while still maintaining the major basic structure of HA in ECM. The temporary and minor degradation of tumor HA by the conjugated hyaluronidase is not expected to promote cancer metastasis, especially when the degradation is minor and results in direct exposure of cancer cells to carried therapeutics.

The nanoparticles of the present invention can be used to deliver active pharmaceutical agents such as chemotherapeutic agents, peptides, proteins, DNA and RNA-based therapeutics to tumors or other diseased tissues.

The following examples are illustrative, but not limiting, of the methods and devices of the present disclosure. Other suitable modifications and adaptations of the variety of conditions and parameters normally encountered in the field, and which are obvious to those skilled in the art, are within the scope of the disclosure.

EXAMPLES

Example 1

In this example, a delivery system was produced where the nanoparticles are covered with a red blood cell membrane conjugated with hyaluronidase (FIG. 1).

A recombinant hyaluronidase PH20 (in pH6.5, 10 mM sodium phosphate, 150 mM NaCl buffer was obtained from Halozyme, Inc) was first thiolated with Traut's reaction. Specifically, 5-fold of Traut's reagent in PBS was added into 1 mg/mL PH20 solution in PBS and reacted for 1 h at room temperature under stirring. After the reaction, the thiolated PH20 was purified by filtering through a desalting column (Thermo Scientific.). Fresh red blood cells (RBCs) were collected from mice through a submandibular blood collection method and kept in a blood collecting tube containing 0.04 mL EDTAK3 7.5% solution. The cells were washed three times in PBS by centrifuge at 600×g for 5 min.

Two linkers each having two functional groups were used in this example: a long linker, Succinimidyl-[(N-maleimidopropionamido)-polyethyleneglycol]ester (NHS-PEG-Maleimide, Mw=3400) was purchased from NANOCS, whereas a short linker, Succinimidyl-[(N-maleimidopropionamido)-diethyleneglycol]ester (NHS-$PEG_2$-Maleimide, Mw=425), was purchased from Thermo Scientific. The purchased long or short linkers were dissolved in DMSO before being added to PBS at a final concentration of 100 μM. RBCs were treated with the linkers at a cell concentration equivalent to 0.01 mL of whole blood/mL in PBS at room temperature for 20 min for the short linker and 1 h for the long linker. The maleimide-modified cells (with linkers) were washed three times with PBS and then re-suspended in PBS at a concentration equivalent to 0.04 mL of whole blood/mL before adding the thiolated PH20 at a concentration of 20 μg/mL. After shaking cells at room temperature for 20 minutes for the short linker and 1 h for the long linker, the RBCs were washed three times thoroughly with PBS to get rid of all unconjugated PH20. The linker conjugated RBCs were ready for further use.

In a separate experiment, to image the hyaluronidase on RBC, the hyaluronidase (from bovine testes, Sigma) was first labeled with NHS-Fluourescein (8-fold) at a concentration of 2 mg/mL by incubation in PBS for 2 h at room temperature. Then the fluorescence labeled hyaluronidase was purified through the desalting column followed with a Traut's reaction. The labeled hyaluronidase was added to RBCs conjugated with long linkers and short linkers respectively at a final concentration of 1 mg/mL. After the reaction, the RBCs were washed three times with PBS before being imaged under a confocal microscope.

Figure 2A:
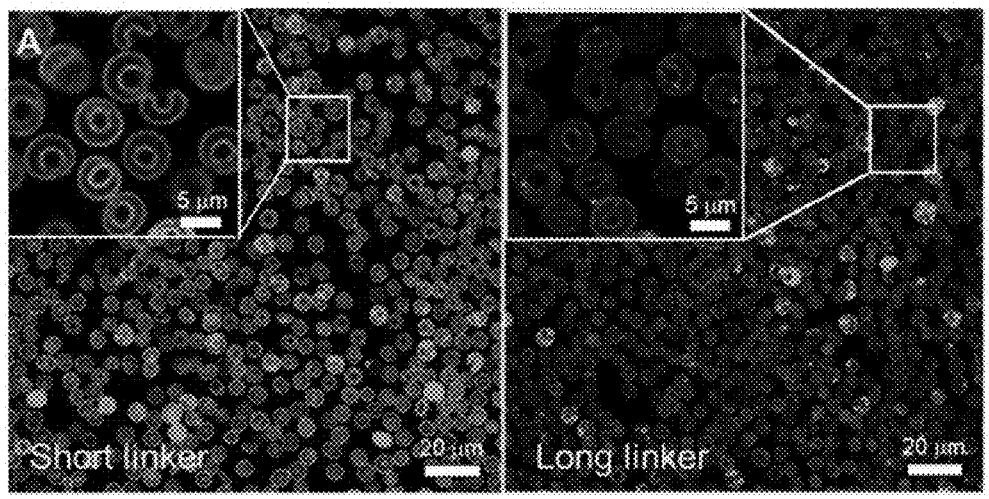
FIG. 2A shows confocal microscopy images of RBCs conjugated with FITC-labeled bovine hyaluronidase (HAase). The left panel shows HAase conjugated on RBCs with a short linker, while the right panel shows HAase conjugated on RBCs with a long linker.

The confocal microscopy images of hyaluronidase-conjugated RBCs are shown in FIG. 2A, where fluorescence labeled hyaluronidase is observed on the RBCs. No fluorescent signal was observed when hyaluronidase was not thiolated or no linker molecule was added in this experiment (data not shown), demonstrating that enzymes were chemically conjugated on the RBCs.

Nanoparticles (NPs) were prepared using a modified solvent displacement method. PLGA, or poly(D,L-lactic-co-glycolic acid) was purchased from DURECT Corporation. PLGA was first dissolved in acetone at various concentrations before swiftly adding to 4 times its volume of deionized (DI) $H_2O$. The mixture was placed in fume hood overnight to remove the acetone. PLGA nanoparticles encapsulating DiD (PLGA-DiD NPs) and Paclitaxel (PLGA-Ptx NPs) were prepared by dissolving 0.05% (w %) of DiD or 1% (w %) of Ptx in acetone together with PLGA before adding to water. The resulting PLGA NPs were then subsequently filtered through 450 nm and 200 nm syringe filters to get rid of possible aggregates of NPs.

Before isolation of cellular membranes, RBCs (with linker and conjugated hyaluronidase PH20) were counted and it was found that about $7 \times 10^9$ RBCs may be derived from 1 mL of whole blood. 950 μL of 0.2 mM EDTA in $H_2O$ was added to rupture RBCs (0.1 mL) using the osmotic pressure followed with adding 50 μL of 20×PBS. The membranes were centrifuged at 17000×g for 7 min. The same process was repeated two more times before the pink pallet was collected and re-suspended in DI $H_2O$ at a concentration of 50 μL worth of whole blood/mL.

The RBC cellular membranes were extruded seven times back and forth through 100 nm extrusion membranes for coating small NPs (e.g., 85 nm NPs) or 200 nm extrusion membranes for large NPs (e.g., 125 nm NPs) after 10 min of sonication (Fs30D, Fisher Scientific). The resulting RBC vesicles were then mixed with 75 μL PLGA NP solutions. The mixture was then extruded again for 11 times back and forth through a 400 nm extrusion membrane before collecting the membrane coated NPs. The resulted nanoparticles: PLGA NPs, PLGA-DiD NPs and PLGA-Ptx NPs were used in the following PH20 activity assay, cell uptake assay and Thiazolyl Blue Tetrazolium Bromide (MTT) assay, respectively.

Sizes and zeta potentials of the prepared nanoparticles were measured by dynamic light scattering (DLS, Zetasizer Nano ZS90). For transmission electron microscopy (TEM), a carbon coated grid was cleaned by plasma and 10 μL of nanoparticles with a concentration of 0.2 mg/mL was added on the grid. The grid was then rinsed with DI water. 5 μL of 2% uranyl acetate water solution was then dropped on the grid and filter paper was used to absorb the solution instantly from the grid. This step was repeated 3 times and the grid with NPs was observed using a transmission electron microscope (TEM, JEOL JEM2100) at 200 KV.

Figure 2B:
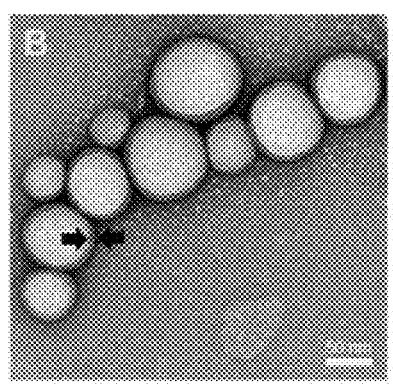
FIG. 2B represents a transmission electron microscope (TEM) image of PH20-RBC-NPs (PH20, a recombinant human hyaluronidase conjugated to red blood cell (RBC) membrane on nanoparticles (NPs)) as fabricated in Example 1. Cell membrane coating is marked by arrows.
Figure 6:
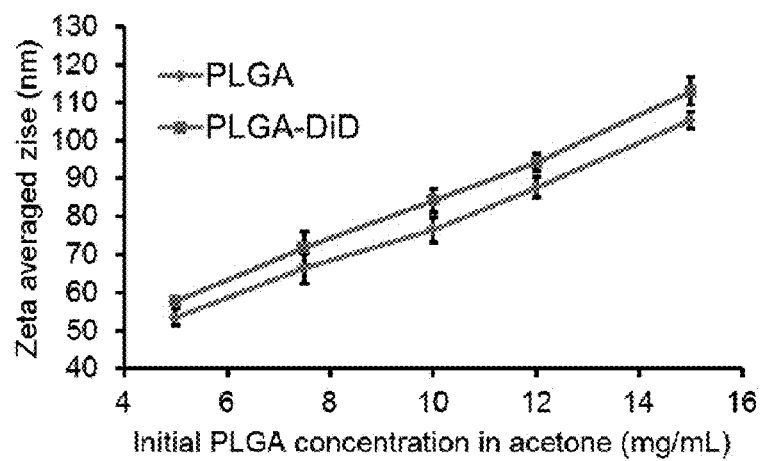
FIG. 6 shows the zeta-averaged sizes of poly(D,L-lactic-co-glycolic acid) (PLGA) and PLGA-DiD nanoparticles prepared by PLGA/PLGA-DiD acetone solutions at various concentrations (mean±s.d., n=3).
Figure 7:
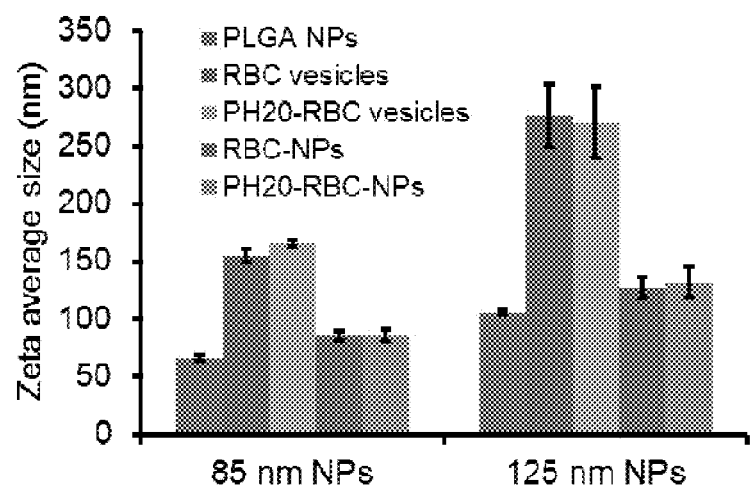
FIG. 7 shows the zeta average sizes of PLGA NPs, RBC-NPs and PH20-RBC-NPs (values are mean±s.d., n=3).
Figure 8:
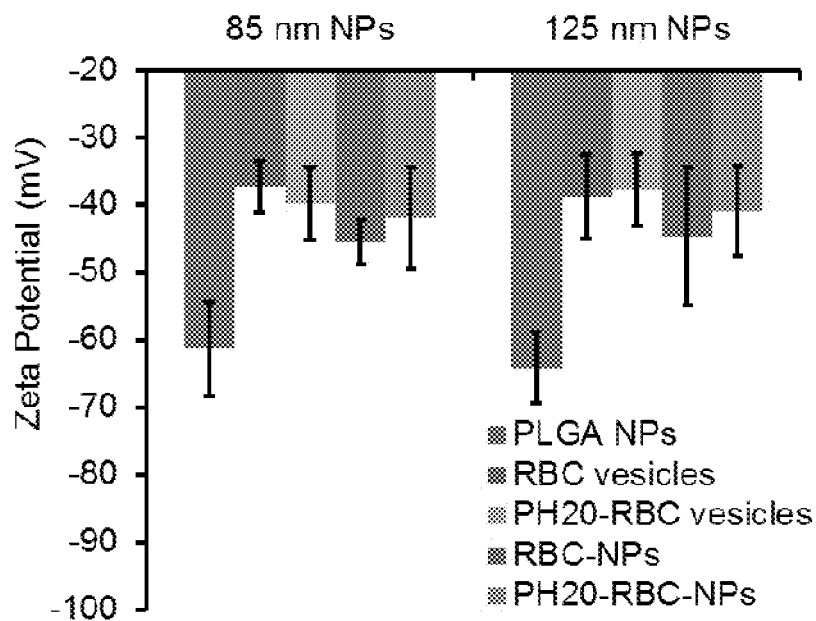
FIG. 8 shows the zeta potential of PLGA NPs, RBC-NPs and PH20-RBC-NPs (values are mean±s.d., n=3).

By adjusting the PLGA concentration in acetone, PLGA NPs ranging from 50 nm to 125 nm can be generated (FIG. 6). PLGA NPs with two sizes, 65 nm and 105 nm prepared from 7.5 mg/mL and 15 mg/mL of PLGA respectively in acetone were selected for further study. Coating of RBC membranes on the surfaces of PLGA NPs was observed by TEM images (FIG. 2B), so were the changes in particle size and zeta potential (FIGS. 7 and 8). The cellular membrane on the PLGA NPs had a thickness of around 8 nm as shown by the arrows in the TEM image (FIG. 2B) and around 10 nm according to the zeta average size. Incorporating 0.05% DiD in PLGA increased the PLGA NP size by around 5 nm for all the NPs at various size ranges (FIG. 6). Adding PH20 on the RBC membrane coated NPs did not change the sizes or zeta potential of the vesicles and NPs significantly (FIGS. 7 and 8).

Two linkers with different numbers of repeating PEG units were used in the conjugation of FITC-labeled PH20 onto the cellular membrane of RBCs. Though the same amounts/concentrations of PH20 and RBCs were used, the PH20 conjugation using the longer linker was a slower process, as shown by the lower fluorescence intensities of PH20-RBCs (FIG. 2A), indicating less PH20 was conjugated on RBCs using the longer linker. It is likely due to a lower efficiency for the end maleimide group on a long chain to react with PH20, in comparison with the same maleimide group on a shorter chain.

The enzymatic activity of PH20 conjugated with long and short linkers on cells (PH20-Cells) as well as on RBC-membrane coated NPs (125 nm PH20-RBC-NPs and 85 nm PH20-RBC-NPs) were measured with a modified microtiter-based assay. Briefly, hyaluronan (HA) was dissolved in 0.1 M 2-(N-morpholino) ethanesulfonic acid (Mes), pH 5.0 buffer at a concentration of 1 mg/mL by stirring overnight at 4° C. N-hydroxysulfosuccinimide (Sulfo-NHS) was then added to the HA solution to a final concentration of 0.184 mg/mL. Biotin hydrazide was dissolved in DMSO as a stock solution of 100 mM and diluted 100 times in the HA solution. 1-ethyl-3-(3-dimethylamin-opropyl) carbidodiim-ide (EDC) was prepared as a 100 mM stock solution in DI $H_2O$ and then added to the HA-biotin solution at a final concentration of 30 mM. This solution was stirred overnight at 4° C. before stopping the reaction by the addition of 4 M guanidine-HCl. Unlinked biotin and EDC were removed by dialysis against DI $H_2O$ overnight. To coat the biotinylated HA (bHA) on the plates (96-well COVALINK-NH micro-titer plate, Thermo Fisher Scientific.), the bHA solution was first mixed with Sulfo-NHS at a concentration of 0.2 mg/mL bHA and 0.184 mg/mL Sulfo-NHS. 50 µL of the resulting solution was pipetted into each well before adding another 50 µL of EDC at a concentration of 0.123 mg/mL in DI $H_2O$. The plates were incubated overnight at 4° C. After covalent immobilization of bHA on the microtiter plates, the coupling solution was removed and the plate was washed three times with PBS containing 2 M NaCl and 50 mM $MgSO_4$.

The plate was then equilibrated with the assay buffer, PBS, for 1 h before the assay. A standard activity curve of free PH20 in PBS was generated by diluting 1 mg/mL PH20 solution with original activity of 116000 U/mg to a series of solutions with PH20 activity from 1 U/mL to 1000 U/mL. The NPs samples were diluted five times in PBS before adding to a 100 µL/well in triplicates. After 50 min of incubation at 37° C., the reaction was terminated by adding 200 µL 6M Guanidine-HCl per well followed by three washes of 300 µL/well with PBS, 2 M NaCl, 50 mM $MgSO_4$, 0.05% Tween 20. Horseradish peroxidase conjugated Streptavidin (HRP-Streptavidin) at a concentration of 0.125 µg/mL in PBS containing 0.1% Tween 20 was used to probe remaining bHA. This solution was added at 100 µL/well and incubated for 30 min at room temperature. The plate was then washed five times before adding 100 µL/well of the o-Phenylenediamine (OPD) substrate solution. The OPD solution was prepared by dissolving one 5 mg-tablet of OPD in 5 mL of 0.1 M citrate-$PO_4$ buffer, pH=5, with 3.75 µL of 30% $H_2O_2$. The plate was incubated in the dark for 5 min before quenching with 50 µL/well of 4 M $H_2SO_4$ solution. Absorbance for each well was read at 492 nm (TECAN, Infinite M200) and the PH20 activity of each sample was determined by comparing with the standard curve.

Figure 2C:
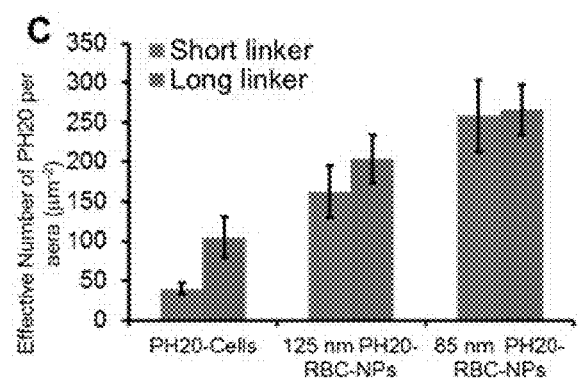
FIG. 2C shows hyaluronidase (PH20,) enzymatic activity of PH20-modified cells and PH20-RBC-NPs with long and short linkers. Data represent mean±s.d. (n=3).

Interestingly, although PH20 conjugated via the long linker had a lower density of PH20 on the RBC, the cells modified with long linker showed more than twice the enzymatic activity compared to cells modified with short linker (FIG. 2C, PH20-Cells). This may be due to the fact that conjugated PH20 with a long linker has a more flexibility to access and degrade substrates around the RBC than PH20 with a short linker. Similarly, conjugation of PH20 on the RBC-membrane coated NPs through the longer linker showed higher overall effective activities of PH20 per unit area on NPs than the same NPs with the shorter linker (FIG. 2C, 125 nm PH20-RBC-NPs and 85 nm PH20-RBC-NPs), even though the RBC membrane was originally isolated from the same batch of RBCs. Further, when PH20 was conjugated on RBC-membrane coated NPs, the NPs with smaller sizes (85 nm) showed higher effective enzyme activity than NPs with larger size (125 nm), using either long or short linkers (FIG. 2C). However, for the NPs having a size of 85 nm, the difference on effective enzyme activity using either long linker or short link was insignificant (FIG. 2C). It is worth noting that PH20 conjugated via long linker is still more effective for 85 nm nanoparticles because their density is lower than is the case using a shorter linker.

Figure 9:
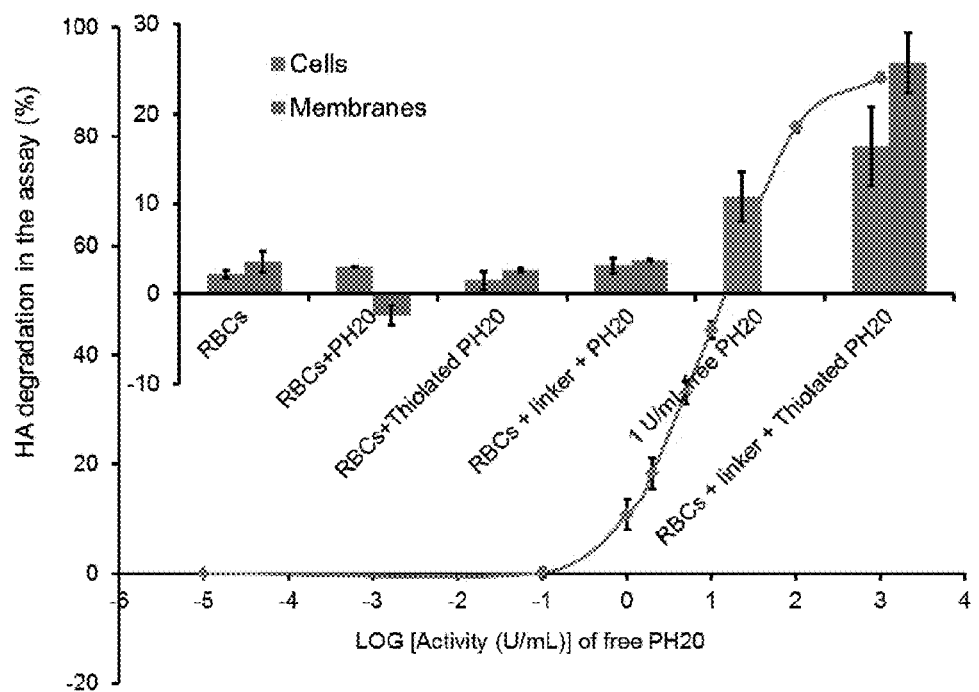
FIG. 9 shows results of hyaluronidase (PH20) activity of the enzyme on RBCs and isolated RBC membranes with various conjugation conditions, as assayed in degradation of hyaluronan. Without thiolation of PH20 or using linker molecules, PH20 cannot be conjugated on cell membranes and do not show activity. The curve is the standard curve of free PH20 of 0.1 U/mL to 1000 U/mL. Values are mean±s.d., n=3.

In order to rule out the influence of non-covalently attached PH20 on the RBCs or RBC-membrane coated NPs during conjugation step, controls of non-thiolated PH20 (which will not conjugate with the linker), RBCs without linker molecule treatment and a simple mixture of cells and PH20 were analyzed along with the PH20-RBC-NPs. This analysis showed that in the controls where PH20 cannot covalently bind to the RBC membrane, no significant amount of PH20 was non-covalently attached on the RBCs (FIG. 9). It was discovered that washing of the RBCs followed by centrifugation was sufficient to remove the non-covalently attached PH20 from the RBCs.

Based on these results, the long linker was selected for PH20-RBC-NP fabrication for further experiments, since its lower conjugation amount on the RBC membrane could better maintain the surface properties of RBC membranes while still showing comparable effective activities of PH20 as the same NPs fabricated using the short linker. It is estimated that there were about 10 effective PH20 molecules on each 125 nm PH20-RBC-NPs under this fabrication condition, giving an extremely high local concentration of PH20 on the nanoparticles.

Diffusion (or uptake) of the PH20-RBC-NPs (with long linker) in PC3 cells (a human prostate cancer cell line) was then studied. PC3 cells were maintained in F-12K medium (ATCC) containing 10% fetal bovine serum in 5% $CO_2$ incubator at 37° C. and sub-cultured every 2-3 days when reaching 90% confluence. The same nanoparticles without conjugated PH20 (RBC-NPs) were used as a control, and were prepared using the same method to fabricate PH20-RBC-NPs, but without enzyme conjugation. The amount of NPs in all samples were equalized via the fluorescence intensity of DiD. PC3 cells were cultured on round glass coverslips in a 12-well plate for two days to reach 70% confluence before the treatment with PH20-RBC-NPs.

PH20-RBC-NP solutions were diluted in cell culture media by 5 times before adding 1 mL/well and incubating at 37° C. for several time points for the kinetics study. The cells were then fixed and observed under a confocal microscope (Olympus IX81, 60×, C.A.=79 µm) with 405 nm and 635 nm lasers for detecting 4',6-diamidino-2-phenylindole (DAPI) and DiD respectively. The high voltage (HV) and gain were set high enough to just avoid saturation and % off (offset) was set low enough to include all signals against background.

Figure 3A:
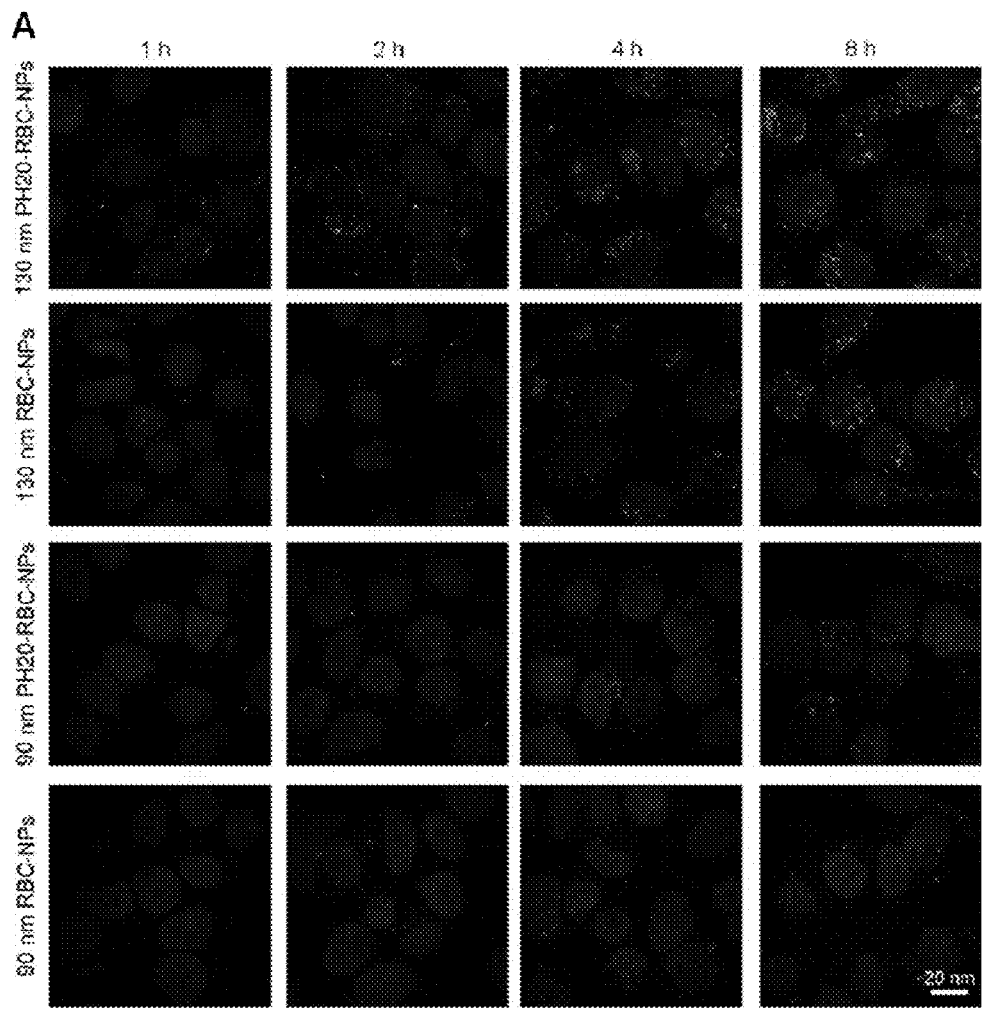
FIG. 3A shows confocal microscopy images of PC3 cells (a prostate cancer cell line) after treatment with DiD-labeled 130 nm PH20-RBC-NPs, 130 nm RBC-NPs, 90 nm PH20-RBC-NPs and 90 nm RBC-NPs respectively with treatment time of 1 h, 2 h, 4 h and 8 h, according to procedure of Example 1. RBC-NPs are nanoparticles coated with red blood cell membrane. DiD stands for 1,1'-Dioctadecyl-3,3,3',3'-Tetramethylindodicarbocyanine, 4-Chlorobenzenesulfonate Salt.
Figure 3B:
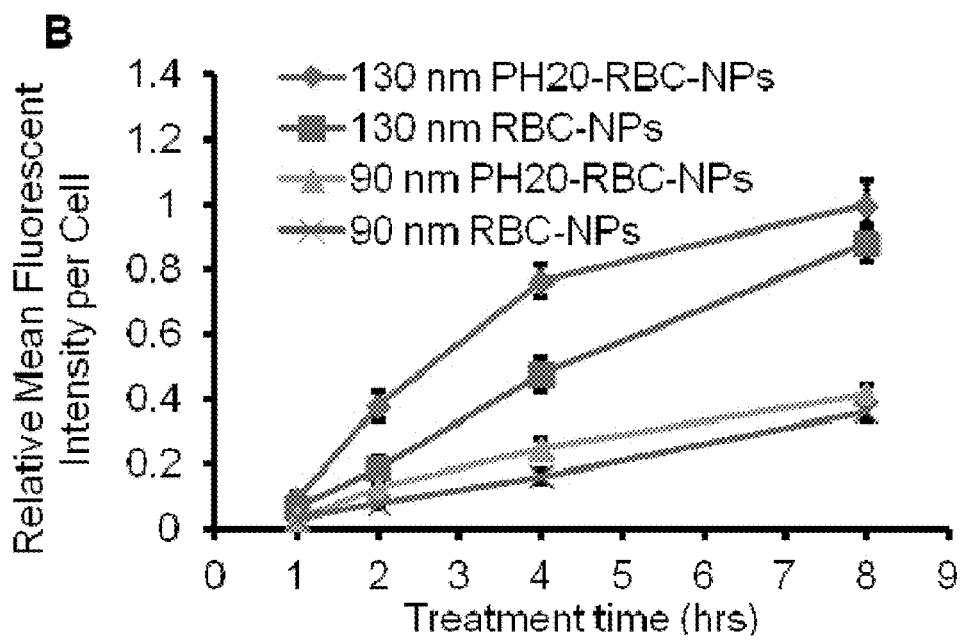
FIG. 3B shows mean fluorescence intensity per PC3 cell after treatment by the nanoparticles in FIG. 3A. The values are averaged by the number of cells. The relative value is compared with the value of 130 nm PH20-RBC-NPs after 8 h treatment.
Figure 3C:
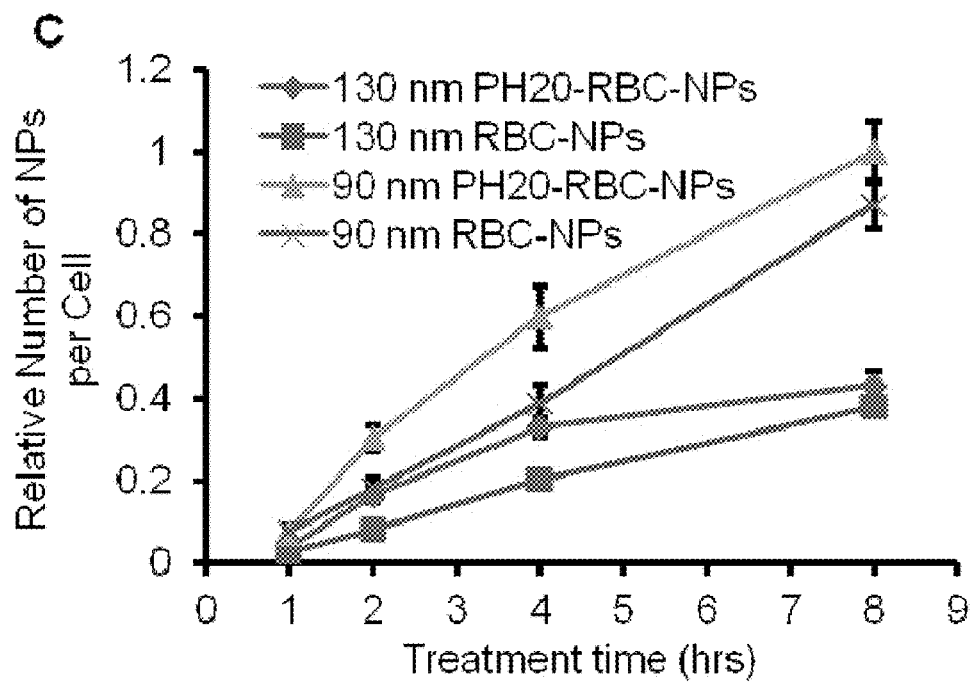
FIG. 3C shows relative number of nanoparticles per PC3 cell after treatment by the nanoparticles of FIG. 3A. Data represent mean±s.d. (n=10).

The diffusion of DiD-labeled NPs in PC3 cells was studied using confocal microscopy and analyzed with ImageJ. The signals were from both internalized NPs and membrane-bound NPs. It was shown that more PH20-RBC-NPs were internalized or bound on PC3 cells than RBC-NPs without conjugated hyaluronidase (FIG. 3A). The enhanced diffusion, which is indicated by the fluorescence intensity difference between PH20-RBC-NPs and RBC-NPs-treated cells over time, gradually disappeared after about 8 h of treatment (FIGS. 3B and 3C). Since the fluorescence intensity signals included both internalized and membrane-bound NPs, the process of NP targeting of PC3 cells can be divided into two steps: matrix penetration and binding on membranes. A cell can only take up a limited amount of NPs. As more and more NPs diffused through the HA extracellular matrix of PC3 cells, the NPs will build up between PC3 cells, though not necessarily be bound on the PC3 cells. The NPs between cells eventually reach saturation, as the enhanced NP diffusion caused by PH20 disappeared after 8 h treatment (FIGS. 3B and 3C). Due to the denser and thicker matrix in tumors, the enhanced diffusion caused by PH20 is expected to be critical for delivery of drugs to tumor cells throughout the tumor. The enhanced diffusion is less significant for smaller sized NPs shown by the percentage of increased fluorescence intensity signals (FIG. 3B). This may be due to the relatively easier diffusion of smaller sized NPs in PC3 cells.

Figure 4A:
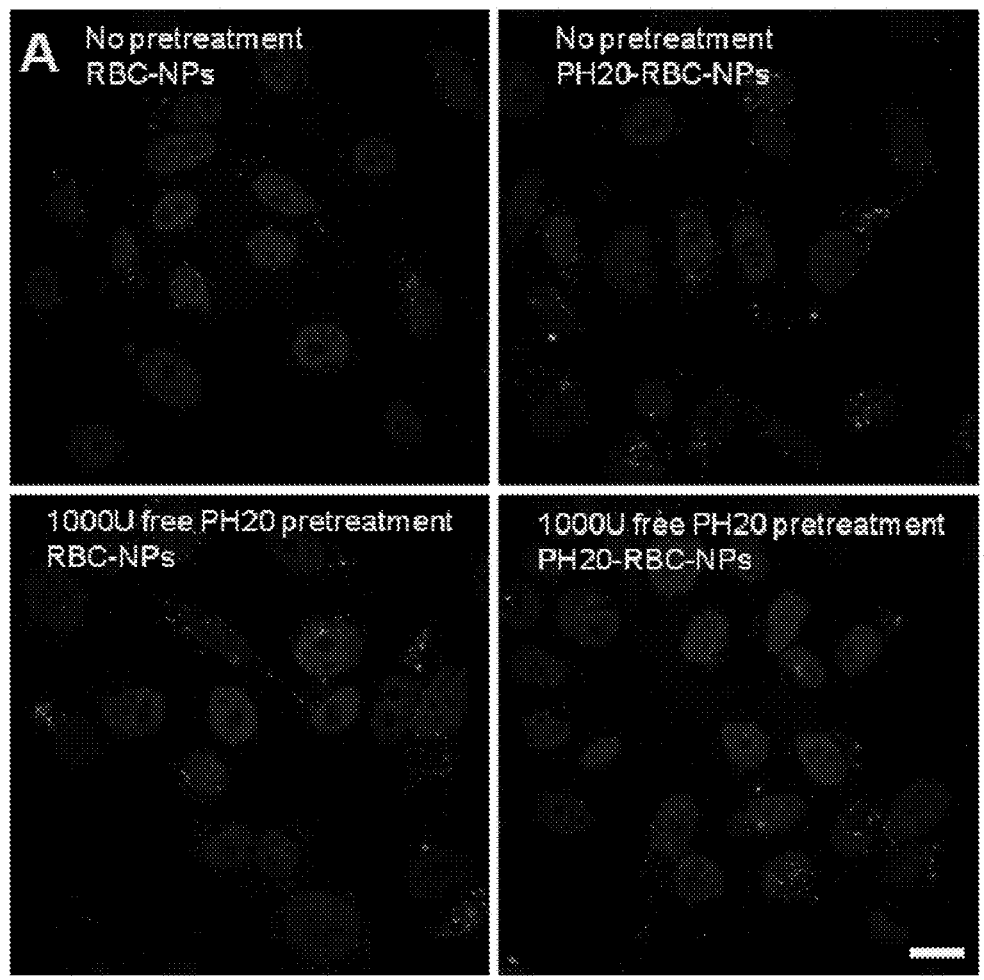
FIG. 4A shows representative confocal microscopy images of PC3 cells treated with DiD-labeled 130 nm PH20-RBC-NPs or RBC-NPs at equal amounts. Some cells were pretreated with 1000 U of hyaluronidase.
Figure 4B:
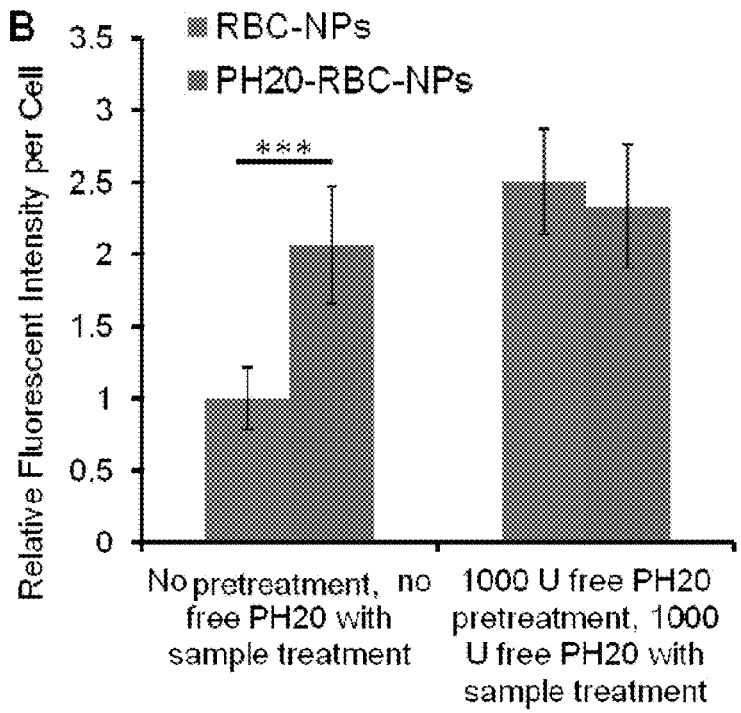
FIG. 4B shows the fluorescence intensity per PC3 cell shown in FIG. 4A after treatment with nanoparticles. Values are mean±s.d. (n=10). *** denotes p<0.001, as analyzed by one-way analysis of variance followed by t-test.

To further confirm that the increased NP internalization and PC3 cell membrane binding is due to enhanced diffusion by conjugated PH20 instead of the possible increased non-specific interaction between NPs and cells due to PH20 modification, PC3 cells were pretreated with 1000 U free PH20 for 2 h before adding NPs and 1000 U free PH20. It has been discovered that incubation with 1000 U of free PH20 for 1 h is sufficient to degrade the pericellular HA layer around PC3 cells. Two hours of pretreatment of PC3 cells with 1000 U of free PH20 should remove the HA layer wrapping PC cells, thus no HA matrix layer existed for the pretreated PC3 cells. Incubation of the pretreated PC3 cells with RBC-NPs and PH20-RBC-NPs showed similar fluorescence intensity. However, the untreated PC3 cells (not treated with free PH20) showed twice the amount of NP internalization and membrane binding by PH20-RBC-NPs compared to same cells incubated with RBC-NPs (FIGS. 4A and 4B). The results demonstrate that PH20 conjugated on RBC-NP surfaces causes the enhanced diffusion by NPs in the PC3 cells.

NPs with encapsulated paclitaxel, with or without conjugated PH20 (PH20-RBC-Ptx-NPs and RBC-Ptx-NPs) were used to test whether the delivery system of the present invention can bring the cytotoxin to PC3 cells. PC3 cells were cultured with RPMI-1640 medium in a 96-well plate. PLGA Ptx-NPs with 125 nm and 85 nm in size were used in the delivery systems. All the freshly prepared NPs samples were added to wells at a concentration of 100 µg/mL PLGA equivalents of NPs in 200 µL per well. Free Ptx stock solution was prepared by dissolving 1 mg/mL of Ptx in DMSO and diluted in DI H$_2$O. The stock Ptx solution was then added to wells as control at 200 µL per well to a final concentration of 1 µg/mL. PC3 cells were treated with PH20-RBC-NPs and RBC-NPs with and without Ptx encapsulated respectively for either 72 h or 2 h. The final Ptx concentrations were 1 µg/mL in the wells when cells were treated with 1% (w/w) Ptx-encapsulating NPs. For the 2 h treatment, the medium containing NP samples were removed after 2 h and the PC3 cells were washed 3 times with PBS before adding fresh medium and continuing incubation for 72 hrs. At the end of the incubation, 20 µL of 5 mg/mL Thiazolyl Blue Tetrazolium Bromide in PBS were added to each well. After incubation for 4 h, the media were carefully removed and 200 µL DMSO was added to each well. The absorbance at 570 nm with a reference at 630 nm was measured for each well after 5 min incubation with the DMSO and 3 min shaking. Relative cell viability was obtained by comparing to untreated cells. All measurements were done in triplicate.

Figure 5A:
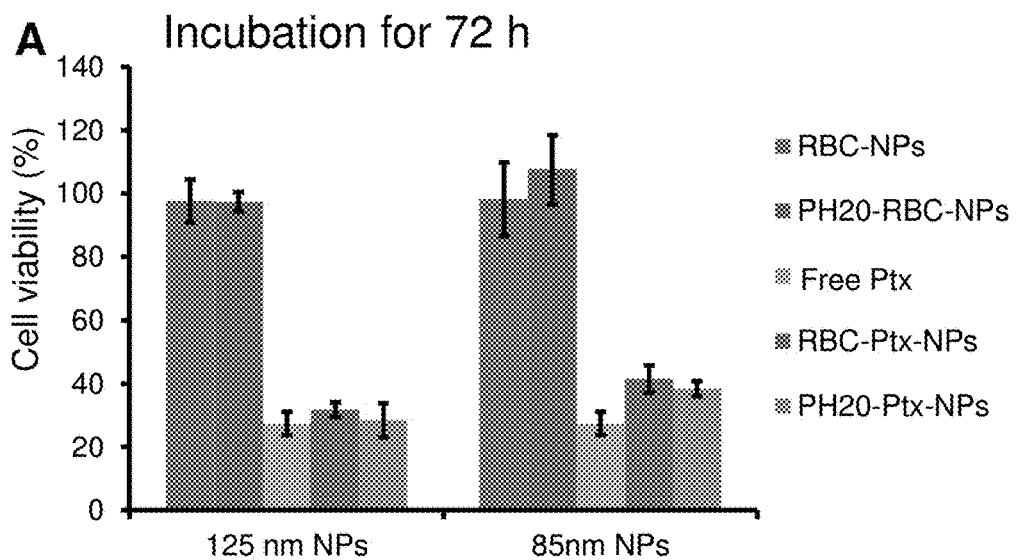
FIG. 5A shows the cell viability of PC3 cells after incubation with different nanoparticles for 72 h. Ptx represents paclitaxel.

After incubation with the NP samples for 72 h, the PC3 cells treated with the delivery system without the Ptx (RBC-NPs and PH20-RBC-NPs) all reached a viability at around 100%, in reference to the untreated cells (FIG. 5A), indicating that the delivery systems themselves are not toxic to the PC3 cells. The viabilities of cells treated with large NPs (125 nm NPs) with Ptx (RBC-Ptx-NPs and PH20-RBC-Ptx-NPs) both reached around 30%, a comparable toxic level equivalent to 1% free Ptx. For the small NPs (85 nm), the delivery system is slightly less effective in delivering the Ptx to the PC3 cells (FIG. 5A). This data is consistent with the above experiment that for a long enough incubation time, PC3 cells are saturated with NP uptake regardless of whether PH20 is used.

Figure 5B:
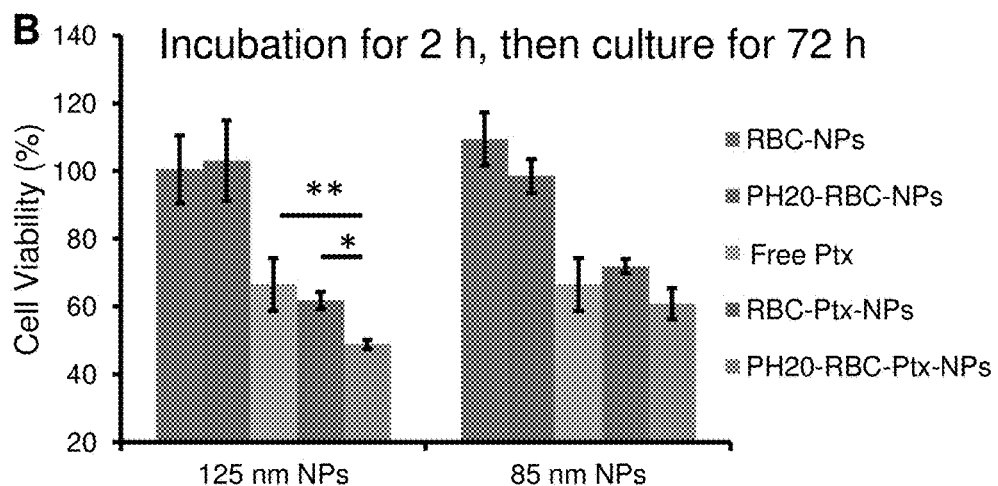
FIG. 5B shows the cell viability of PC3 after incubation with different nanoparticles for 2 h and then culturing in fresh medium for 72 h. Values are mean±s.d., n=3. ** denotes P<0.01, * denotes P<0.05 by one-way analysis of variance followed by t-test.

Next, the incubation time was reduced to 2 h for the same experiment. After 2 h incubation, the NPs were removed and fresh medium was added to continue culturing for 72 h. The overall viabilities of cells treated with Ptx-encapsulating NPs (RBC-Ptx-NPs and PH20-RBC-Ptx-NPs) increased to above 45%. However, the viability of cells treated with 125 nm PH20-RBC-Ptx-NPs was 49%, which is significantly lower than cells treated with RBC-Ptx-NPs and free Ptx (FIG. 5B).

Example 2

The following materials were used in this example. Recombinant human PH20 in pH 6.5, 10 mM sodium phosphate, 150 mM NaCl buffer obtained from Halozyme, Inc. Doxorubicin Hydrochloride salt (DOX) was purchased from BioTang, Inc. Methoxy Poly(ethylene glycol)-b-Poly (lactic-co-glycolic acid) (Mw~5000:20000) (PLGA-PEG) and Poly(lactic-co-glycolic)-b-Poly(ethylene glycol)-Maleimide (Mw~20000-5000) (PLGA-PEG-MAL) were purchased from Polyscitech Inc. Methoxy-Poly(ethylene-glycol)-Thiol (Mw~2000) (PEG-SH) and Methoxy-Poly (ethylene glycol)-Maleimide (Mw~2000) (PEG-MAL) were purchased from Laysan Bio Inc. Mouse Breast cancer cell line, 4T1 was purchased from ATCC Inc. Horse radish peroxidase conjugated Streptavidin (HRP-Streptavidin), o-Phenylenediamine (OPD), 2-Iminothiolane·HCl (Traut's Reagent), N-hydroxysulfosuccinimide (Sulfo-NHS), 1-ethyl-3-(3-dimethylamin-opropyl) carbodiimide (EDC) and (biotinyl)hydrazide (Biotin hydrazide) were purchased from Thermo Scientific. DiD oil (DilC18(5) oil) was a product of Life Technologies. Additional salts, solvents and buffers were purchased from Fisher Scientific.

Nanoparticles were prepared according to a nano-precipitation method. Briefly, the polymers PLGA-PEG and PLGA-PEG-MAL (4:1 w/w) were dissolved in acetonitrile (ACN) at a polymer concentration of 5 mg/ml. The fluorescent dye, DiD, was also dissolved in acetonitrile (ACN) and added at 0.2 wt % to the polymer solution. DOX hydrochloride salt was first dissolved in methanol at a concentration of 10 mg/mL and reacted with a 5-fold excess of triethylamine (TEA) at room temperature for 24 h. The resulting mixture was then diluted in ACN and added into the polymer solution at 10% (w/w). The final polymer solution in acetonitrile was added dropwise into PBS (2:5 v/v) under stirring and stirring was continued in a hood for 3 hours before leaving the mixture in a vacuum overnight to produce the nanoparticles.

The amount of DOX encapsulated in the nanoparticles was quantified by the fluorescence intensity of DOX (Excitation at a wavelength of 480 nm and Emission at a wavelength of 595 nm) using TECAN by dissolving 20 µL of sample into 180 µL DMSO. Loading yield was calculated using the following equation:

$$\text{Loading Yield} = \frac{\text{Mass of DOX encapsulated in NP}}{\text{Mass of Polymer in NP}}$$

The nanoparticles produced after this step were PLGA-PEG-NPs (without DOX) and DOX-PLGA-PEG-NPs (with encapsulated DOX).

PH20 (a recombinant HAase) was then conjugated onto the surface of the produced nanoparticles. PH20 was first thiolated using Traut's reagent. A 5-fold excess of Traut's reagent in PBS was added into 1 mg/mL PH20 solution in PBS and reacted for 1 h at room temperature under constant stirring to produce thiolated PH20. The thiolated PH20 was purified by filtering through a desalting column (Thermo Scientific).

To conjugate the thiolated PH20 to the nanoparticles, the thiolated PH20 was added into the previously produced nanoparticles in PBS at a concentration of 100 µg/mL. After 2 h under stirring, PEG-maleimide (5-fold excess) and PEG-thiol (10-fold excess) were subsequently added to the nanoparticles and PH20 mixture to produce the second layer of PEG on the nanoparticle surfaces. The unreacted PEG-thiol and PH20 were removed via overnight dialysis at 4° C.

Figure 10A:
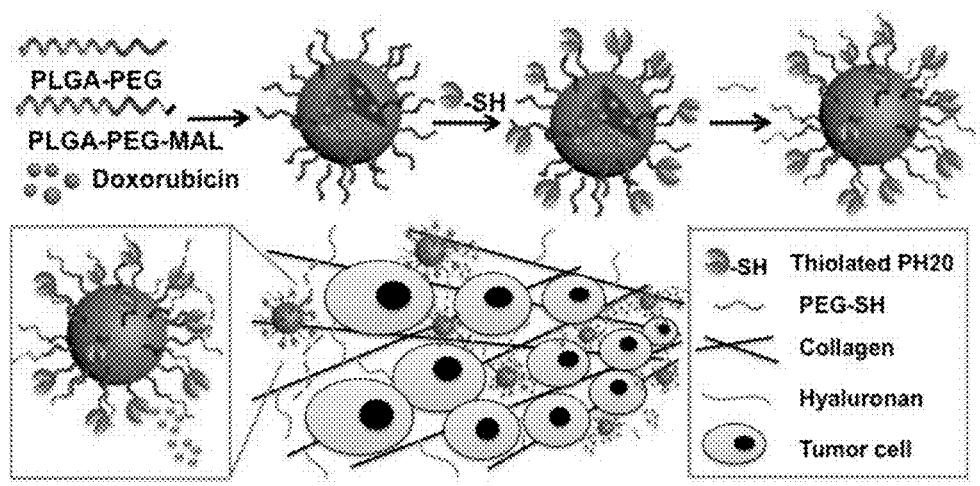
FIG. 10A is a schematic illustration of a fabrication process for producing PH20-conjugated poly(lactic-co-glycolic acid)-co-polyethylene glycol nanoparticles (PLGA-PEG-NP) and also depicts penetration of the PH20-conjugated PLGA-PEG-NP into tumors via degradation of hyaluronic acid as described in Example 2. Without specification, PLGA-PEG-NPs in the experimental description refer to nanoparticles that are made with 80% of PLGA-PEG polymer and 20% of PLGA-PEG-Maleimide polymer and conjugated with PEG-thiol polymer through maleimide-thiol reaction after nanoparticle formation.

The nanoparticles produced after this step were PLGA-PEG-PH20-NPs and DOX-PLGA-PEG-PH20-NPs, both with conjugated PH20 and a second layer of PEG (FIG. 10A).

The nanoparticles after each step of the above process may be purified to produce nanoparticles with or without the conjugated PH20/second PEG layer, and/or with or without the encapsulated DOX, which were ready to be used in cell cultures or animals for further testing. The nanoparticles were purified via dialysis against saline overnight through 50-nm membranes at 4° C. The nanoparticles were concentrated through centrifugal filters (Amicon Ultracel 30K) and passed through 0.2 µm syringe membrane before further use.

Example 3

Figure 10B:
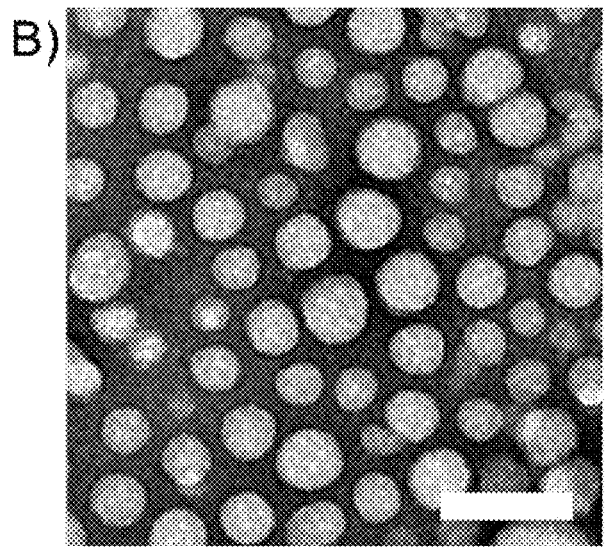
FIG. 10B is a transmission electron microscopy (TEM) image of the PH20-conjugated PLGA-PEG-NPs produced in Example 2 (The Scale bar is 100 nm).

Sizes and zeta potentials of the nanoparticles produced in Example 2 were detected by dynamic light scattering (DLS, Zetasizer Nano ZS90). To image nanoparticles with transmission electron microscopy (TEM), a carbon coated grid was cleaned by plasma and 10 µL of nanoparticles with a concentration of 0.2 mg/mL was added. The grid was then rinsed with DI water 3 times. To stain the nanoparticles, 5 µL of 2% uranyl acetate water solution was dropped on the grid and filter paper was used to absorb the solution instantly. This step was repeated 3 times and the nanoparticles were observed using a JEOL JEM2100 at 200 KV (FIG. 10B).

The size of the nanoparticles was measured by a size exclusion assay. 0.3 mL of 10 mg/mL PLGA-PEG-PH20-NP in PBS was passed through a column packed over a length of 25 cm with S-400 beads (Sephacryl™, GE Healthcare). PBS was used to elute the sample through the column and 1 mL per eluting fragment was collected from the addition of sample and up to 50 fragments. Fluorescence for each fragment was detected via TECAN and the activity of PH20 on nanoparticles in each fragment was detected via the PH20 activity assay.

Figure 15A:
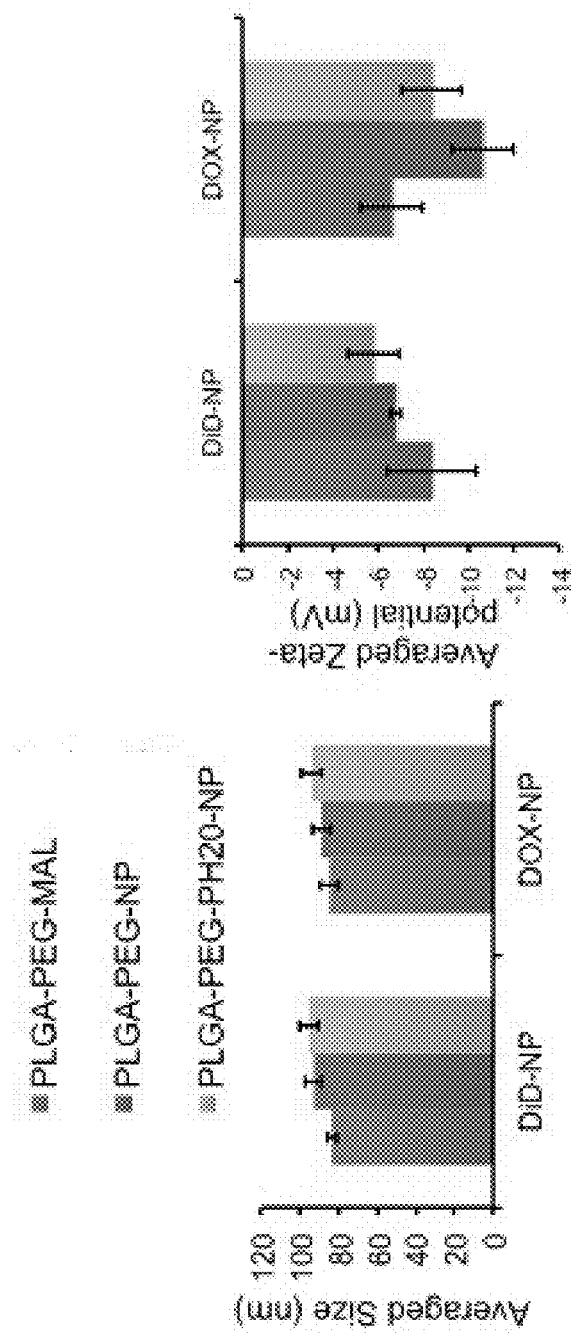
FIG. 15A shows the size and zeta-potential of the DiD-labeled or the DOX-encapsulated nanoparticles produced in Example 2 of the application. The nanoparticle sizes were measured by dynamic light scattering (DLS, Zetasizer Nano ZS90).

Transmission Electron Microscopy (TEM) images of the PLGA-PEG-PH20-NPs showed an averaged size of around 80 nm (FIG. 10B), while the size measured with Dynamic Light Scattering (DLS) was around 100 nm (FIG. 15A), likely due to the dehydration of PEG layers during the microscopic procedure.

Example 4

The HAase activity of the nanoparticles produced in Example 2 was measured by a modified microtiter-based assay. Briefly, HA was dissolved in 0.1 M 2-(N-morpholino) ethanesulfonic acid (Mes) pH 5.0 buffer at a concentration of 1 mg/mL by stirring overnight at 4° C. Sulfo-NHS was then added to the HA solution to a final concentration of 0.184 mg/mL. Biotin hydrazide was dissolved in DMSO as a stock solution of 100 mM and diluted 100 times in the HA solution. EDC was prepared as a 100 mM stock solution in DI $H_2O$ and then added to the HA-biotin solution at a final concentration of 30 mM. This solution was stirred overnight at 4° C. before stopping the reaction by the addition of 4 M guanidine-HCl. Unlinked biotin and EDC were removed by dialysis against DI $H_2O$ overnight.

To coat the biotinylated HA (bHA) on the plates (96-well COVALINK-NH microtiter plate, Thermo Fisher Scientific.), the bHA solution was first mixed with sulfo-NHS at a concentration of 0.2 mg/mL bHA and 0.184 mg/mL sulfo-NHS. 50 µL of the resulting solution was pipetted into each well before adding another 50 µL of EDC at a concentration of 0.123 mg/mL in DI $H_2O$. The plates were incubated overnight at 4° C. After coating (covalent immobilization) of bHA on the microtiter plates, the coupling solution was removed and the plate was washed three times with PBS containing 2 M NaCl and 50 mM $MgSO_4$.

The plate was equilibrated with PBS buffer for 1 h before the assay. A standard activity curve of free PH20 in PBS was generated by diluting 1 mg/mL PH20 solution with an original activity of 116000 U/mg to a series of solutions with PH20 activity from 1 U/mL to 1000 U/mL. The nanoparticle samples were diluted five times in PBS before being assayed at 100 µL/well in triplicate. After 50 min of incubation at 37° C., the reaction was terminated by adding 200 µL 6M Guanidine-HCl per well followed by three washes with 300 µL/well of PBS, 2 M NaCl, 50 mM $MgSO_4$, 0.05% Tween 20. HRP-streptavidin at a concentration of 0.125 µg/mL in PBS containing 0.1% Tween 20 was used to probe remaining bHA. This solution was added at an amount of 100 µL/well and incubated for 30 min at room temperature.

The plate was then washed five times before adding 100 µL/well of the OPD substrate. The OPD substrate was prepared by dissolving one 5 mg-tablet of OPD in 5 mL of 0.1 M citrate-$PO_4$ buffer, pH=5, with 3.75 µL of 30% $H_2O_2$. The plate was incubated in the dark for 5 min before quenching with 50 µL/well of 4 M $H_2SO_4$ solution. Absorbance for each well was read at 492 nm (TECAN, Infinite M200) and the PH20 activity of each sample was determined by comparing with a standard curve.

Figure 10C:
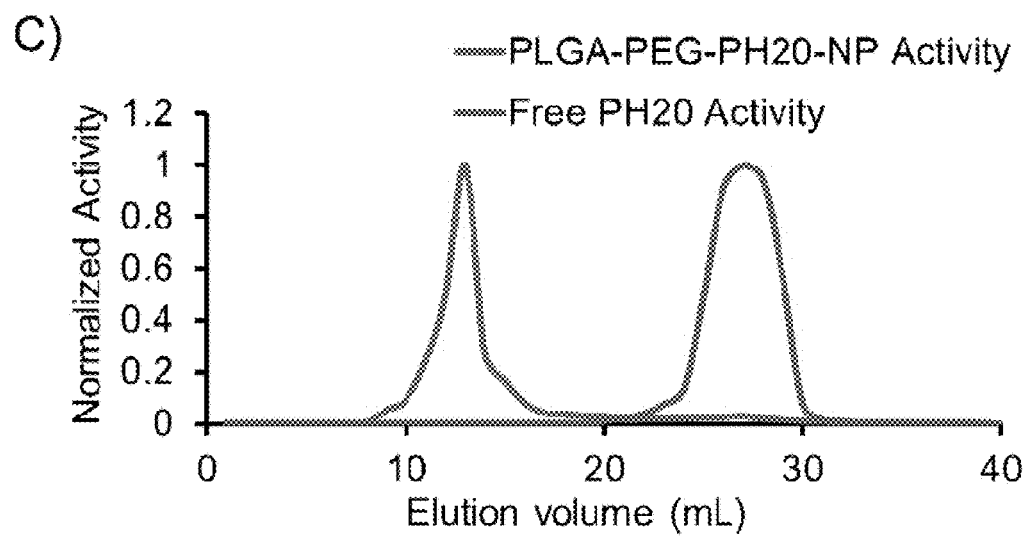
FIG. 10C shows results of a size exclusion assay of the PH20-conjugated PLGA-PEG-NPs and free PH20. The elution volume for the PH20-conjugated PLGA-PEG-NPs was smaller than the elution volume of free PH20. This indicates successful conjugation of PH20 to the nanoparticles and removal of free PH20 after conjugation.
Figure 15B:
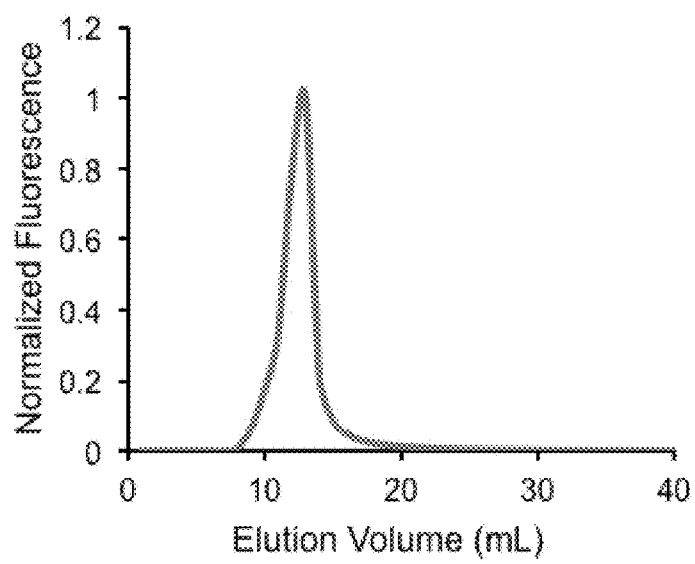
FIG. 15B is a fluorescence profile produced by a size exclusion assay of DiD-labeled PLGA-PEG-PH20-NPs.
Figure 15C:
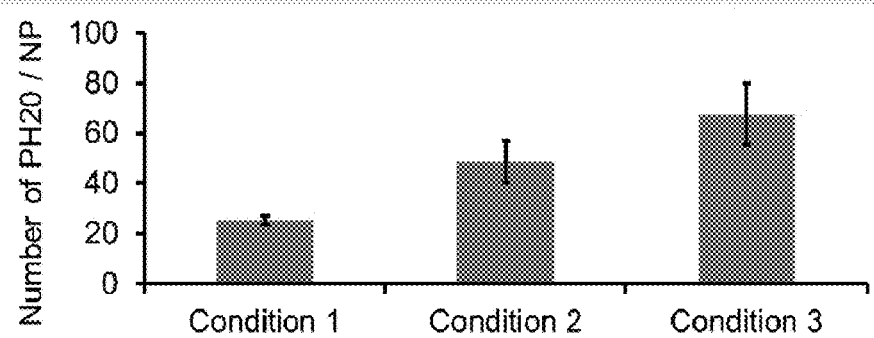
FIG. 15C shows a quantitative measure of the effective number of PH20 conjugated on PLGA-PEG-NPs using different conjugation conditions. Values indicate mean±standard deviation (n=3).

Enzymatic activity of eluate from the size exclusion assay of Example 3 was quantified by HA degradation as described above. The activity of PLGA-PEG-PH20-NPs appeared at an elution volume smaller than that of free PH20 (FIG. 10C). The characteristic elution volume of nanoparticles was also confirmed by measuring the fluorescent signal of DiD labeled nanoparticles in eluate (FIG. 15B), indicating successful conjugation of PH20 on nanoparticles and removal of free PH20. The amount of PH20 on the nanoparticles can be adjusted and controlled by adjusting PH20 and nanoparticle concentrations in the reaction mixture (FIG. 15C). Unless otherwise specified, the number of effective PH20 molecules/nanoparticle was around 48, which equals to 500 U activity per mg of nanoparticles.

Example 5

ECM mimicking gels containing collagen and HA were prepared. In brief, the ECM mimicking gels were prepared by mixing the following components in order on ice: 48 µL of 10×PBS, 12.8 µL of 1N NaOH, 24.3 µL of DI water, 160 µL of 5 mg/mL HA (MW=1.5~2.0×10$^6$) in 2×PBS and 555 µL of 9.37 mg/mL rat tail collagen type I (Corning, Bedford, Mass.). The final concentration in the mixture of collagen was 6.5 mg/mL and the final concentration of HA was 1 mg/mL in the mixture. The mixture was thoroughly vortexed and vacuumed on ice to remove bubbles before the addition of 60 µL solution into each capillary tube (0.4×4.00 mm ID, Vitrocom, Mountain Lakes, N.J.). The tubes were then incubated overnight at 37° C.

In the diffusion tests, 10 µL of equalized 1 mg/mL of PLGA-PEG-NP, 1 mg/mL of PLGA-PEG-NP and 500 U/ml free PH20 or 1 mg/mL PLGA-PEG-PH20-NP solution, in which the PH20 on nanoparticles have the same amount of activity as 500 U/mL, were slowly added on the surface of the ECM mimicking gel. All the nanoparticles were labeled with DiD during fabrication. The tube was then sealed and left at 37° C. for 1.5 h. The gels were imaged by using a confocal laser scanning microscope. Image analysis was performed using ImageJ. Diffusion profiles of relative intensity (C) and the diffusion distance (x) for the nanoparticles were fitted to the following one-dimensional diffusion model to obtain the diffusion coefficient D in the ECM mimicking gel:

$$C(x, t) = A \times \mathrm{erfc}\left(\frac{x}{\sqrt{2tD}}\right) + B$$

where erfc is the complementary error function and A and B are the constants for the function. The nonlinear curve fitting was performed by using the fminsearch function in Matlab.

Figure 10D:
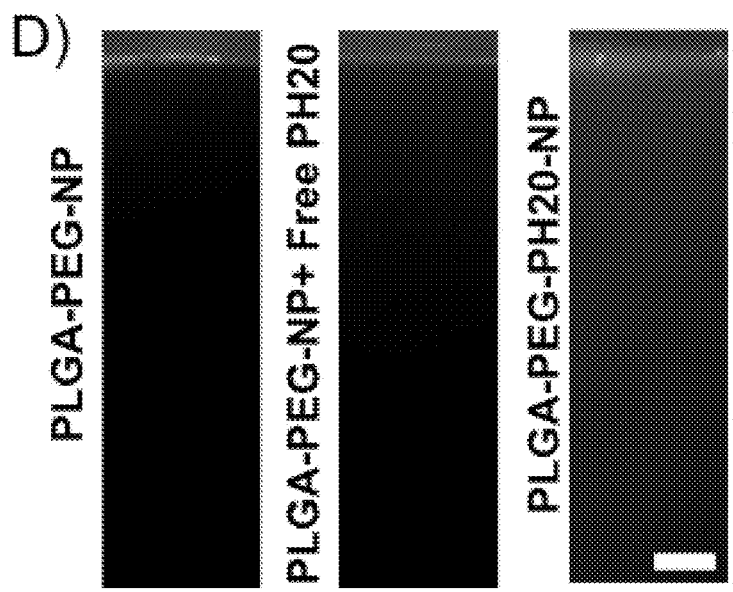
FIG. 10D shows diffusion in gels composed of collagen and hyaluronic acid (which mimics the ECM of tumors) by PLGA-PEG-NPs alone, PLGA-PEG-NPs plus free PH20, and PH20-conjugated PLGA-PEG-NPs (The scale bar is 150 µm). The gels were prepared with 6.5 mg/mL of rat collagen I and 1 mg/mL of hyaluronic acid (HA) in capillary tubes. For each test, 10 µL of 1 mg/mL of DiD-labeled nanoparticles with or without 500 U/mL of PH20 activity (as indicated in the figure) was added on the top of the gels and incubated at 37° C. for 1.5 h before being imaged with a confocal laser scanning microscope. The images of FIG. 10D were analyzed via ImageJ. The Diffusion coefficient was fitted by MATLAB to a one-dimensional diffusion model.
Figure 10E:
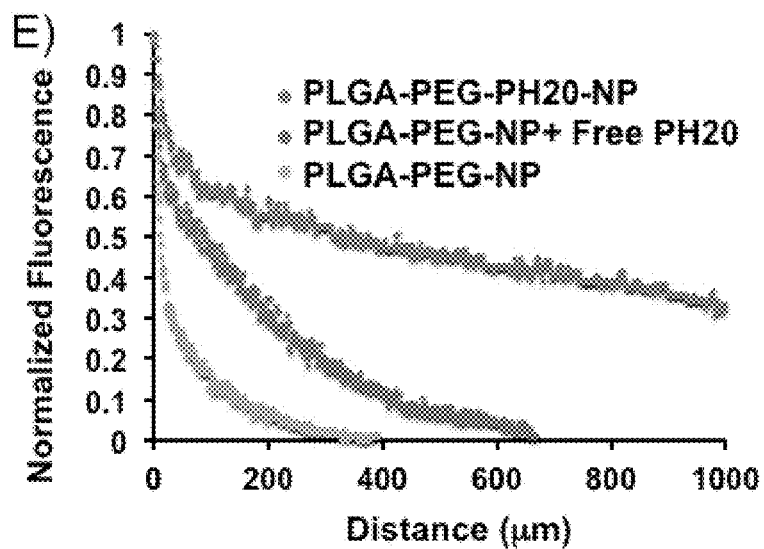
FIG. 10E is a plot showing normalized nanoparticle fluorescence versus diffusion distance in the ECM mimicking gel, as shown in FIG. 10D. The plots are fitted to one-dimension diffusion model with diffusion coefficients of $1.66 \times 10^{-7}$ $cm^2 \cdot s^{-1}$, $7.17 \times 10^{-8}$ $cm^2 \cdot s^{-1}$ and $1.11 \times 10^{-8}$ $cm^2 \cdot s^{-1}$ from top to bottom respectively.

The nanoparticles produced in Example 2 were fluorescently labeled by encapsulating 0.2 wt % of 1,1'-dioctadecyl-3,3,3',3'-tetramethylindodicarboxy-amine Perchlorate (DiD), and then loaded onto the gels. PLGA-PEG-NPs alone could barely diffuse into the physiologically relevant dense gels likely because of the small pore size inside the gels. PH20 (free or conjugated) degraded HA in the gels, enabling NP diffusion (FIG. 10D). The diffusion profiles were fitted to the one-dimensional diffusion model to calculate the diffusion coefficients (FIG. 10E). The addition of free PH20 increased the diffusion coefficient of nanoparticles from $1.09\pm0.51\times10^{-8}$ cm$^2\cdot$s$^{-1}$ to $7.33\pm0.25\times10^{-8}$ cm$^2\cdot$s$^{-1}$, in comparison with nanoparticles with no PH20 activity. A further more than 1-fold increase was observed for PLGA-PEG-PH20-NPs, in comparison with PLGA-PEG-NPs with the same amount of free PH20 activity. The PLGA-PEG-PH20-NPs provided a diffusion coefficient of $1.72\pm0.33\times10^{-7}$ cm$^2\cdot$s$^{-1}$ in the gel. Thus, PH20 conjugated to the nanoparticles was demonstrated to be much more efficient than free PH20 for facilitating nanoparticle diffusion in the gels.

Example 6

The nanoparticles produced in Example 2 were tested on tumor cell line 4T1, which synthesizes HA and forms a layer of HA matrix around the cells. 4T1 cells were maintained in a RPMI-1640 medium (ATCC) containing 10% fetal bovine serum in 5% $CO_2$ in an incubator at 37° C. 4T1 cells were cultured on round glass coverslips in a 12-well plate for one day to reach 70% confluency before treatment with the nanoparticles. DiD-labeled PLGA-PEG-NPs (no PH20 activity) and DiD-labeled PLGA-PEG-PH20-NPs (conjugated 10 U/mL PH20 activity) were used for this test. The amount of nanoparticles in all samples was equalized via fluorescence intensity. Nanoparticle solutions were diluted in cell culture media 5 times before adding at 1 mL/well and incubated at 37° C. with the 4T1 cells in the well for several time points (for 2, 4, or 6 h) for the kinetic study of nanoparticle internalization and 2 h for the rest of studies.

The 4T1 cells were then washed and fixed and observed under a confocal microscope (Olympus IX81, 60×, C.A.=80 µm) with 405 nm and 635 nm lasers for DAPI and DiD respectively. The HV and gain were set high enough to avoid saturation and the % off was set low enough to include all signals against background. Ten images for each sample were taken at random locations and focused at the focal plane where the largest nuclei showed. The total fluorescence intensity of DiD was quantified via Image J and averaged by the number of cells.

Figure 11A:
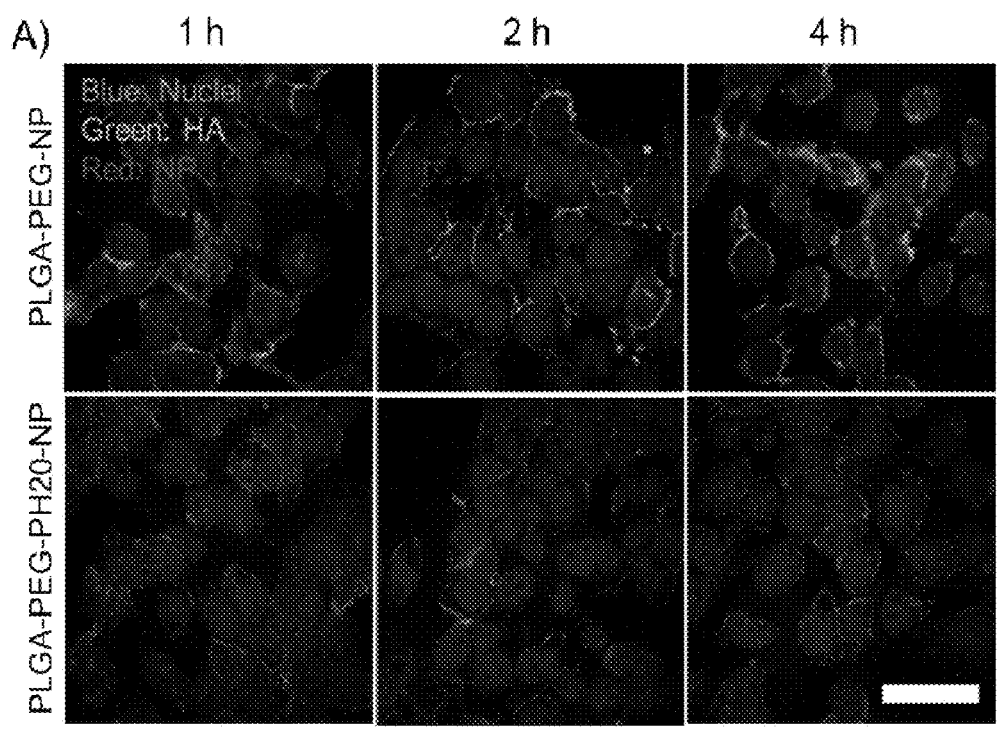
FIG. 11A shows confocal microscopy images of 4T1 cells treated with 0.02 mg/mL of either PLGA-PEG-NPs (no PH20 activity) or PH20-conjugated PLGA-PEG-NPs with an activity of 10 U/mL for 1 h, 2 h and 4 h, respectively. Hyaluronic acid was stained in green and nuclei of the 4T1 cells were stained in blue. DiD-labeled nanoparticles were in red. The observed nanoparticle signal was from internalized nanoparticles and might also include NPs bound on cell surfaces (The scale bar is 50 µm).
Figure 11B:
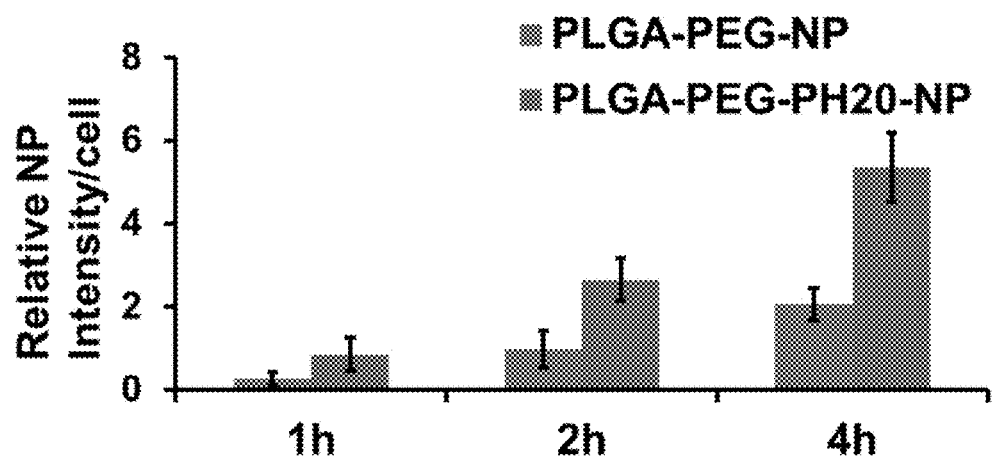
FIG. 11B shows results of a quantitative analysis of nanoparticle internalization and FIG. 11C shows results of HA fluorescence intensity, both per cell of 4T1 cells treated for 1 h, 2 h and 4 h, respectively, as described in FIG. 11A. Values indicate mean±standard deviation (n=10).
Figure 11C:
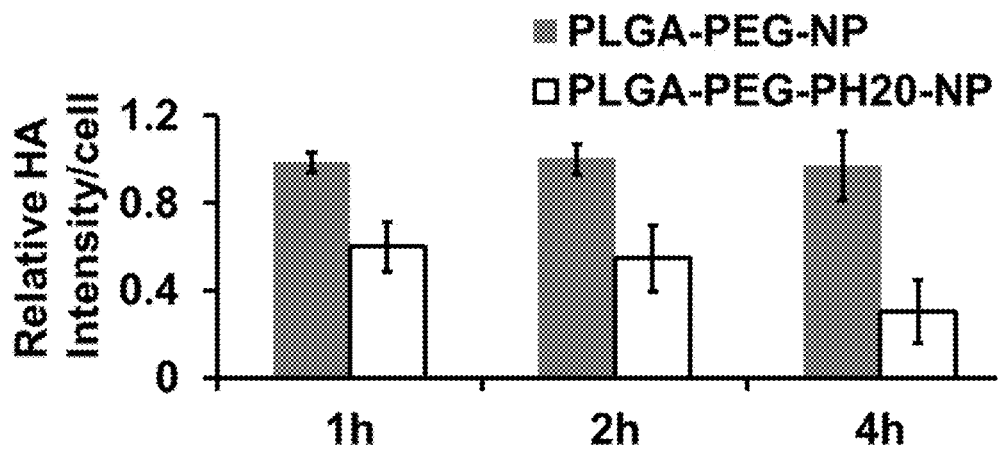

Partial degradation or disruption of the ECM around the 4T1 cells enhanced internalization of nanoparticles by cells. The internalization signals were from internalized nanoparticles and might also include membrane-bound nanoparticles. It was observed in this example that PH20 digestion enhanced nanoparticle internalization by 4T1 cells (FIGS. 11A-11B). Although PLGA-PEG-PH20-NPs degraded a significant amount of pericellular HA (FIGS. 11A and 11C), complete removal of the HA layer around the 4T1 cells was unnecessary for the enhanced internalization as the enhancement started at an early time point when the majority of HA still remained intact.

Figure 11D:
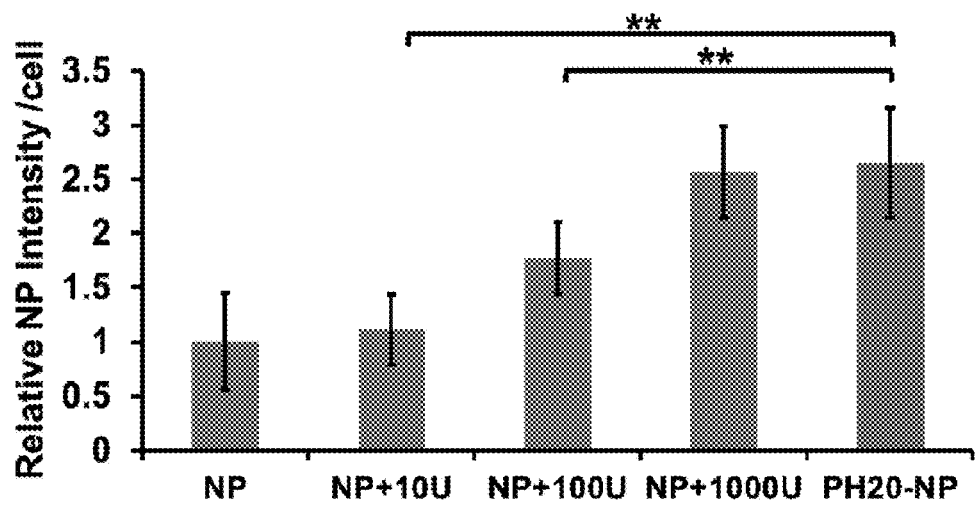
FIG. 11D shows a quantitative analysis of nanoparticle internalization and FIG. 11E shows HA fluorescence intensity, both per cell for 4T1 cells treated with 0.02 mg/mL of PLGA-PEG-NPs supplemented with free PH20 at 0 U/mL, 10 U/mL, 100 U/mL and 1000 U/mL or treated with PH20-conjugated nanoparticles (PLGA-PEG-PH20-NPs) with 10 U/mL of PH20 activity for 2 h. Values indicate mean±standard deviation. (n=10). Analysis of variance (ANOVA) was performed for both groups. "**" indicates a statistical significance of p<0.01.
Figure 11E:
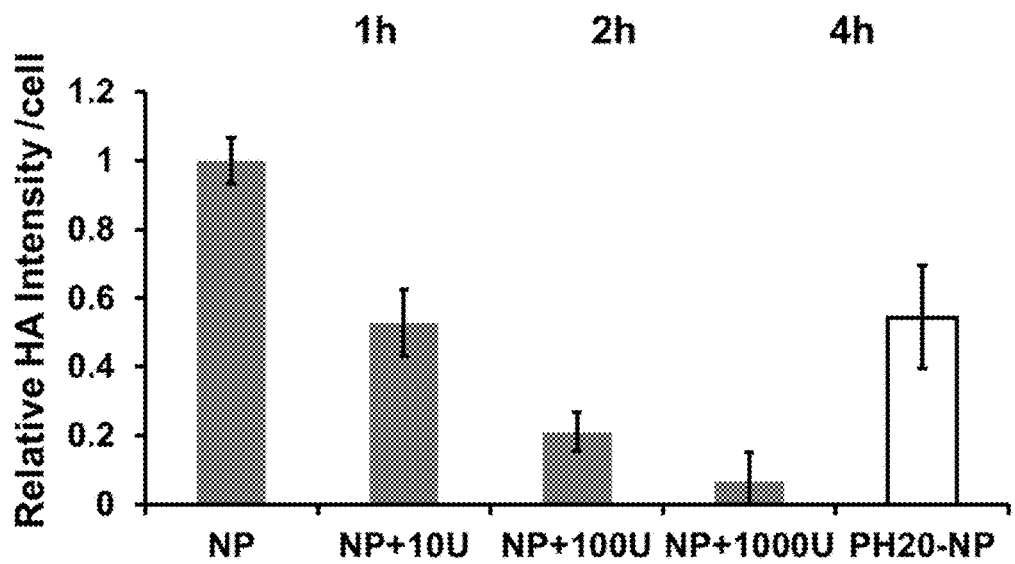

When 1 mL of PLGA-PEG-PH20-NPs with 10 U activity were compared to NPs mixed with 10 U, 100 U, or 1000 U of free PH20, the PLGA-PEG-PH20-NPs again showed superior efficiency in internalization. The internalization of PLGA-PEG-PH20-NPs by 4T1 cells were over 2 times higher than PLGA-PEG-NPs mixed with 10 U free PH20 (FIG. 11D). However, the HA degradation was almost the same in both cases (FIG. 11E). PLGA-PEG-NPs mixed with 100 U of free PH20, although they degraded more overall HA, showed less nanoparticle internalization than PLGA-PEG-PH20-NPs with only 10 U of PH20 activity (FIGS. 11D and 11E). Since nanoparticles need to pass through the pericellular HA matrix prior to being internalized by the 4T1 cells, these observations suggest that degrading HA on the diffusion path of the nanoparticles was more efficient in facilitating nanoparticle penetration than random HA degradation by free PEGPH20. This data also agreed with the results of nanoparticle diffusion in ECM mimicking gels.

The RBC exclusion assay is another way of demonstrating disrupting the pericellular ECM of 4T1 cells by PH20 activity. RBCs were collected fresh from mice and washed three times with PBS before being resuspended in 2% formaldehyde in PBS for fixation of the RBCs overnight at room temperature. 4T1 cells were cultured in a 12-well plate at 5000 cells/well two days before the assay. The cell culture medium was changed to 1000 U/mL of PH20 in medium for PH20 pretreated wells and regular medium for blank controls. After 2 h incubation at 37° C., all the wells were washed with PBS and 0.5 mL fixed RBCs solution (5×10$^8$ RBCs/mL in medium) was added into each well with the 4T1 cells. The plate was allowed to stand for 20 mins and then phase contrast images were taken using optical microscopy. The areas of exclusion (no RBCs) were quantified through ImageJ. RBCs cannot penetrate a normal ECM. However, the RBCs can penetrate the ECM and the areas of exclusion will decrease if the ECM is digested or disrupted by PH20 (free or conjugated).

Figure 16A:
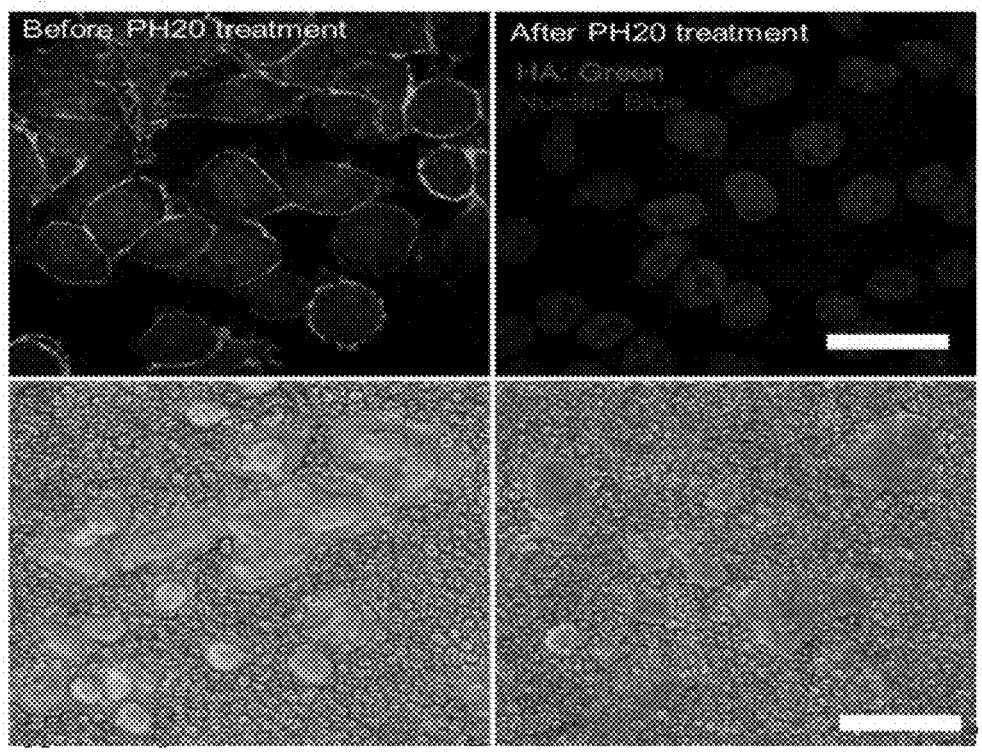
FIG. 16A shows images of HA stain around 4T1 cells (top panels) and images of RBC exclusion assay of 4T1 cells (bottom panels) before and after free PH20 treatment, indicating the existence of pericellular HA layer around the cultured 4T1 cells and the enzymatic effect of PH20 in removing the HA layer. Green: HA; Blue: Nuclei. (The scale bar is 50 μm).
Figure 16B:
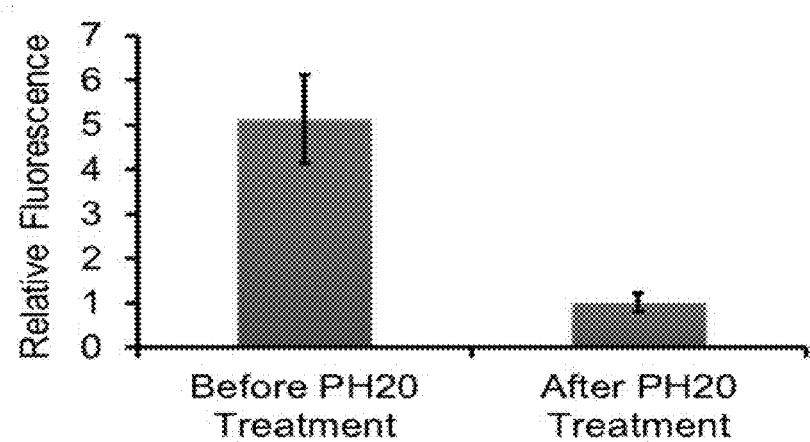
FIG. 16B shows the relative fluorescence intensity of HA per 4T1 cell before and after 1000 U of free PH20 treatment at 37° C. for 2 hr, as described in FIG. 16A. Values indicate mean±standard deviation (n=10). Images were analyzed using ImageJ.
Figure 16C:
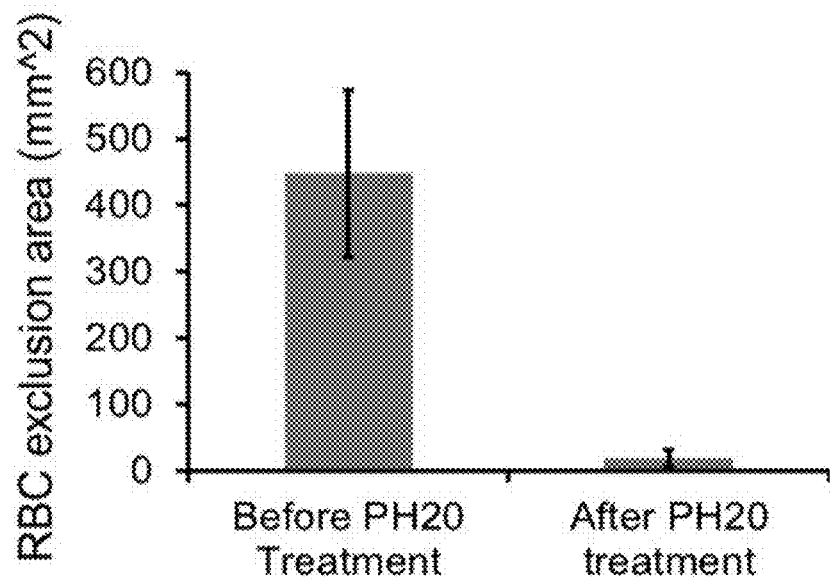
FIG. 16C shows the size of an RBC exclusion area per cell before and after PH20 treatment, as described in FIG. 16A. Values indicate mean±standard deviation (n=10). Images were analyzed by ImageJ.

The pericellular HA matrix of 4T1 cells was shown by the fluorescent staining of HA (FIG. 16A, top panels). In the RBC exclusion assay, the HA matrix prevented RBCs from accessing 4T1 cells (FIG. 16A, bottom panels). After PH20 treatment, the amount of HA around the cells was reduced to a low level that could no longer block RBCs. There was still a trace amount of HA in the fluorescent staining possibly because PH20 cannot degrade HA chains shorter than 6 units.

Figure 17A:
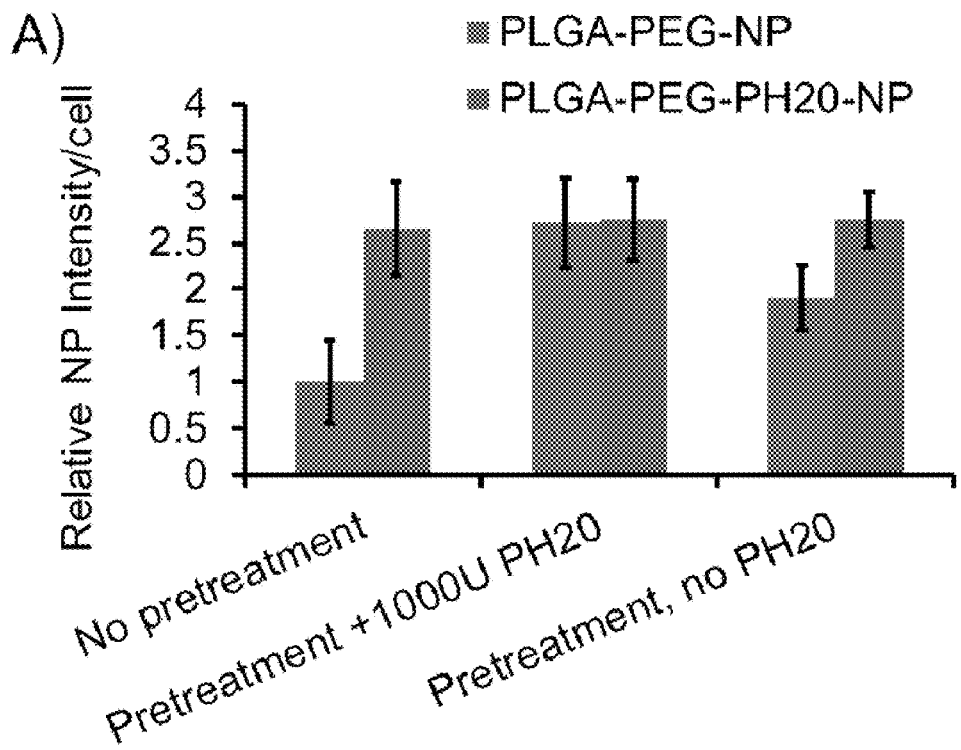
FIG. 17A shows a quantitative analysis of nanoparticle intensity in 4T1 cells in three parallel experiments. Pretreatment means that 4T1 cells were pretreated with 3000 U of free PH20 at 37° C. for 2 h in 1 mL of medium to ensure a complete depletion of HA around the cells. The cells were then treated with either 0.02 mg/mL of PLGA-PEG-NP (no PH20 activity) or PLGA-PEG-PH20-NPs with 10 U/mL of conjugated PH20 activity. Values indicate mean±standard deviation (n=10).
Figure 17B:
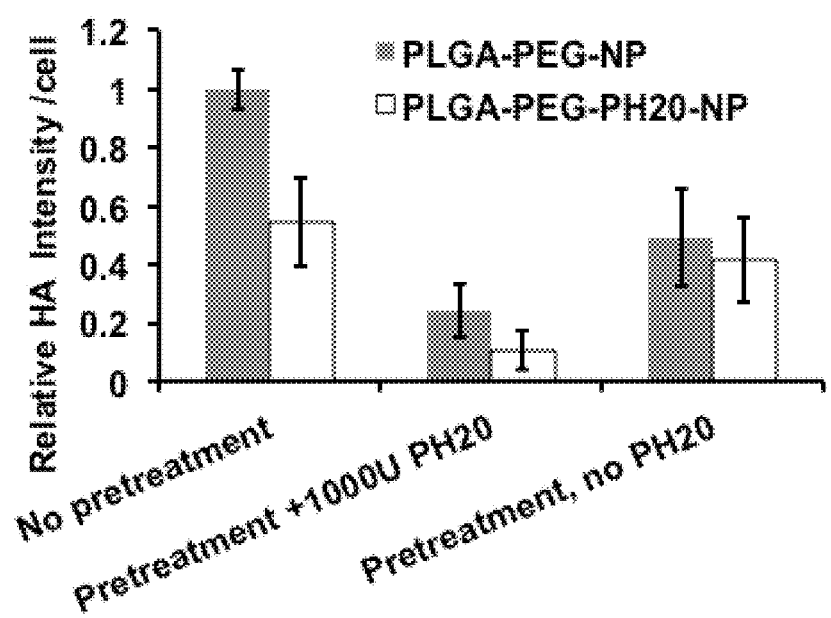
FIG. 17B shows fluorescence intensities of HA in three parallel experiments described in FIG. 17A.

To further confirm that the increased nanoparticle internalization was due to enhanced diffusion instead of the possible increased non-specific interaction between nanoparticles and 4T1 cells after PH20 digestion of HA in ECM, 4T1 cells were pretreated with 3000 U of free PH20 for 2 h before adding nanoparticles with or without an additional 1000 U of free PH20 (FIGS. 17A-17B). It was observed that incubation with 3000 U of free PH20 for 1 h was sufficient to degrade the pericellular HA layer around 4T1 cells. Two hours of pretreatment and maintenance of 1000 U of free PH20 in the system excluded the effects of the HA layer. The removal of the HA matrix significantly increased the internalization of PLGA-PEG-NPs by 4T1s, indicating the HA matrix was truly a barrier for nanoparticles to access 4T1 cells. With the HA matrix layer removed by the pretreatment, cells treated with PLGA-PEG-NPs and PLGA-PEG-PH20-NPs showed similar fluorescence intensities as the nanoparticles and a similar low level of HA (FIGS. 17A-17B).

To further investigate the possibility of PH20-mediated binding to the 4T1 cells, cells were treated with nanoparticles alone after pretreatment with 3000 U of free PH20. The amount of internalized PLGA-PEG-NPs increased, but was still lower than that of PLGA-PEG-PH20-NPs, likely due to the partial formation of an HA layer around the cells within 2 h after the free PH20 activity was removed (which can synthesize HA to form the HA layer, FIG. 17B). Thus, the increased nanoparticle internalization was mainly, if not totally, because of the enhanced nanoparticle diffusion via HA degradation caused by the conjugated PH20.

Figure 17C:
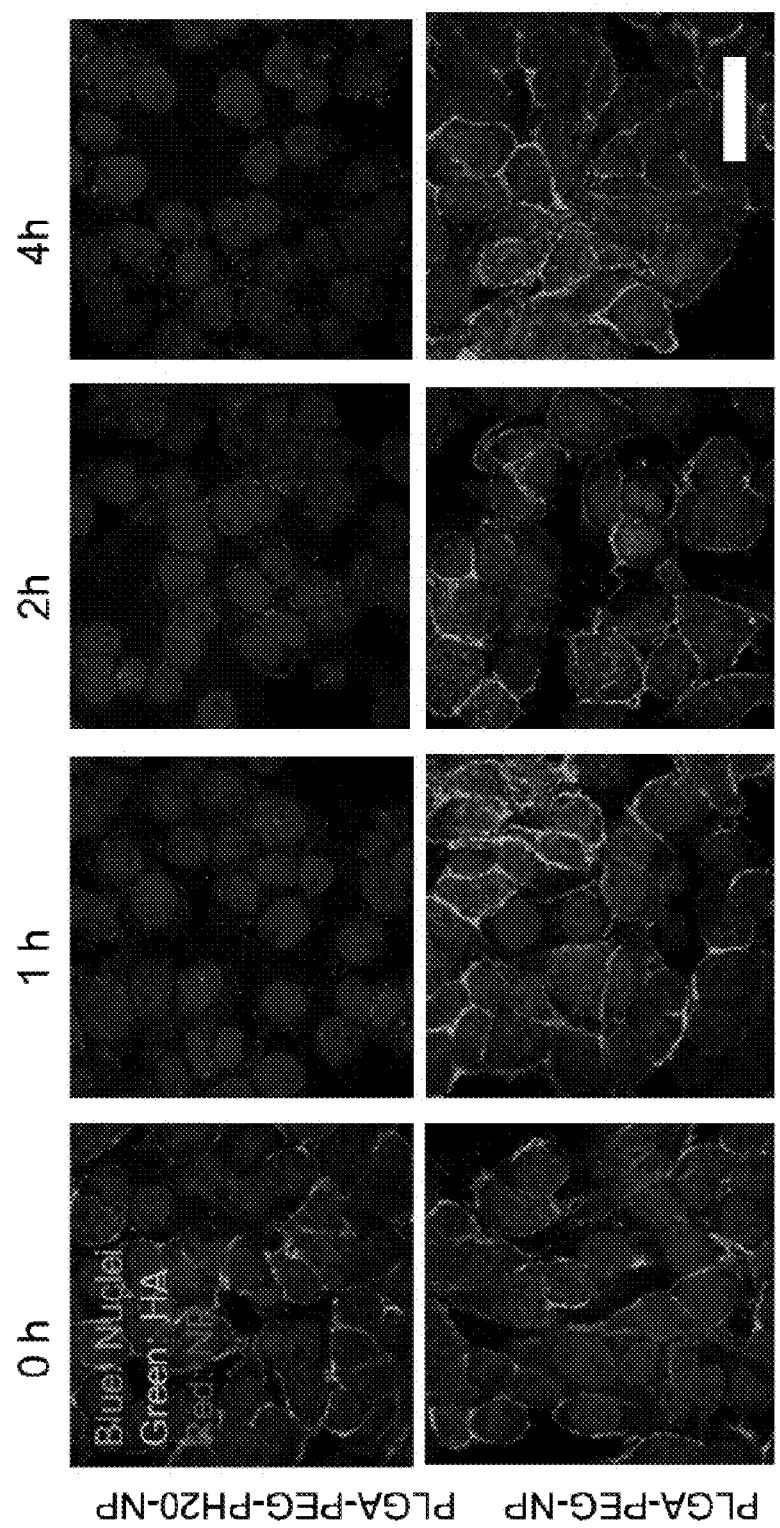
FIG. 17C shows confocal microscopy images of 4T1 cells treated with 0.1 mg/mL of PLGA-PEG-PH20-NPs with 50 U/mL of conjugated PH20 activity. With this treatment, PLGA-PEG-PH20-NPs removed the majority of HA matrix surrounding the 4T1 cells, which allowed the nanoparticles to directly contact and enter the cells. Nanoparticles were labeled with DiD dye and showed as red, HA was stained in green, and nuclei were stained in blue. (The scale bar is 50 μm).

The 4T1 cells were treated with PLGA-PEG-PH20-NPs conjugated with a higher PH20 activity, as prepared in condition 3 (FIG. 15C). When 4T1 cells were treated with PLGA-PEG-PH20-NP (0.1 mg/mL) with 50 U/mL of conjugated PH20 activity, the enhancement of internalization due to a higher conjugated PH20 activity was similar to that of nanoparticles with a lower conjugated PH20 activity (FIG. 17C), though HA around the cells was degraded faster and more completely. When the cells were treated with 0.1 mg/mL of PLGA-PEG-PH20-NPs with 68 U/mL of conjugated PH20 activity, the enhancement of NP internalization and membrane binding exhibited a similar trend.

Figure 18A:
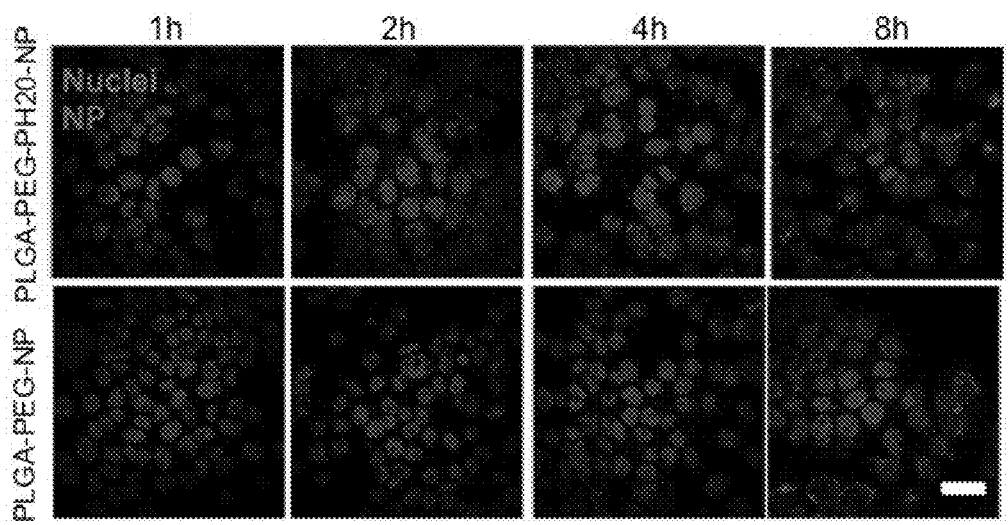
FIG. 18A shows confocal microscopy fluorescence images of 4T1 cells treated with 0.1 mg/mL of PLGA-PEG-PH20-NPs (with 68 U/mL of conjugated PH20 activity) and PLGA-PEG-NPs (no PH20 activity). Nanoparticles were labeled with DiD dye and showed as red, and nuclei were stained in blue. (The scale bar: 50 μm).
Figure 18B:
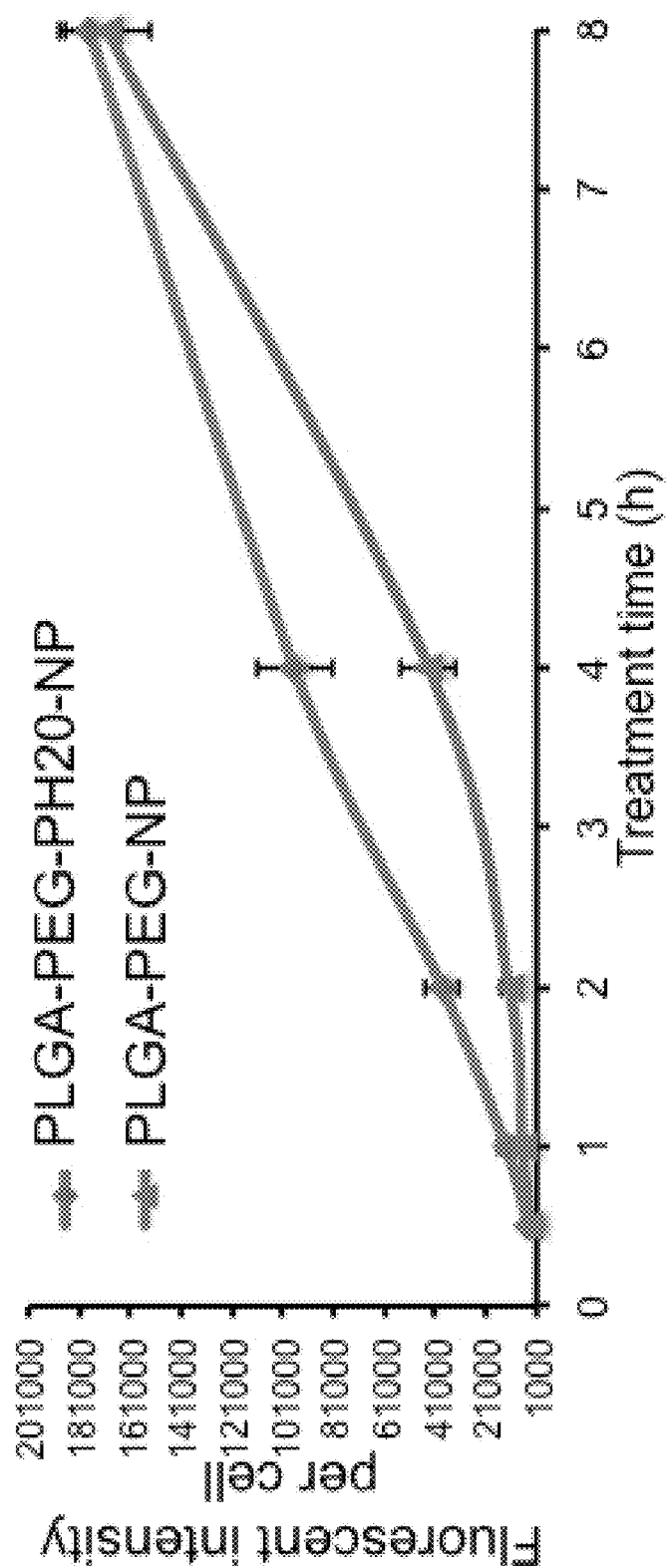
FIG. 18B shows a quantitative analysis of nanoparticles internalized in the 4T1 cells after the same treatments described in FIG. 18A. Values indicate mean±standard deviation (n=10).

Moreover, after a longer treatment period of 8 h, the overall amount of internalized nanoparticles with or without the conjugated PH20 tended to be the same (FIGS. 18A-18B). This may be explained by the fact that the cells were capable of taking up only a limited amount of nanoparticles. As more and more nanoparticles diffused through the HA matrix layer, but were not internalized by cells, the nanoparticle concentration built up close to the cells. Gradually, nanoparticle concentrations on both sides of HA matrix reached equilibrium. Nanoparticles then lost the driving force for further diffusion. However, in practice the concentration of nanoparticles diffused into tumors would not likely reach the saturation point due to the relatively low NP/cell ratio in vivo and the difficulty of diffusion in dense tumor ECM.

Example 7

The capacity of the nanoparticles produced in Example 2 for delivering an active pharmaceutical agent was tested using DOX encapsulated in nanoparticles as produced in Example 2. DOX was encapsulated inside PLGA cores in the step of nanoprecipitation. The DOX loading yield in PLGA-PEG-NPs was around 3.5 wt %, as shown in Table 1 below.

TABLE 1

DOX loading capacity in NPs. Values indicate mean ± s.d. (n = 3)

| NPs | DOX Loading Yield (% DOX/Polymer) |
|---|---|
| DOX-PLGA-PEG-NP | 3.37 ± 0.22 |
| DOX-PLGA-PEG-PH20-NP | 3.54 ± 0.12 |

The DOX encapsulated in the nanoparticles may be released from the nanoparticles. To measure the in vitro release of DOX, 0.5 mL of DOX-nanoparticles (encapsulating 30 μg/mL of DOX) was added into a dialysis tube (Slide-A-Lyzer, 10K MWCO, Thermo Scientific) and DOX was allowed to release against 10% FBS in PBS. The tubes were gently shaken at 150 rpm at 37° C. At each time interval, the total volume of the solution inside the dialysis bag was recorded and the dialysis buffer solution was replaced. 10 μL of the resultant nanoparticle solution was withdrawn and completely dissolved in 190 μL DMSO for fluorescence intensity measurement at excitation/emission wavelengths of 480/595 nm using TECAN (Infinite M200).

Figure 12A:
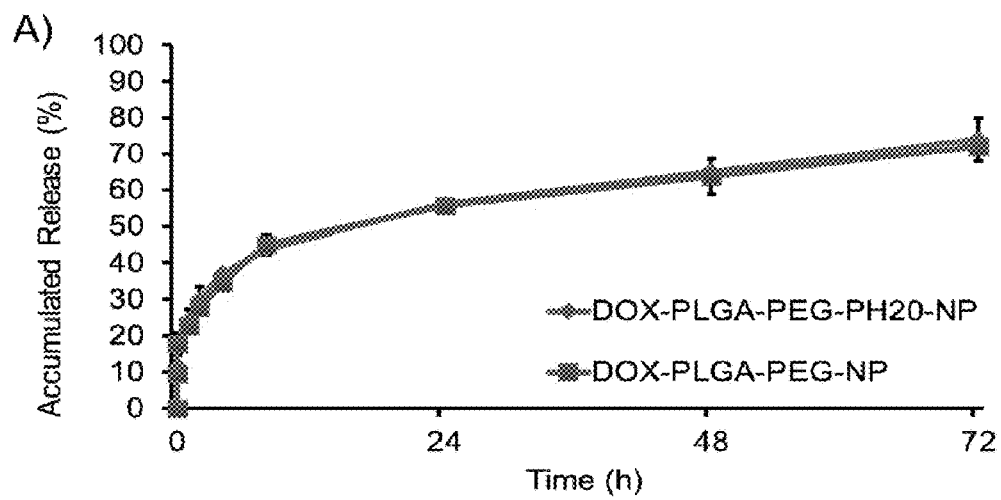
FIG. 12A shows in vitro drug release from DOX-encapsulated PLGA-PEG-PH20-NPs (DOX-PLGA-PEG-PH20-NPs) and DOX-encapsulated PLGA-PEG-NPs (DOX-PLGA-PEG-NPs, no surface conjugated PH20). Values indicate mean±standard deviation (n=4). Nanoparticles at a concentration of 1 mg/mL were shaken at 200 rpm at 37° C. in dialysis against 10% FBS in PBS, and the DOX released from the nanoparticles was detected by measuring its fluorescence intensity in the solution (Excitation wavelength: 495 nm; Emission wavelength: 580 nm).

Burst release of DOX from nanoparticles may be reduced via overnight dialysis against saline in the final step of nanoparticle preparation. After dialysis, only about 20% of DOX was released within 1 h in PBS supplemented with 10% FBS at 37° C. After 3 d, 30% of the total DOX remained in the nanoparticles. The conjugation of PLGA-PEG-NPs with PH20 did not alter the release profile of DOX from NPs (FIG. 12A).

The therapeutic potential of nanoparticles encapsulating DOX was evaluated in vitro using an MTT assay with free DOX and nanoparticles with no encapsulated DOX as the controls. 4T1 cells were cultured with RPMI-1640 medium w/o Phenol Red in a 96-well plate one day before the MTT assay. 1 mL of nanoparticles (with encapsulated DOX) or controls were added into each well right after their preparation to reach a DOX concentration of 3 μg/mL. Free DOX stock solution was prepared by dissolving 1 mg/mL of DOX in water and dilution in saline. 4T1 cells were treated with either PLGA-PEG-PH20-NPs or PLGA-PEG-NPs with and without DOX encapsulated for either 24 h or 4 h. For the 4 h treatment, the culture medium containing NP samples or free DOX was removed at 4 h, and 4T1 cells were washed 3 times with PBS before further incubation the cells in fresh medium for another 20 h. At the end of the incubation, 20 μL of 5 mg/mL Thiazolyl Blue Tetrazolium Bromide (MTT) in PBS were added to 100 μL medium per well. After incubation for another 4 h, the medium was carefully removed and 200 μL DMSO was added to each well. The absorbance at 570 nm with a reference at 630 nm was measured for each well after 5 min incubation and 3 min shaking. Relative cell viability (released DOX is toxic to cells) was obtained by comparing to untreated cells. All measurements were done in triplicate.

Figure 19:
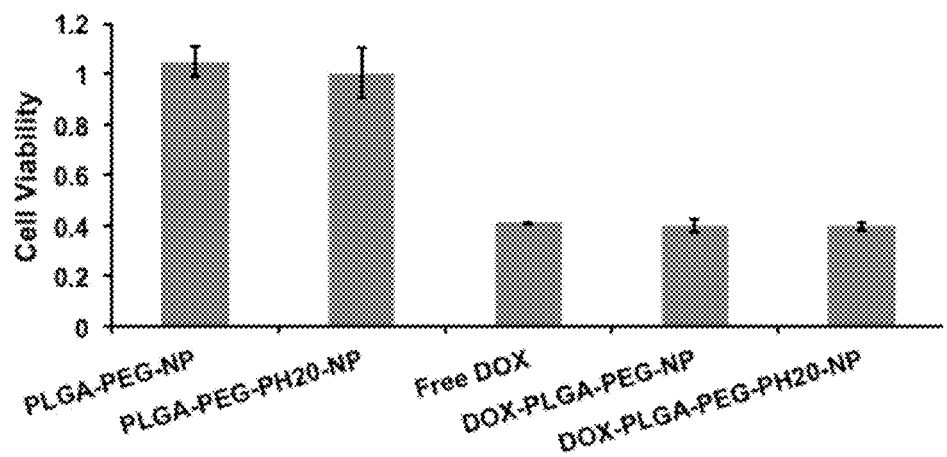
FIG. 19 shows results of a cell viability study conducted via the MTT assay. Cells were treated for 24 h with nanoparticles with or without conjugated PH20, and with or without encapsulated DOX. Values indicate mean±standard deviation (n=3).

4T1 cells treated with nanoparticles without encapsulated DOX (PLGA-PEG-NPs and PLGA-PEG-PH20-NPs) all reached a viability of around 100% as compared to the saline-treated cells (FIG. 19), indicating that nanocarriers themselves were not toxic to cells. The viabilities of cells treated with DOX-encapsulated PLGA-PEG-NPs (DOX-PLGA-PEG-NPs) and PLGA-PEG-PH20-NPs (DOX-PLGA-PEG-PH20-NP) for 24 hr reached about 40%, a toxic effect comparable to 3 μg/mL of free DOX (FIG. 19). This data was consistent with the kinetics study that given a long enough time, cells reach saturation for nanoparticle uptake regardless of the amount of conjugated PH20 on their surfaces (FIGS. 18A-18B).

Figure 12B:
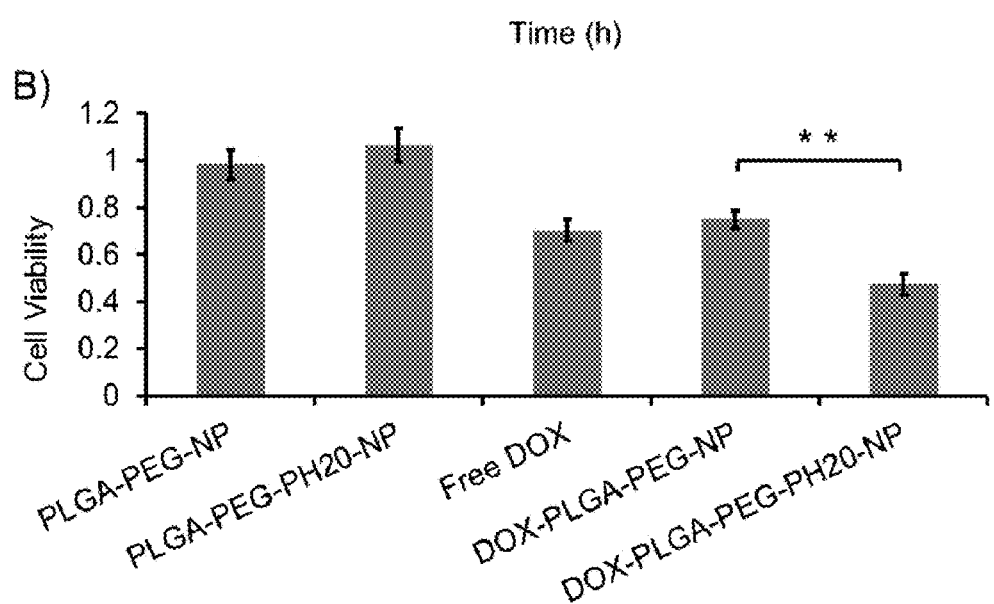
FIG. 12B shows cell viability as measured by a Thiazolyl Blue Tetrazolium Bromide (MTT) assay. The 4T1 cells were incubated with either DOX-PLGA-PEG-PH20-NPs or DOX-PLGA-PEG-NPs (each encapsulating 3 µg/mL of DOX) in 96-well plate for 4 h. Cells treated with PBS, an equal amount of free DOX, or nanoparticles without encapsulated DOX served as controls. Nanoparticles and free DOX were then removed, and cells were washed with PBS and cultured in fresh medium for another 20 h to measure growth of the treated cells. Values indicate mean±standard deviation (n=3). Nanoparticles alone were not toxic to the 4T1 cells. DOX-PLGA-PEG-PH20-NPs were more effective than DOX-PLGA-PEG-NPs in reducing 4T1 cell viability. (As measured by ANOVA with "**" indicating p<0.01).
Figure 12C:
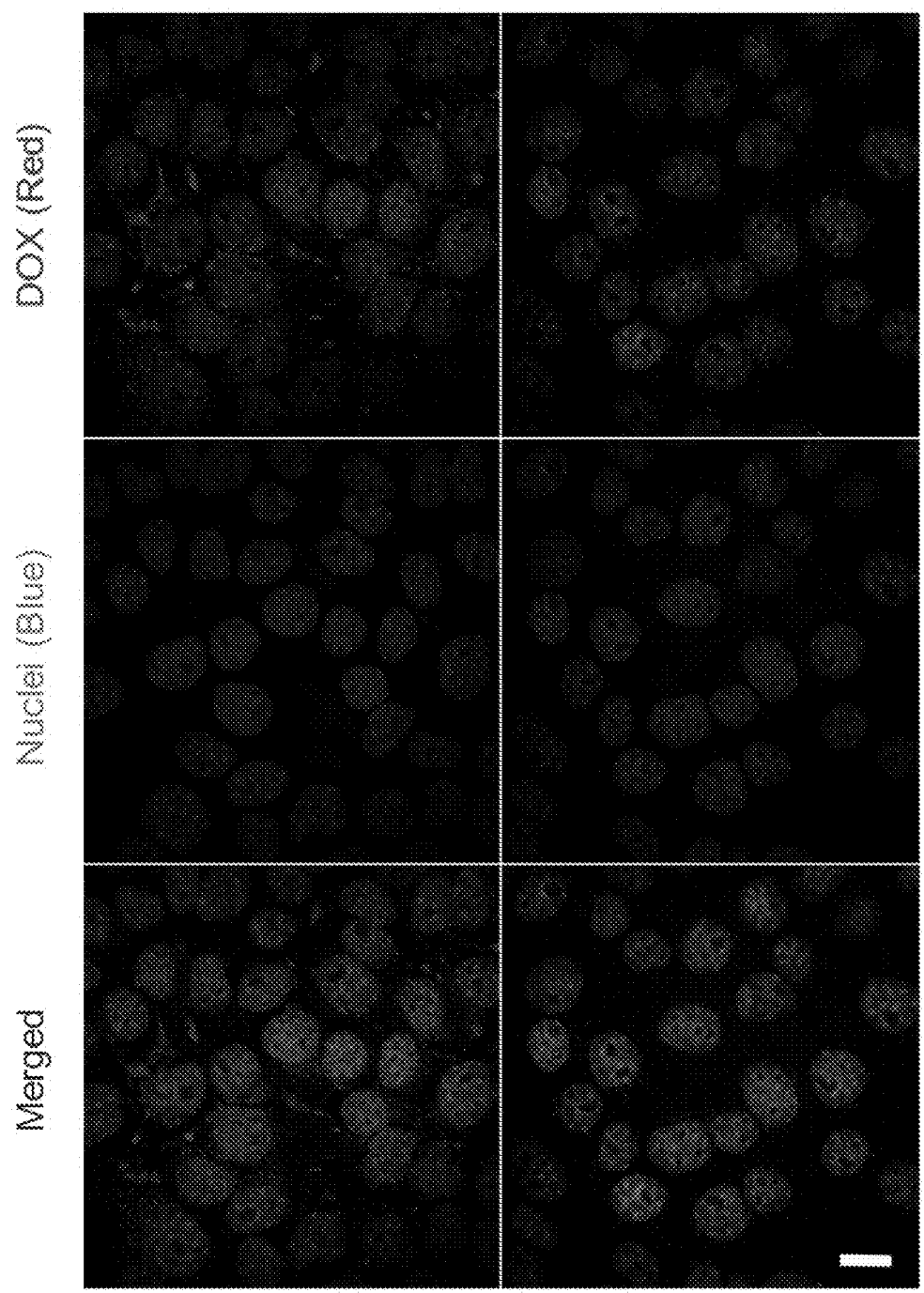
FIG. 12C shows confocal microscopy images of 4T1 cells treated with DOX-encapsulated nanoparticles, with or without conjugated PH20 (Red: DOX; Blue: Nuclei), as described in FIG. 12B. The amount of nanoparticles that were used to treat cells were equalized using DOX fluorescence intensity. The concentration of encapsulated DOX was 10 µg/mL. After 2 h incubation with the nanoparticles, the coverslips were washed and fixed for imaging via confocal microscopy.

To assess the effect of PH20 on cell viability, 4T1 cells were incubated with nanoparticles for 4 h before being washed and changed back to a normal culture medium and culturing was continued for 20 h (FIG. 12B). The overall viabilities of cells treated with DOX-PLGA-PEG-NPs increased to above 75%. However, the viability of cells treated with DOX-PLGA-PEG-PH20-NPs was 47%, which was significantly lower than cells treated with DOX-PLGA-PEG-NPs or free DOX. This result also agreed with the PH20-enhanced NP internalization by 4T1 cells at 4 h treatment. Further, in confocal images (FIG. 12C), cells in both treatments showed DOX signals in nuclei. The difference in nuclei-accumulated DOX between DOX-PLGA-PEG-PH20-NP and DOX-PLGA-PEG-NP treatments was not as significant as in the case of DiD labeled NPs. This was likely because of the burst release of free DOX from the nanoparticles in the cell culture medium and because the small-sized free DOX cross the HA matrix much easier than nanoparticles. Only in the image of cells treated with DOX-PLGA-PEG-PH20-NPs, were there were many red dots outside of the cell nuclei (FIG. 12C), indicating that the nanoparticles penetrated through the HA layer.

Example 8

Efficacy of the nanoparticles produced in Example 2 was evaluated in a mouse 4T1 syngeneic breast tumor model, in which the host BALB/c mouse is immune-competent, and the tumor growth and metastatic spread of 4T1 cells closely mimic human breast cancer. Female BALB/c mice at 6 weeks were ordered and within a one-week stay, 50 μL of $1\times10^7$ 4 T1 cells/mL in PBS was injected at the mammary fat pad on the right flank of the mice. Tumor size was calculated using $V=0.5\times width^2 \times length$.

A solution of DiD-encapsulated nanoparticles at 10 mg/mL was systematically administered through tail vein injection. Each mouse received 100 μL nanoparticle solution. Fifteen μL blood was collected at 2 min, 15 min, 0.5 h, 1 h, 2 h, 4 h, 8 h, 24 h, 48 h and 72 h post i.v. injection. The blood was diluted in 200 uL PBS containing 16 U/mL Heparin as anticoagulants. Cells were removed through spinning at 300 g for 5 min, and 180 μL of the supernatant was used to test for fluorescence intensity using TECAN. The half-life of in vivo circulation was calculated based on a one-compartment model of pharmacokinetics via a PKSolver. To quantify the enzyme activity half-life of PH20 on the nanoparticles, EDTA was used instead of heparin during blood collection.

Figure 13A:
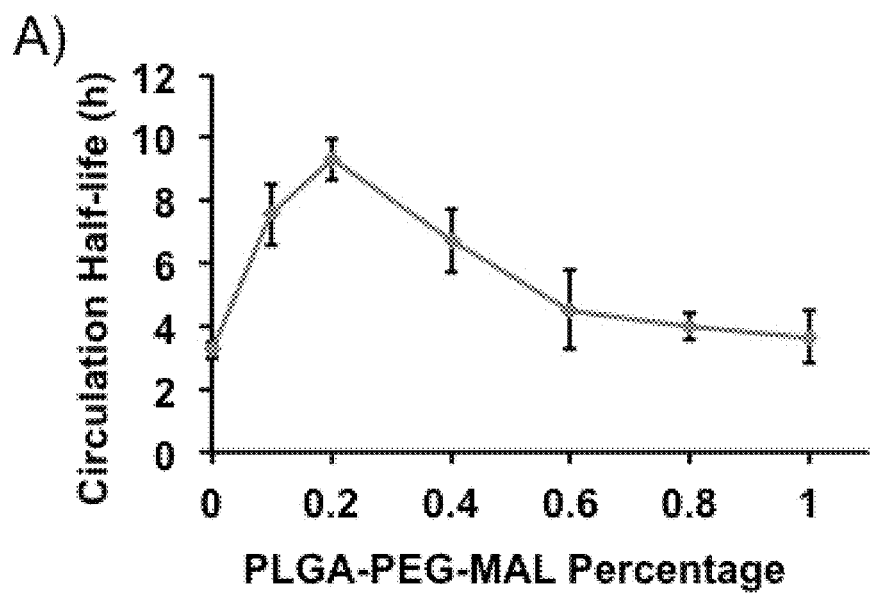
FIG. 13A shows that there is an optimized percentage/density of second PEG layer to prolong the circulation half-life of regular PLGA-PEG-NPs that do not have the second PEG layer. The plot shows the circulation half-lives of DiD-labeled PLGA-PEG-NPs with a series of PLGA-PEG-Maleimide compositions (0, 10%, 20%, 40%, 60%, 80%, 100%) in polymer during nanoparticle preparation (as described in Example 2). Value indicates mean±standard deviation (n=6-8, from two independent experiments). The second PEG layer was produced by conjugating $PEG_{2K}$-thiol on nanoparticle surfaces using a thiol-maleimide reaction. Fitted half-lives were obtained by fitting to a one-compartment pharmacokinetic model.
Figure 20A:
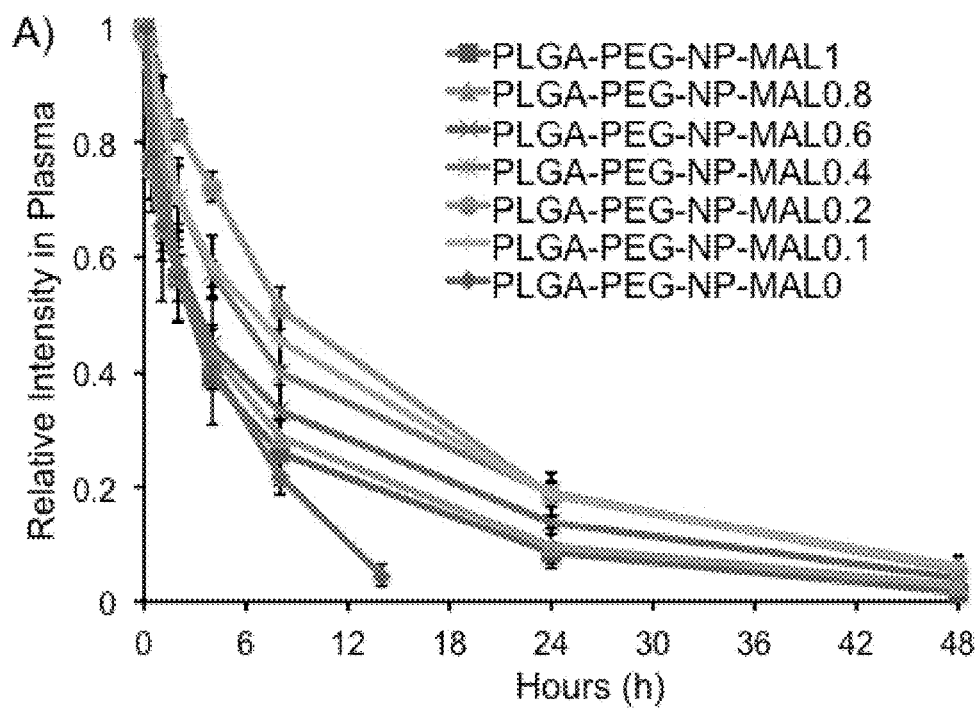
FIG. 20A shows the amount of PLGA-PEG-NPs in in vivo circulation over time. The nanoparticles were produced with a series concentration of PLGA-PEG-Maleimide (0, 0.1, 0.2, 0.4, 0.6, 0.8, 1) in the polymer during nanoparticle preparation as described in Example 2. The second PEG layer was produced by conjugating $PEG_{2K}$-thiol on nanoparticle surfaces through a thiol-maleimide reaction. Value indicates mean±standard deviation (n=6-8, from two independent experiments).

In order to optimize the density of the second PEG layer on nanoparticles for best efficacy in vivo, DiD-labeled nanoparticles with a series of PLGA-PEG-MAL concentrations were prepared and their in vivo circulations were evaluated by measuring the fluorescence intensity of blood samples of the animals (FIG. 20A). The half-lives of the nanoparticles were fitted to the pharmacokinetic one-compartment model using a PKSolver (FIG. 13A). It was found that 10% of the second layer of PEG was sufficient to increase the circulation half-life of nanoparticles from 3.3±0.27 h to 7.6±0.97 h, while nanoparticles made of 20% PLGA-PEG-MAL showed the longest circulation half-life of 9.3±0.65 h, which is almost a 3-fold increase of the circulation time compared to the nanoparticles without a second layer. When the PLGA-PEG-MAL in the nanoparticles was increased above 40%, the circulation half-life of the nanoparticles gradually decreased probably because of a decrease in PEG chain fluctuation. Nanoparticles made of 80% and 100% of PLGA-PEG-MAL showed similar circulation half-lives to the nanoparticles with no second PEG layer. This also confirmed the necessity of introducing surface PEG fluctuation via a second layer of PEGs.

Figure 20B:
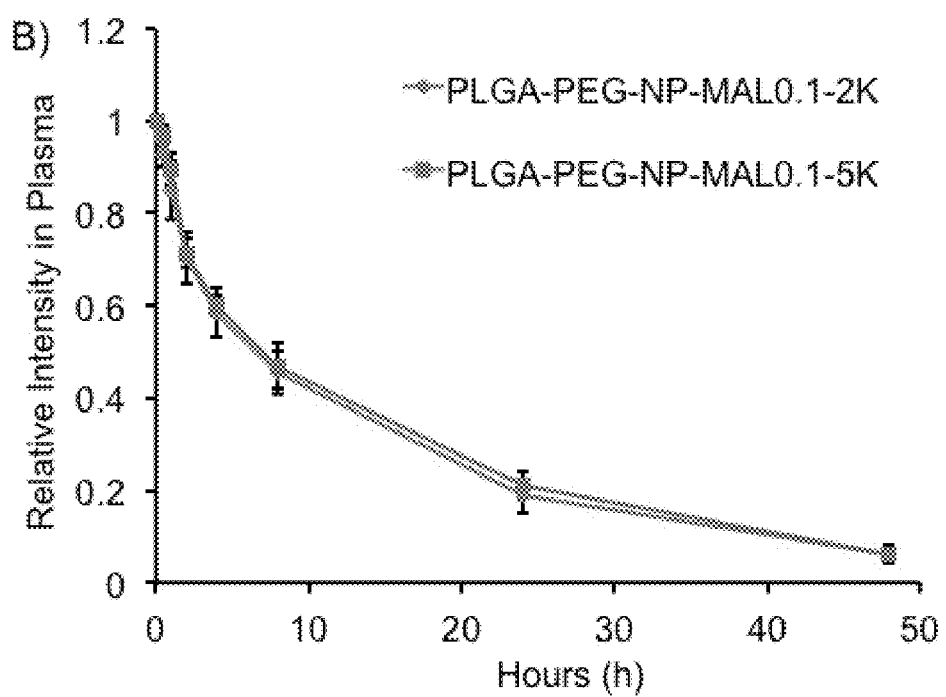
FIG. 20B shows the amount of nanoparticles in in vivo circulation over time, where the PLGA-PEG-NP-MAL0.1 was linked to the second PEG layer of either $PEG_{2K}$ or $PEG_{5K}$ chains. Values indicate mean±standard deviation (n=4-6).

The best ratio between PLGA-PEG-MAL and PLGA-PEG (about 4:1) for producing the second PEG layer was used in another study to evaluate whether the length of the second layer of PEG would influence the circulation time for the nanoparticles. $PEG_{5K}$-thiol and $PEG_{2K}$-thiol were used to produce the second PEG layer (FIG. 20B). The difference in circulation time between nanoparticles with a 2K-length second PEG layer and nanoparticles with a 5K-length second PEG layer was not significant maybe because the first layer (inner layer) of 5K PEG was already sufficient to provide enough PEG thickness to repel protein adsorption on the underneath nanoparticles. There was no significant difference in the kinetic interference of protein binding via 5K or 2K PEGs of the second PEG layer. This demonstrated that increasing the length of PEG chains in the second layer, from 2K to 5K or to 7K may not increase nanoparticle circulation time when the overall PEG layer was sufficiently thick.

A composition of 20% PLGA-PEG-MAL and 80% PLGA-PEG was mixed with $PEG_{2K}$-thiol to make nanoparticles for all of the in vivo studies in this and the following examples. All such nanoparticles showed the best circulation performance, they allowed the conjugation of a high density of PH20 on the nanoparticle surfaces, and the second PEG layer was not too thick to block the enzymatic function of the conjugated PH20.

Figure 13B:
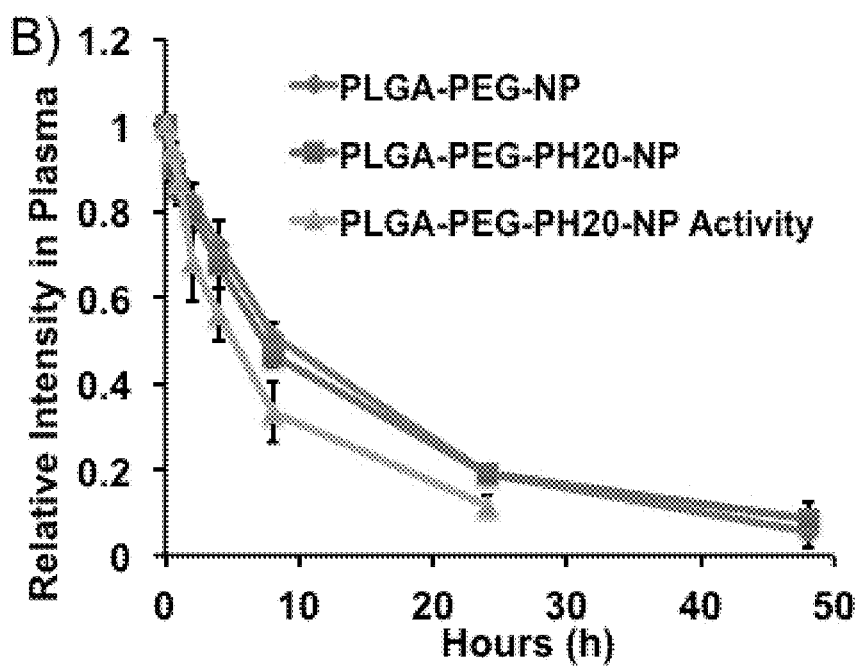
FIG. 13B shows that modification of PLGA-PEG-nanoparticles does not alter the circulation time of nanoparticles. When the circulation half-life of nanoparticles is quantified by measuring activity of conjugated PH20, the circulation half-life is a little shorter than that evaluated using the fluorescent signal of circulating nanoparticles. The plot shows the circulation half-lives of DiD-labeled PLGA-PEG-NPs, PLGA-PEG-PH20-NPs and PLGA-PEG-PH20-NP Activity. Values indicate mean±standard deviation (n=3-6).

Conjugation of PH20 on nanoparticles did not influence their circulation time (FIG. 13B) as the measured half-lives of the nanoparticles before and after PH20 conjugation were 9.3±0.65 h and 8.7±0.39 h respectively. The circulation half-life of free PH20 was less than 3 min, but it was increased to 10.3 h after pegylation with high molecular weight $PEG_{30K}$, though this modification reduces the PH20 enzyme activity by 75%. To confirm that the PH20 conjugated on nanoparticles retained its activity during circulation, the activity half-life of PH20 conjugated on nanoparticles was measured and determined to be around 7.3 h (FIG. 13B), which was a little shorter than the nanoparticle half-life of PLGA-PEG-PH20-NPs.

Example 9

The nanoparticles produced in Example 2 were used to treat tumors in a mouse 4T1 syngeneic breast tumor model BALB/c mice. When the tumors reached a size of 200-350 mm³, the mice were randomly assigned into 4 groups and injected with 150 μL of 10 mg/ml DiD labeled PH20-PLGA-PEG-PH20-NPs, PLGA-PEG-NPs, PLGA-PEG-NP-MAL0 and saline respectively (FIGS. 13C-13D) for the biodistribution study. IVIS imaging was taken at 1 h, 3 h, 6 h and 24 h post-injection. After 24 h, mice were sacrificed and their brains, lungs, hearts, livers, spleens, kidneys as well as tumors were collected and the amount of nanoparticles inside each was quantified through IVIS Fluorescence Imaging (605 nm excitation and Cy5.5 emission, 1s exposure). All the organs/tissues were weighted before being homogenized and their fluorescence intensities were detected by 600/665 nm via TECAN.

Figure 13C:
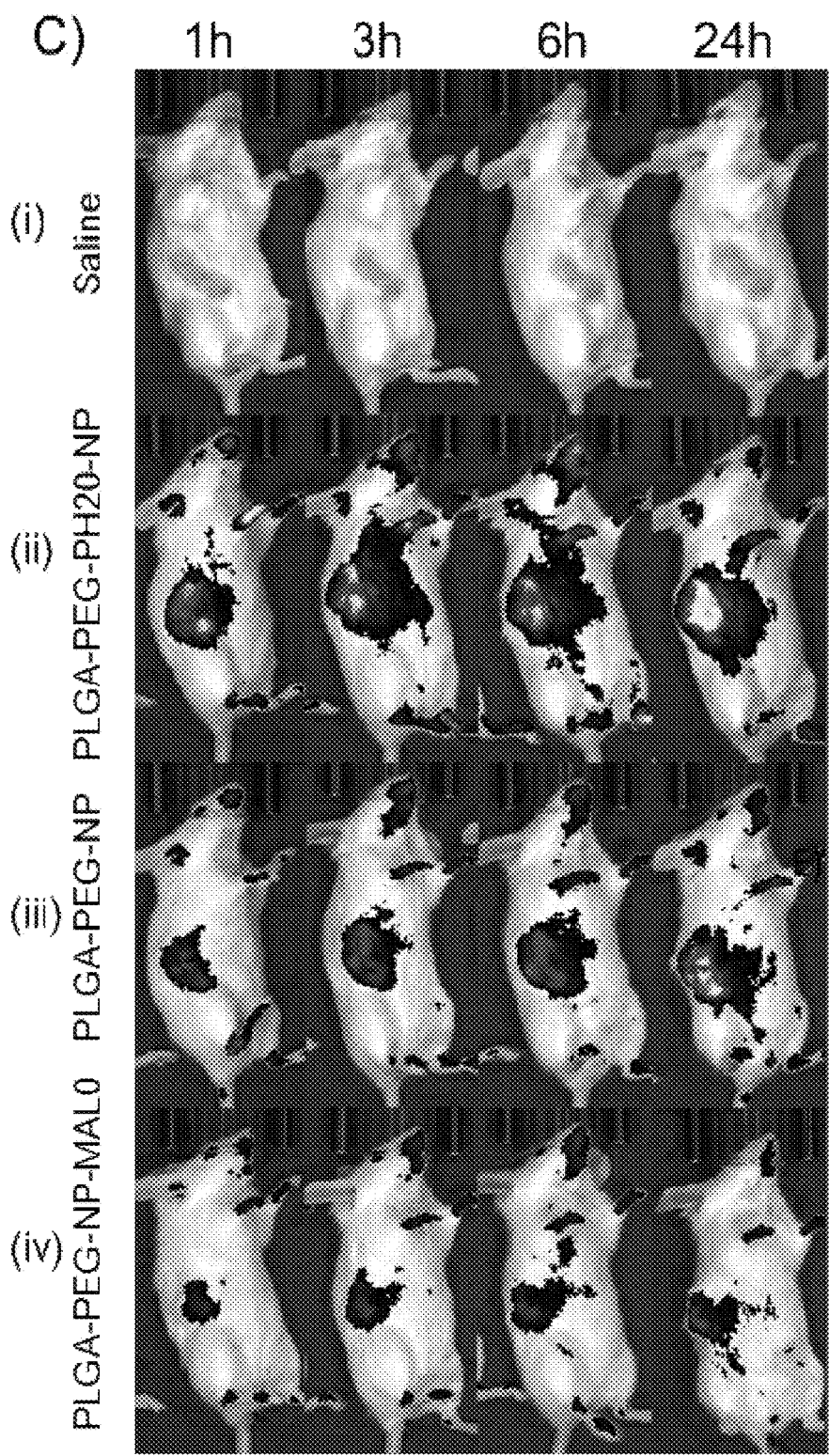
FIG. 13C shows fluorescence images of 4T1 tumor-bearing mice captured by an IVIS® system at 1, 3, 6 and 24 h post-injection of either saline, PLGA-PEG-PH20-NPs, PLGA-PEG-NPs or PLGA-PEG-NPs-MAL0 produced in Example 2. All types of nanoparticles were labeled with equal amounts of DiD fluorescence. "MAL0" refers the amount of maleimide in the composition with "0" indicating "0% maleimide").
Figure 13D:
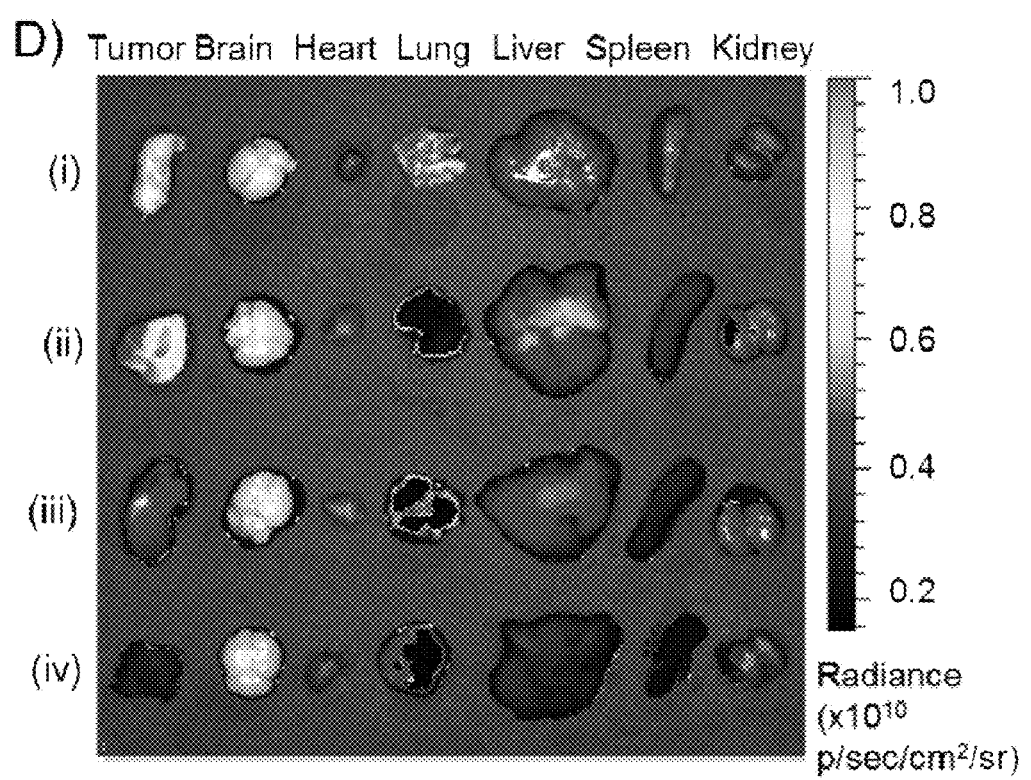
FIG. 13D shows fluorescence images of animal organs/tissues of the treated mice using the IVIS® system as described in FIG. 13C, at 24 h post-injection of saline (I), DiD-labeled PLGA-PEG-PH20-NPs (II), PLGA-PEG-NPs (III), and PLGA-PEG-NPs-MAL0 (IV).
Figure 13E:
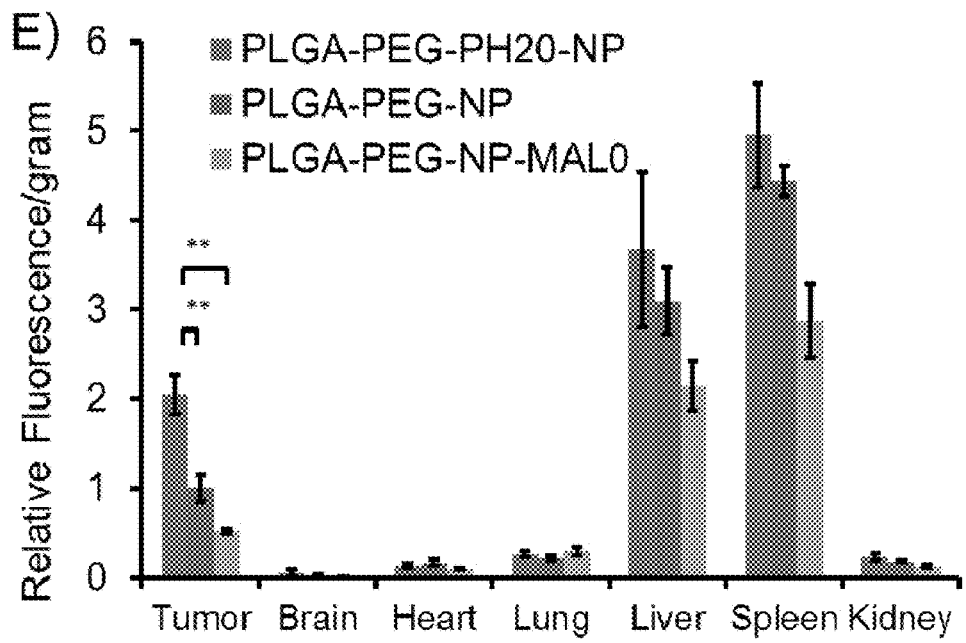
FIG. 13E shows a quantitative comparison of nanoparticle biodistribution in different organs/tissues of the treated mice (as described in FIG. 13C) based on the fluorescence intensity of homogenized tissues that were collected at 24 h post-nanoparticle injection. Relative fluorescence intensities per gram in tumor, brain, heart, lung, liver, spleen and kidney tissue are presented. PLGA-PEG-PH20-NPs showed a significantly higher accumulation in 4T1 tumor compared to nanoparticles without PH20 modification. Values indicate mean±standard deviation (n=3). Measured by ANOVA with "**" indicating p<0.01.

A higher nanoparticle accumulation in tumors was observed from imaging live animals and harvested organs/tissues (FIGS. 13C-13D). Quantitative analysis was performed by homogenizing tissue and measuring the DiD signal in sample solutions (FIG. 13E). It was found that the increased circulation time of nanoparticles improved their accumulation in tumors by one fold at 24 h post tail vain injection of nanoparticles. PLGA-PEG-NPs showed higher signals in the liver and spleen than the regular nanoparticles without the second PEG layer (PLGA-PEG-NP-MAL0) (FIGS. 13D-13E). This may be because of faster capture of regular nanoparticles relative to PLGA-PEG-NPs by phagocytic cells in these tissues, and because more nanoparticles had already been degraded by the time of sample collection.

It was found that conjugation of PH20 on nanoparticles further improved nanoparticle accumulation in tumors by another 100%. Since PLGA-PEG-PH20-NPs did not alter nanoparticle circulation time, it is believed that the PH20-mediated matrix penetration increased nanoparticle accumulation in tumors. Possibly due to the same reason, PLGA-PEG-PH20-NPs also showed slightly higher nanoparticle signals than PLGA-PEG-NPs in the liver and spleen of the treated mice.

Example 10

Figure 14A:
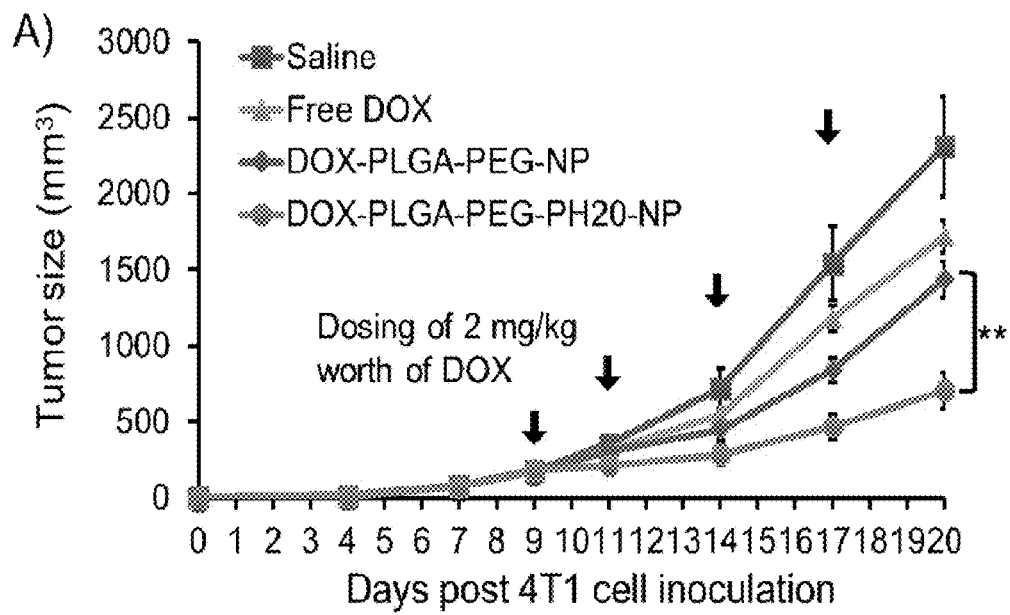
FIG. 14A shows in vivo tumor growth inhibition curves for 4T1 tumor-bearing mice that were treated with either saline, free DOX, DOX-PLGA-PEG-NPs or DOX-PLGA-PEG-PH20-NPs. Values indicate mean±standard deviation (n=6). Measurement were made using ANOVA, and ** indicates p<0.01. The dates of nanoparticle dosing post 4T1 cell inoculation were marked with black arrows.

The nanoparticles with encapsulated DOX produced in Example 2 were used to treat tumors in a mouse 4T1 syngeneic breast tumor model BALB/c mice. The mice were randomly assigned into 4 groups and injected with saline, free DOX in saline, DOX-PLGA-PEG-NPs and DOX-PLGA-PEG-PH20-NPs (PH20 activity of DOX-PLGA-PEG-PH20-NPs is 500 U/mouse) at 2 mg/kg mice of DOX at 9, 11, 14, 17, 20 days after inoculation of 4T1 cells in the mice. The tumors reached a size of 150-250 mm³ at day 9 before treatment. Tumor sizes were monitored throughout the whole study (FIG. 14A). The survival rate was studied based on the number of mice in each group that survived over time. MST (day) was defined as the time at which half of the mice had died.

The percentage ILS (%) was calculated using the following equation: ILS (%)=[(MST of treated group/MST of control group) −1]*100. The antitumor efficacy of free PH20 was not studied because PH20 has a short half-life of 3 min, not suitable for i.v. injection.

All the mice in the DOX treated groups survived longer than the control group of mice treated with saline. DOX-PLGA-PEG-NPs showed slightly better antitumor efficacy than free DOX in terms of reducing primary tumor growth. DOX-PLGA-PEG-PH20-NPs exhibited an antitumor efficacy superior to free DOX or DOX-PLGA-PEG-NPs. The treatment with DOX-PLGA-PEG-PH20-NPs efficiently inhibited the growth of aggressive 4T1 tumors in spite of a low DOX dose (FIG. 14A). The increased nanoparticle accumulation in tumors appeared to be a major reason for the antitumor efficacy of DOX-PLGA-PEG-PH20-NPs.

Figure 14B:
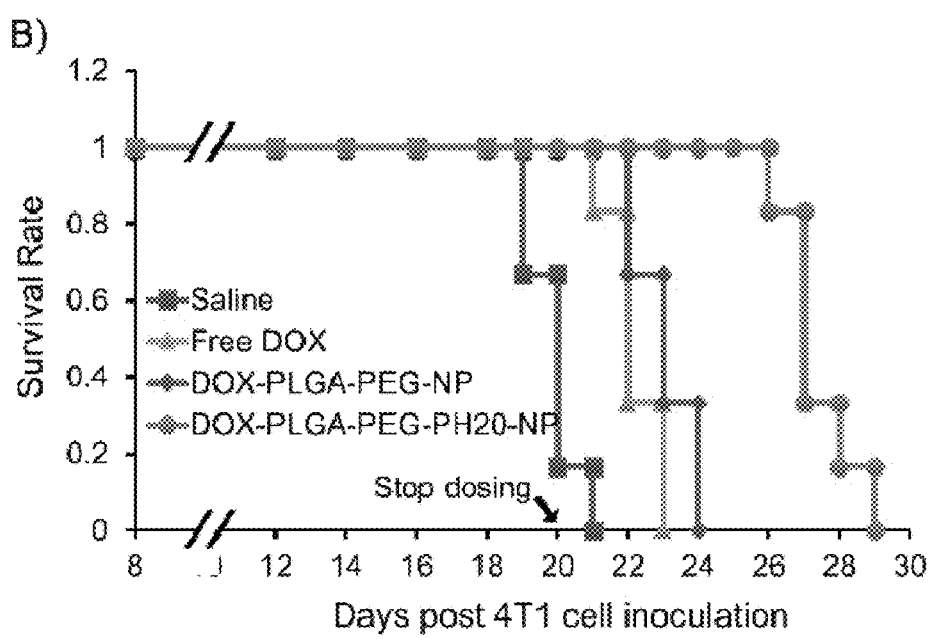
FIG. 14B is a survival rate plot showing the percentage of animals that remained alive in the study described in FIG. 14A. Mice were sacrificed and stopped counting for survival rate when their tumor size exceeded 2000 $mm^3$. ANOVA, ** indicates p<0.01.
Figure 21A:
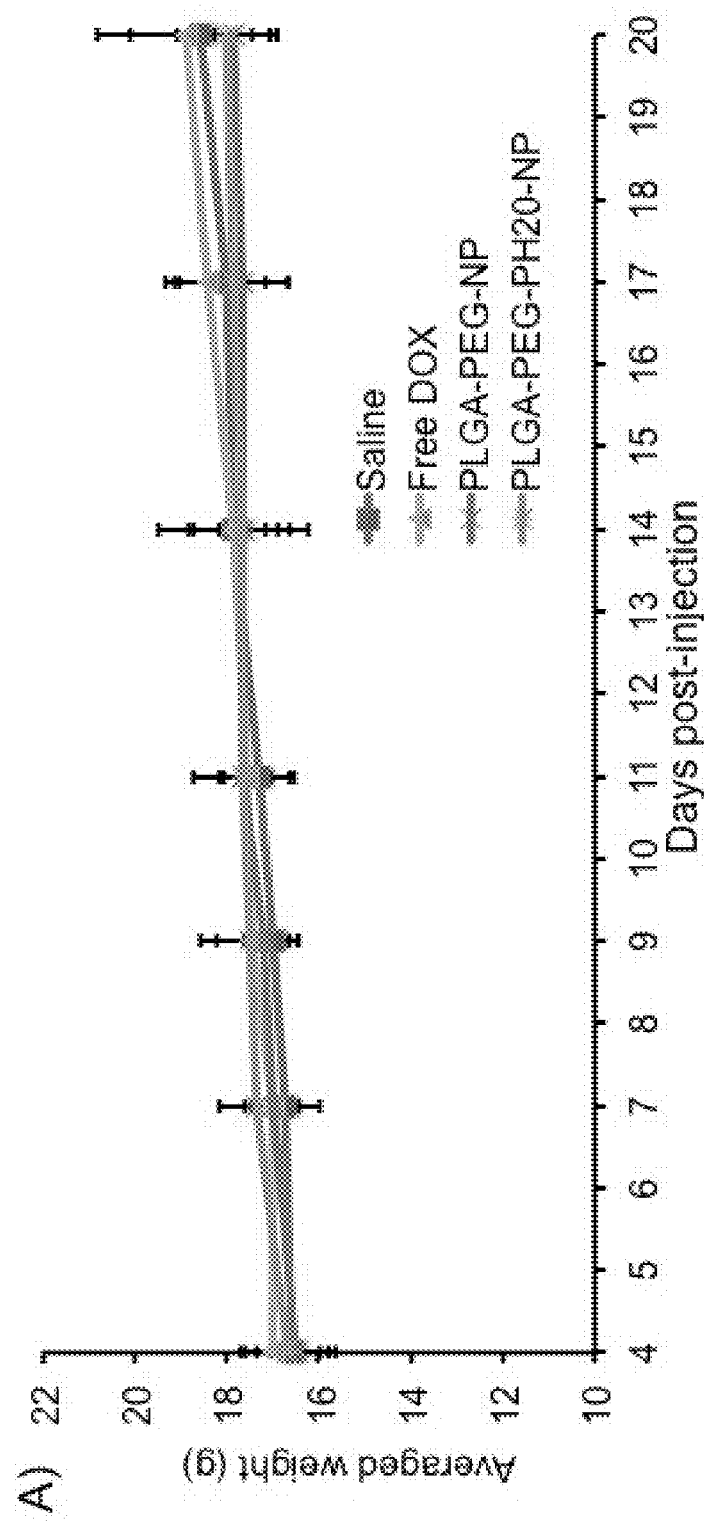
FIG. 21A shows averaged weight of mice over time after inoculation of 4T1 cells and treatments with nanoparticles or controls as described in FIG. 14A. Values indicate mean±standard deviation (n=6).

Median survival time (MST, days when half of the mice died) and percentage increased life span (ILS (%)=(MST of the treated group/MST of control group-1)×100) was calculated for each group (FIG. 14B). Free DOX and DOX-PLGA-PEG-NPs showed ILSs of 10% and 15%, while DOX-PLGA-PEG-PH20-NPs showed a significantly higher ILS of 35%. The weight of mice did not show a significant difference between the study groups (FIG. 21A), indicating that the treatment of DOX-PLGA-PEG-PH20-NPs was well tolerated in the tumor-bearing mice.

Example 11

To further understand the antitumor mechanism of PLGA-PEG-PH20-NPs produced in Example 2, tumor cell apoptosis, nanoparticle spatial distribution and variation of tumor HA before and after treatment with PLGA-PEG-PH20-NPs or controls were analyzed. Two days after the last dosing of nanoparticles, mice from each study group were sacrificed and their tumors were collected and frozen at −80° C. in M-1 Embedding Matrix. 10 μm tumor sections were used for TUNEL staining (Life Technology) by following the manufacturer's instructions.

For the biodistribution study, the 10 μm thick tumor sections on slides were fixed in acetone at −20° C. for 5 min and air dried before washing three times with PBS. Blocking was carried out in 3% BSA in PBS solution for 1 h at room temperature. Rat anti-Mouse CD31 (BD Pharmingen™) for CD31 staining was diluted at 1:100 and HABP (HA binding Protein, Bovine Nasal Cartilage, Biotinylated, CalBioChem) was diluted at 1:100 for HA staining. After incubation for 3 h at room temperature, the slides with tumor sections were washed three times with PBS. Alexa Fluor 488-Goat anti-rat IgG (H+L, Jackson ImmunoResearch Inc) and Alexa Fluor 488-conjugated Streptavidin (Life Technologies) were incubated respectively for 2 h at room temperature before washing and mounting. Fluorescence images were take via confocal microscopy (Olympus)

Figure 14C:
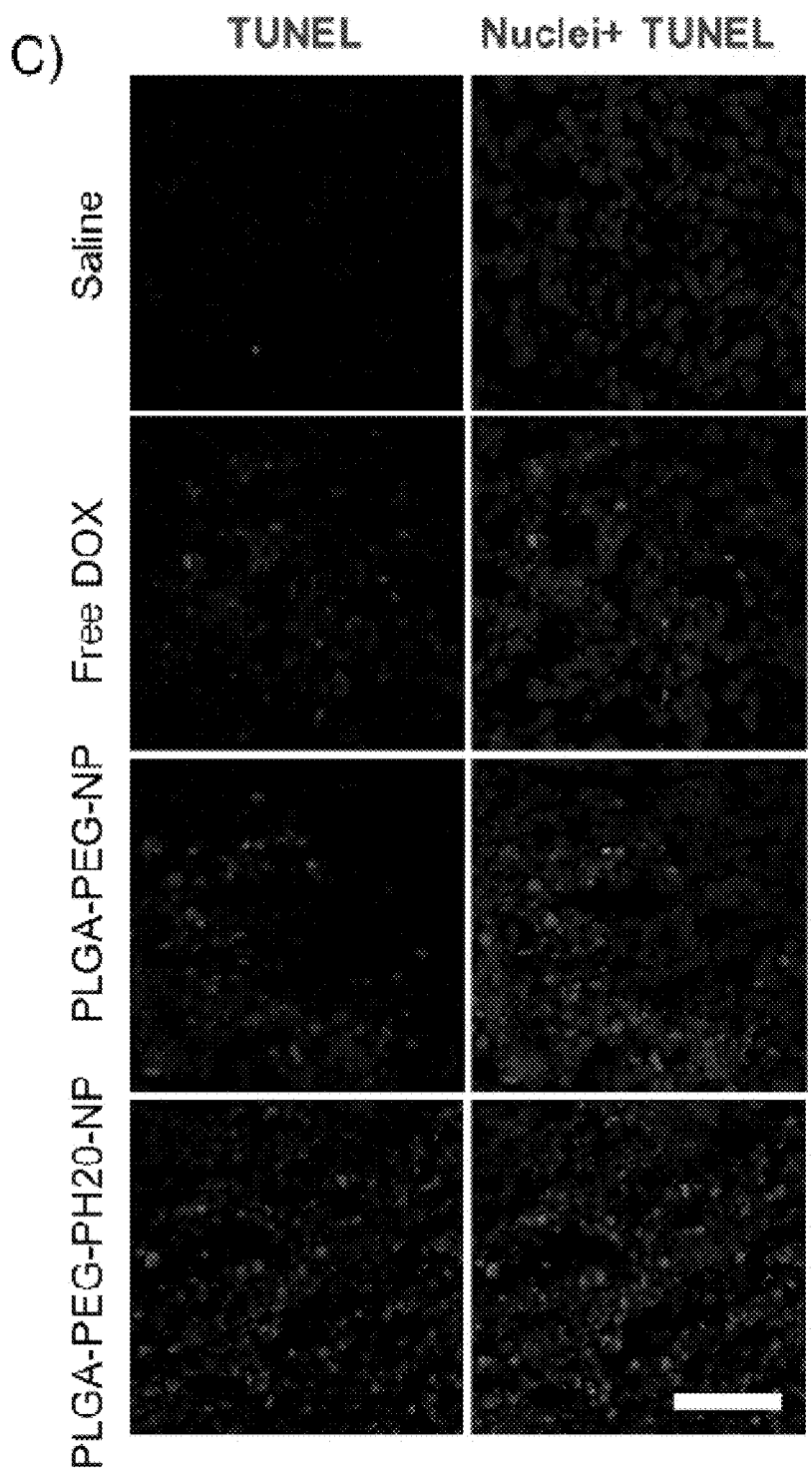
FIG. 14C shows images of TUNEL staining of sectioned tumors that were collected after the completion of all doses for the animal groups treated with saline, free DOX, DOX-PLGA-PEG-NPs or DOX-PLGA-PEG-PH20-NPs as described in FIG. 14A. Green: TUNEL; Blue: Nuclei. (The scale bar is 100 µm).

Apoptotic cells in the 4T1 10 μm tumor sections were stained with TUNEL. The representative confocal microscopy images showed that DOX-PLGA-PEG-PH20-NPs were more efficient than other treatments for inducing tumor cell apoptosis (FIG. 14C). Furthermore, the TUNEL staining was more uniformly distributed in tumors treated with DOX-PLGA-PEG-PH20-NPs than those treated with nanoparticles without conjugated PH20, suggesting a good diffusion and deep penetration of PLGA-PEG-PH20-NPs.

Figure 14D:
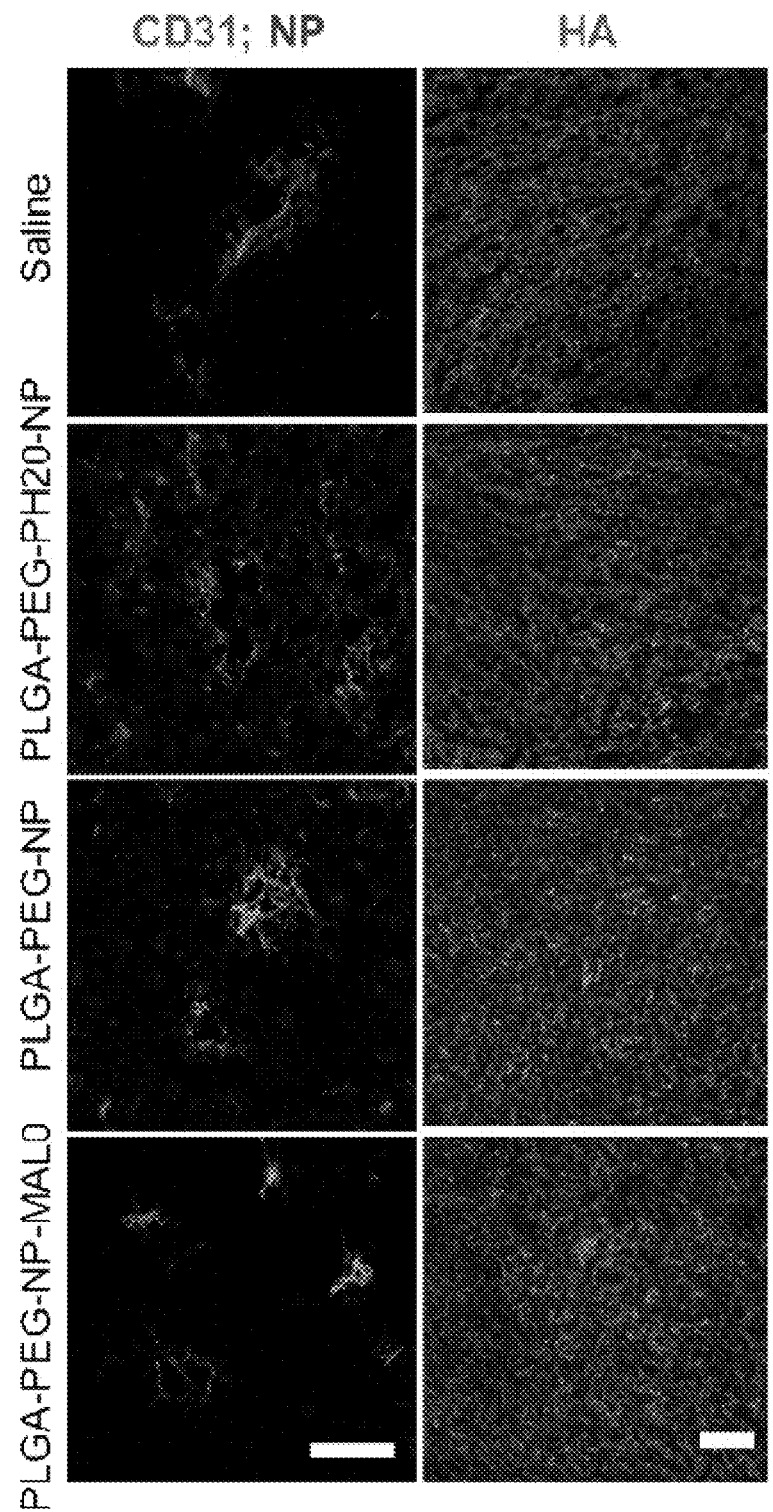
FIG. 14D shows images of sectioned tumors that were collected 24 hours after administration of saline or nanoparticles. The mice were injected intravenously with saline or DiD-labeled nanoparticles on day 9 post 4T1 cell inoculation. The left column shows tumors with CD31 staining (green, representing blood vessels) and the distribution of nanoparticles (Red). (The scale bar is 100 µm). The right column shows the HA staining of the tumor sections (The scale bar is 50 µm).
Figure 21B:
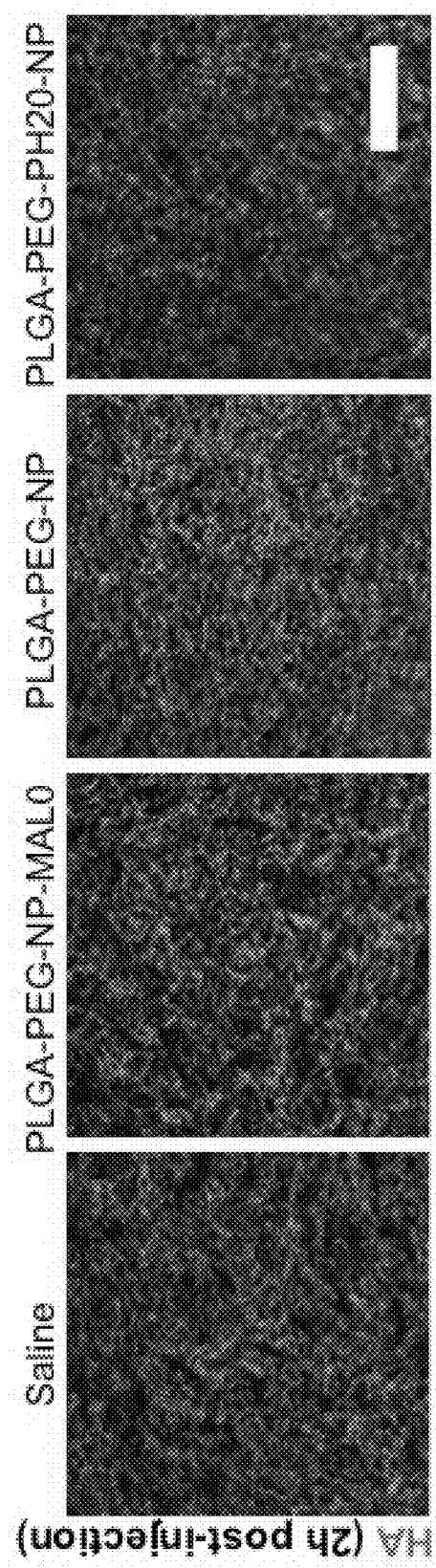
FIG. 21B shows images of HA stained tumor sections. The tumors were collected 2 h after tail vein injection of nanoparticles or controls. Green: Hyaluronan (HA) (The scale bar: 50 μm).

To demonstrate that the spatially uniform distribution of apoptotic tumor cells was caused by the enhanced nanoparticle penetration, tumors were harvested 24 h after systematic administration of DiD-labeled nanoparticles. The sectioned tumor tissues were stained with CD31, marking blood vessels (FIG. 14D left). There was only a barely detectable nanoparticle signal (red) in tumors treated with PLGA-PEG-NP-MAL0 due to the short circulation time of the nanoparticles, consistent with the biodistribution study. With a longer circulation time, PLGA-PEG-NPs were able to accumulate at higher levels in the tumors. Significantly larger amounts and better-distributed nanoparticle signals around blood vessels were observed in tumors treated with PLGA-PEG-PH20-NPs, which contributed to the pattern of apoptotic cells in tumors. Staining of HA for tumors that had been treated for 24 h did not show a detectable difference between the four treatments (FIG. 14D right), indicating that the majority of tumor HA remained intact under the treatment with PLGA-PEG-PH20-NPs. Similar results were obtained in a short treatment of 2 h (FIG. 21B).

These results from animal studies with the in vitro cell study demonstrated that PLGA-PEG-PH20-NPs enables efficient therapeutic delivery because the conjugated PH20 only degrades HA along the path of nanoparticle diffusion while still maintaining the major basic structure of HA in ECM.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

What is claimed is:

1. A delivery system, comprising: an organic nanoparticle; and a hyaluronidase anchored or conjugated to the organic nanoparticle.

2. The delivery system of claim 1, wherein the organic nanoparticle is selected from a polymer-based nanoparticle, a lipid-based nanoparticle and a nanoparticle formed by lipid-like molecules.

3. The delivery system of claim 1, wherein the hyaluronidase is anchored or conjugated to the organic nanoparticle via a linker or spacer.

4. The delivery system of claim 1, wherein the organic nanoparticle has a diameter of from about 10 to about 500 nm, or from about 20 to about 400 nm, or from about 40 to about 300 nm, or from about 60 to about 250 nm.

5. The delivery system of claim 2, wherein the organic nanoparticle is a polymer-based nanoparticle that comprises one or more biodegradable polymers.

6. The delivery system of claim 5, wherein the one or more biodegradable polymers are selected from polyesters, polyhydroxybutyric acids, polyhydroxyvaleric acids, polycaprolactones, polyesteramides, polycyanoacrylates, poly(amino acids), polycarbonates, polyanhydrides, and combinations thereof.

7. The delivery system of claim 5, wherein the biodegradable polymers are selected from polylactic acid (polylactide), polylactide-polyglycolide, polyglycolide, poly(lactide-co-glycolide), polyethylene glycol-co-lactide and combinations thereof.

8. The delivery system of claim 1, wherein the organic nanoparticle is a liposome and the liposome has an aqueous inner core.

9. The delivery system of claim 3, wherein the linker or spacer is anchored or conjugated to the organic nanoparticle and covalently bound to the hyaluronidase.

10. The delivery system of claim 9, wherein the linker or spacer is a linker with two reactive groups capable of forming covalent bonds.

11. The delivery system of claim 9, wherein the linker or spacer is a spacer with one reactive group capable of forming a covalent bond.

12. The delivery system of claim 9, wherein the linker or spacer comprises a polyamino acid chain.

13. The delivery system of claim 9, wherein the linker or spacer comprises a maleimide group, an N-hydroxysuccinimide ester group, a sulfo-N-hydroxysuccinimide ester group, or an imidoester group.

14. The delivery system of claim 1, further comprising an active phamlaceutical agent encapsulated in the organic nanoparticle, or conjugated or anchored to an outer surface of the organic nanoparticle.

15. The delivery system of claim 14, wherein the active pharmaceutical agent is an anti-cancer drug selected from alkylating agents, antimetabolites, antigens, and radiosensitizers.

16. The delivery system of claim 14, wherein the active pharmaceutical agent is a cytotoxic agent.

17. The delivery system of claim 16, wherein the cytotoxic agent is selected from docetaxel, paclitaxel and paclitaxel palmitate.

18. The delivery system of claim 1, further comprising a diagnostic agent encapsulated in the organic nanoparticle, or conjugated or anchored on an outer surface of the organic nanoparticle.

19. The delivery system of claim 18, wherein the diagnostic agent is selected from a radiolabelled compound, fluorescently labeled compound, enzymatically labeled compound, magnetic compound .

20. The delivery system of claim 1, further comprising an antigen encapsulated in the organic nanoparticle.

21. The delivery system of claim 1, wherein the organic nanoparticle comprises a lipid-based membrane on an outer surface thereof, and the linker or spacer is anchored or conjugated to the lipid-based membrane.

22. The delivery system of claim 21, wherein the lipid-based membrane is selected from plasm a membrane isolated from a live cell, membrane of cellular organelle isolated from a live cell, and viral membrane.

23. The delivery system of claim 21, wherein the lipid-based membrane is isolated from a blood cell selected from red blood cell, white blood cell and platelet.

24. The delivery system of claim 1, further comprising an antibody conjugated on surface of the organic nanoparticle, wherein the antibody specifically binds to a surface antigen on a target tissue for the delivery system.

25. The delivery system of claim 1, further comprising a polyethylene glycol polymer, a polysaccharide, a polyamino acid or a zwitterionic polymer anchored or conjugated on a same surface of the nanoparticle as the hyaluronidase.

* * * * *